United States Patent
Sagehashi et al.

(10) Patent No.: US 9,115,074 B2
(45) Date of Patent: Aug. 25, 2015

(54) FLUORINATED MONOMER, POLYMER, RESIST COMPOSITION, AND PATTERNING PROCESS

(71) Applicant: SHIN-ETSU CHEMICAL CO., LTD., Chiyoda-ku, Tokyo (JP)

(72) Inventors: Masayoshi Sagehashi, Joetsu (JP); Koji Hasegawa, Joetsu (JP); Takeshi Sasami, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 42 days.

(21) Appl. No.: 14/142,588

(22) Filed: Dec. 27, 2013

(65) Prior Publication Data

US 2014/0114080 A1   Apr. 24, 2014

Related U.S. Application Data

(62) Division of application No. 13/081,182, filed on Apr. 6, 2011, now Pat. No. 8,647,808.

(30) Foreign Application Priority Data

Apr. 7, 2010   (JP) .................. 2010-088537

(51) Int. Cl.
| | |
|---|---|
| *C07C 69/013* | (2006.01) |
| *C07C 69/653* | (2006.01) |
| *G03F 7/004* | (2006.01) |
| *C07D 317/34* | (2006.01) |
| *C07D 317/72* | (2006.01) |
| *C08F 220/22* | (2006.01) |
| *C08F 220/24* | (2006.01) |
| *C08F 220/18* | (2006.01) |
| *C08F 222/18* | (2006.01) |
| *C08F 222/20* | (2006.01) |
| *C08F 222/22* | (2006.01) |
| *C08F 220/28* | (2006.01) |
| *G03F 7/039* | (2006.01) |
| *C08F 24/00* | (2006.01) |

(52) U.S. Cl.
CPC ............ *C07C 69/013* (2013.01); *C07C 69/653* (2013.01); *C07D 317/34* (2013.01); *C07D 317/72* (2013.01); *C08F 24/00* (2013.01); *C08F 220/22* (2013.01); *C08F 220/24* (2013.01); *C08F 220/28* (2013.01); *C08F 222/18* (2013.01); *C08F 222/20* (2013.01); *C08F 222/22* (2013.01); *G03F 7/0046* (2013.01); *G03F 7/0397* (2013.01); *Y10S 430/108* (2013.01); *Y10S 430/111* (2013.01)

(58) Field of Classification Search
CPC .. C07C 69/653; C07C 69/013; C07D 317/34; C07D 317/72; G03F 7/0397; G03F 7/0046; C08F 220/22; C08F 220/24; C08F 220/28; C08F 222/18; C08F 222/20; C08F 222/22

USPC .............. 549/331, 333, 341, 342, 429, 430; 560/183, 184, 205, 219, 220; 430/270.1, 326, 907, 910; 526/242, 526/245, 270, 321, 325

See application file for complete search history.

(56) References Cited

U.S. PATENT DOCUMENTS

| | | | |
|---|---|---|---|
| 5,650,483 | A | 7/1997 | Malik et al. |
| 6,312,867 | B1 | 11/2001 | Kinsho et al. |

(Continued)

FOREIGN PATENT DOCUMENTS

| | | |
|---|---|---|
| JP | 9-246173 A | 9/1997 |
| JP | 2000-336121 A | 12/2000 |

(Continued)

OTHER PUBLICATIONS

Hirayama, "Resist and Cover Material Investigation for Immersion Lithography", 2nd Immersion Workshop, Jul. 11, 2003, 16 pages.

(Continued)

*Primary Examiner* — John Chu
(74) *Attorney, Agent, or Firm* — Birch, Stewart, Kolasch & Birch, LLP

(57) ABSTRACT

A fluorinated monomer has formula (1) wherein $R^1$ is H, F, methyl or trifluoromethyl, $R^2$ and $R^3$ are H or a monovalent hydrocarbon group, $R^4$ to $R^6$ each are a monovalent fluorinated hydrocarbon group, A is a divalent hydrocarbon group, and $k^1$ is 0, 1 or 2. A polymer derived from the fluorinated monomer may be endowed with appropriate water repellency, water slip, acid lability and hydrolysis and is useful as an additive polymer in formulating a resist composition.

(1)

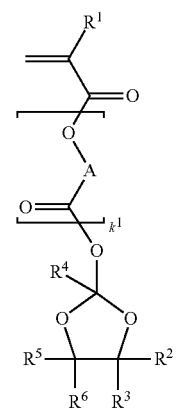

1 Claim, No Drawings

(56) References Cited

U.S. PATENT DOCUMENTS

| | | | |
|---|---|---|---|
| 7,455,952 | B2 | 11/2008 | Hatakeyama et al. |
| 7,537,880 | B2 | 5/2009 | Harada et al. |
| 7,867,690 | B2 * | 1/2011 | Nakayama et al. ........ 430/270.1 |
| 7,868,199 | B2 | 1/2011 | Hasegawa et al. |
| 8,211,612 | B2 | 7/2012 | Maeda et al. |
| 2002/0147290 | A1 * | 10/2002 | Nakashima et al. .......... 526/266 |
| 2007/0105044 | A1 | 5/2007 | Maeda et al. |
| 2007/0122736 | A1 | 5/2007 | Hatakeyama et al. |
| 2008/0090172 | A1 | 4/2008 | Hatakeyama et al. |
| 2009/0053650 | A1 | 2/2009 | Irie |

FOREIGN PATENT DOCUMENTS

| | | |
|---|---|---|
| JP | 2006-91798 A | 4/2006 |
| JP | 2007-140446 A | 6/2007 |
| JP | 2007-187887 A | 7/2007 |
| JP | 2007-204385 A | 8/2007 |
| JP | 2008-111103 A | 5/2008 |
| JP | 2008-122932 A | 5/2008 |
| JP | 2010-2599 A | 1/2010 |

OTHER PUBLICATIONS

Ito et al., "Aliphatic platforms for the design of 157 nm chemically amplified resists", Proceedings of SPIE, 2002, vol. 4690, pp. 18-28.

Lin, "Semiconductor Foundry, Lithography, and Partners", Proceedings of SPIE, 2002, vol. 4690, xxix-xlii.

Murase et al., "Characterization of molecular interfaces in hydrophobic systems", Progress in Organic Coatings, 1997, 31, pp. 97-104.

Nakano et al., "Defectivity data taken with a full-field immersion exposure tool", 2nd International symposium on Immersion Lithography, Sep. 12-15, 2005, pp. 1-27.

Owa, "Immersion lithography; its potential performance and issues", Proceedings of SPIE, 2003, vol. 5040, pp. 724-733.

Shirota et al., "Development of non-topcoat resist polymers for 193-nm immersion lithography", Proceedings of SPIE, 2007, vol. 6519, pp. 651905-1-651905-11.

* cited by examiner

FLUORINATED MONOMER, POLYMER, RESIST COMPOSITION, AND PATTERNING PROCESS

CROSS-REFERENCE TO RELATED APPLICATION

The present application is a 37 C.F.R. §1.53(b) divisional of, and claims priority to, U.S. application Ser. No. 13/081,182, filed Apr. 6, 2011. Priority is also claimed to Application No. 2010-088537 filed in Japan on Apr. 7, 2010. The entire contents of each of these applications is hereby incorporated by reference.

TECHNICAL FIELD

This invention relates to novel fluorinated monomers (or polymerizable compounds) which are useful as raw materials for the synthesis of functional, pharmaceutical and agricultural chemicals. In conjunction with a photolithography process for the microfabrication of semiconductor devices, and particularly to an immersion photolithography process involving directing ArF excimer laser radiation having a wavelength of 193 nm from a projection lens toward a resist-coated substrate, with a liquid (e.g., water) intervening between the lens and the substrate, the fluorinated monomer is useful in forming an additive polymer to be added to formulate a radiation-sensitive resist composition having high transparency and improved development properties.

This invention also relates to a polymer comprising recurring units derived from the fluorinated monomer, a photoresist composition comprising the polymer, and a process for forming a pattern using the photoresist composition.

BACKGROUND ART

In the recent drive for higher integration and operating speeds in LSI devices, the pattern rule is made drastically finer. The background supporting such a rapid advance is a reduced wavelength of the light source for exposure. The change-over from i-line (365 nm) of a mercury lamp to shorter wavelength KrF excimer laser (248 nm) enabled mass-scale production of dynamic random access memories (DRAM) with an integration degree of 64 MB (processing feature size ≤0.25 µm). To establish the micropatterning technology necessary for the fabrication of DRAM with an integration degree of 256 MB and 1 GB or more, the lithography using ArF excimer laser (193 nm) is under active investigation. The ArF excimer laser lithography, combined with a high NA lens (NA 0.9), is considered to comply with 65-nm node devices. For the fabrication of next 45-nm node devices, the $F_2$ laser lithography of 157 nm wavelength became a candidate. However, because of many problems including a cost and a shortage of resist performance, the employment of $F_2$ lithography was postponed. ArF immersion lithography was proposed as a substitute for the $F_2$ lithography (see Proc. SPIE Vol. 4690, xxix, 2002).

In the ArF immersion lithography, the space between the projection lens and the wafer is filled with water and ArF excimer laser is irradiated through the water. Since water has a refractive index of 1.44 at 193 nm, pattern formation is possible even using a lens with NA of 1.0 or greater. The theoretically possible maximum NA is 1.44. The resolution is improved by an increment of NA. A combination of a lens having NA of at least 1.2 with ultra-high resolution technology suggests a way to the 45-nm node (see Proc. SPIE Vol. 5040, p. 724, 2003).

The ArF immersion lithography has a possibility that water-soluble components in the resist film be leached in immersion water during exposure. Specifically an acid generated during exposure and a basic compound previously added to the resist material can be leached in immersion water. As a result, pattern profile changes and pattern collapse can occur. It is also pointed out that if the resist film is less water repellent, water droplets remaining on the resist film after scanning, though in a minute volume, can penetrate into the resist film to generate defects. It was then proposed to provide a protective coating between the resist film and water to prevent resist components from being leached out and water from penetrating into the resist film, the process being referred to as "topcoat process." See 2nd Immersion Workshop: Resist and Cover Material Investigation for Immersion Lithography, 2003.

In the ArF immersion lithography using a topcoat, a protective coating material which is soluble in alkaline developer is advantageous. This eliminates the step of stripping off the protective coating, offering great cost and process merits. Thus, great efforts have been devoted to develop water-insoluble resist protective coating materials, for example, resins having alkali-soluble units such as fluorinated alcohol, carboxyl or sulfo groups, as described in JP-A 2006-91798.

On the other hand, a process for preventing resist components from being leached out and water from penetrating into the resist film without a need for a protective coating material has also been developed, the process being referred to as "topcoatless process", as described in JP-A 2007-187887. In the topcoatless process, an alkali-soluble hydrophobic polymer is added to the resist material as a surfactant, whereupon the hydrophobic compound is segregated at the resist surface during resist film formation. The process is thus expected to achieve equivalent effects to the use of resist protective coating material. Additionally, the process is economically advantageous over the use of a resist protective film because steps of forming and removing the protective film are unnecessary.

In either of the topcoat and topcoatless processes, the ArF immersion lithography requires a scanning speed of about 300 to 700 mm/sec in order to gain higher throughputs. In the event of such high-speed scanning, if the water repellency of the resist or protective film is insufficient, water droplets may be left on the film surface after scanning. Residual droplets may cause defects. To eliminate such defects, it is necessary to improve the water repellency of the relevant coating film and the flow or mobility of water (hereinafter, water slip) on the film. The film material must be designed so as to increase the receding contact angle (see 2nd International Symposium on Immersion Lithography, 12-15 Sep., 2005, Defectivity data taken with a full-field immersion exposure tool, Nakano et al). In connection with such polymer design, it is reported that introduction of fluorine is effective for improving water repellency, and formation of micro-domain structure by a combination of different water repellent groups is effective for improving water slip. See Progress in Organic Coatings, 31, p. 97 (1997).

One exemplary material known to have excellent water slip and water repellency on film surface is a copolymer of α-trifluoromethylacrylate and norbornene derivative (Proc. SPIE Vol. 4690, p. 18, 2002). While this polymer was developed as the resin for $F_2$ (157 nm) lithography resist materials, it is characterized by a regular arrangement of molecules of (highly water repellent) α-trifluoromethylacrylate and norbornene derivative in a ratio of 2:1. When a water molecule interacts with methyl and trifluoromethyl groups, there is a tendency that the orientation distance between water and methyl is longer. A resin having a regular arrangement of both substituent groups is improved in water slip because of a longer orientation distance of water. In fact, when this polymer is used as the base polymer in a protective coating for immersion lithography, water slip is drastically improved (see US 20070122736 or JP-A 2007-140446). Another example of the highly water repellent/water slippery material is a fluorinated ring-closing polymerization polymer having hexafluoroalcohol groups on side chains. This polymer is further improved in water slip by protecting hydroxyl groups on side chains with acid labile groups, as reported in Proc. SPIE Vol. 6519, p. 651905 (2007).

Although the introduction of fluorine into resins is effective for improving water repellency and water slip, the introduction of extra fluorine can induce new defects known as "blob defects". Blob defects are likely to form during spin drying after development, particularly when the film has a high surface contact angle after development. One approach for suppressing blob defects is by introducing highly hydrophilic substituent groups (e.g., carboxyl or sulfo groups) into a resin to reduce the surface contact angle after development. However, since these groups serve to reduce the water repellency and water slip of the resin, this approach is not applicable to high-speed scanning. There is a desire to have a resin material which can minimize blob defects while maintaining highly water repellent and water slip properties during immersion lithography.

The highly water repellent/water slippery materials discussed above are expected to be applied not only to the ArF immersion lithography, but also to the resist material for mask blanks. Resist materials for mask blanks are subject to long-term exposure in vacuum. It is pointed out that sensitivity variations or profile changes can occur as an amine component in the resist material is adsorbed to the resist film surface during the long-term exposure. It was then proposed to add a compound having surface active effect to modify the surface of a resist film for preventing adsorption of amine to the resist film.

CITATION LIST

Patent Document 1: U.S. Pat. No. 7,455,952 (JP-A 2006-91798)
Patent Document 2: JP-A 2007-187887
Patent Document 3: US 20070122736 (JP-A 2007-140446)
Non-Patent Document 1: Proc. SPIE Vol. 4690, xxix, 2002
Non-Patent Document 2: Proc. SPIE Vol. 5040, p. 724, 2003
Non-Patent Document 3: 2nd Immersion Workshop:
  Resist and Cover Material Investigation for Immersion Lithography (2003)
Non-Patent Document 4: 2nd International Symposium on Immersion Lithography, 12-15 Sep., 2005, Defectivity data taken with a full-field immersion exposure tool, Nakano et al.
Non-Patent Document 5: Progress in Organic Coatings, 31, p. 97 (1997)
Non-Patent Document 6: Proc. SPIE Vol. 4690, p. 18 (2002)
Non-Patent Document 7: Proc. SPIE Vol. 6519, p. 651905 (2007)

SUMMARY OF INVENTION

An object of the invention is to provide a novel fluorinated monomer; a polymer derived therefrom and suited as an additive polymer in resist compositions; a resist composition, especially chemically amplified positive resist composition comprising the additive polymer so that the composition exhibits excellent water repellency and water slip and forms a resist pattern of satisfactory profile after development, the pattern having few development defects; and a pattern forming process using the composition. The additive polymer used herein is highly transparent to radiation with wavelength of up to 200 nm. Various properties of the polymer including water repellency, water slip, fat solubility, acid lability, and hydrolysis may be adjusted by a choice of polymer structure. The monomer can be prepared from reactants which are readily available and easy to handle.

The inventors have found that when a polymer having a plurality of fluorinated alkylcarbonyloxy groups in recurring units is used as an additive to formulate a resist composition, the resist composition forms a resist film which has sufficient water repellency and water slip to withstand high-speed scanning without a need for a resist protective film. Since the polymer is susceptible to hydrolysis in alkaline developer, the resist film surface after development is modified hydrophilic, which is effective for substantially reducing blob defects.

Accordingly, the present invention provides a fluorinated monomer, a polymer, a resist composition, and a pattern forming process, as defined below.

In a first aspect, the invention provides a fluorinated monomer having the general formula (1):

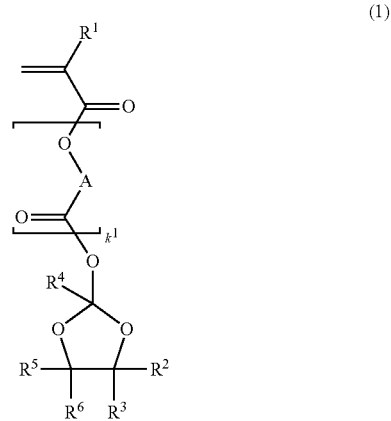

(1)

wherein $R^1$ is hydrogen, fluorine, methyl or trifluoromethyl, $R^2$ and $R^3$ are each independently hydrogen or a straight, branched or cyclic $C_1$-$C_{15}$ monovalent hydrocarbon group, $R^2$ and $R^3$ may bond together to form a non-aromatic ring with the carbon atom to which they are attached, $R^4$ to $R^6$ each are a $C_1$-$C_6$ monovalent fluorinated hydrocarbon group, A is a straight, branched or cyclic $C_1$-$C_{10}$ divalent hydrocarbon group, and $k^1$ is an integer of 0 to 2.

In a second aspect, the invention provides a polymer comprising recurring units of the general formula (1a):

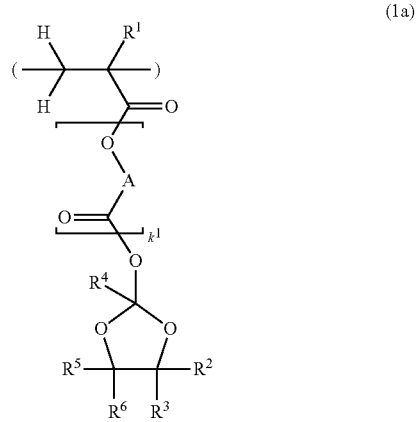

(1a)

wherein $R^1$ to $R^6$, A, and $k^1$ are as defined above.

In a third aspect, the invention provides a resist composition comprising (A) a polymer comprising recurring units of the general formula (1a), (B) a polymer having a lactone ring-derived structure, hydroxyl-containing structure and/or maleic anhydride-derived structure as a base resin, said base polymer becoming soluble in alkaline developer under the action of acid, (C) a compound capable of generating an acid upon exposure to high-energy radiation, and (D) an organic solvent.

A preferred embodiment provides a resist composition comprising (A) a polymer comprising recurring units of the general formula (1a) defined above and recurring units of one or more type selected from the general formulae (2a) to (2i), (B) a polymer having a lactone ring-derived structure, hydroxyl-containing structure and/or maleic anhydride-derived structure as a base resin, said base polymer becoming soluble in alkaline developer under the action of acid, (C) a compound capable of generating an acid upon exposure to high-energy radiation, and (D) an organic solvent.

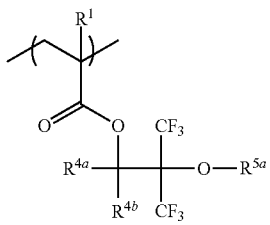
(2a)

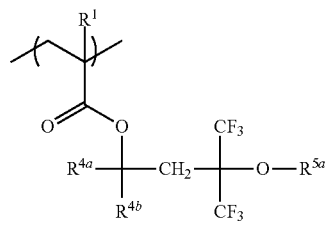
(2b)

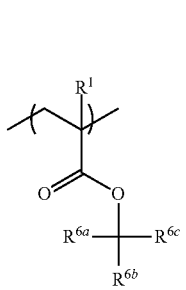
(2c)

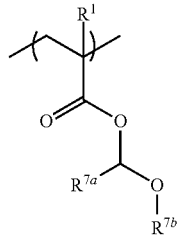
(2d)

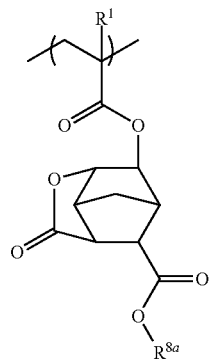
(2e)

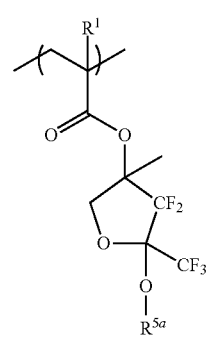
(2f)

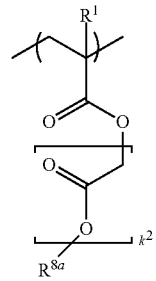
(2g)

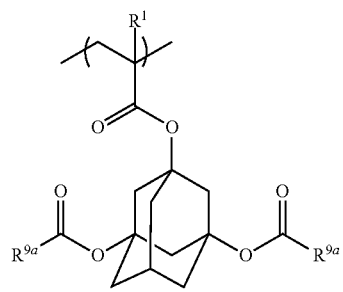
(2h)

(2i)

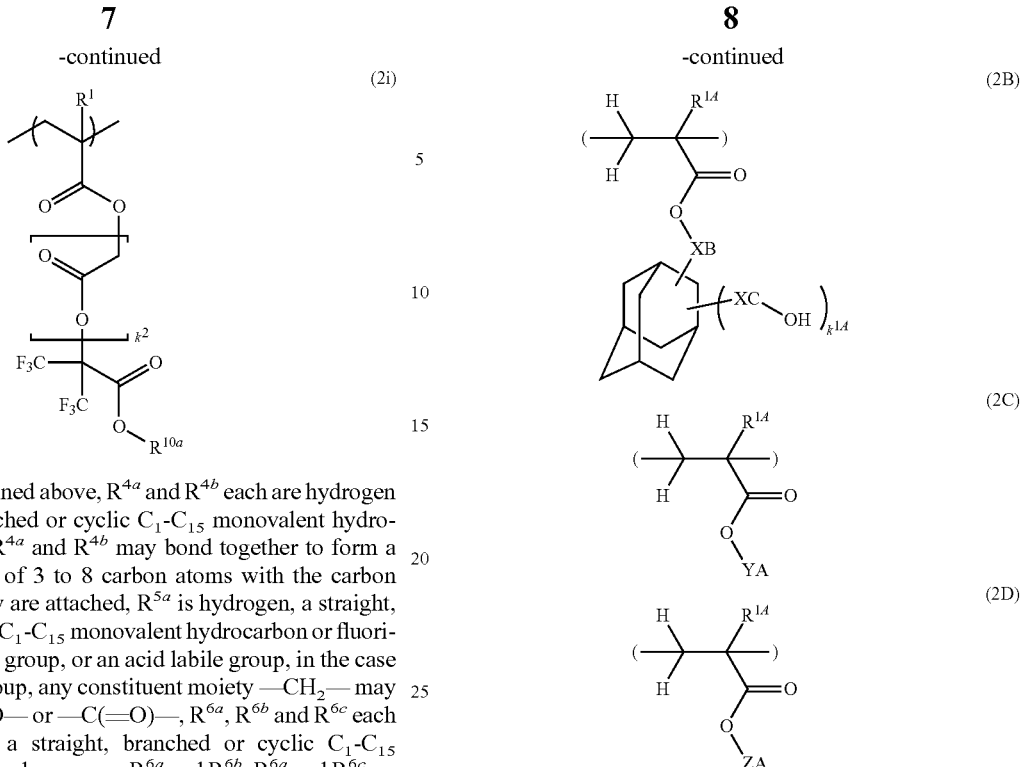

(2A)

(2B)

(2C)

(2D)

Herein $R^1$ is as defined above, $R^{4a}$ and $R^{4b}$ each are hydrogen or a straight, branched or cyclic $C_1$-$C_{15}$ monovalent hydrocarbon group, or $R^{4a}$ and $R^{4b}$ may bond together to form a non-aromatic ring of 3 to 8 carbon atoms with the carbon atom to which they are attached, $R^{5a}$ is hydrogen, a straight, branched or cyclic $C_1$-$C_{15}$ monovalent hydrocarbon or fluorinated hydrocarbon group, or an acid labile group, in the case of hydrocarbon group, any constituent moiety —$CH_2$— may be replaced by —O— or —C(=O)—, $R^{6a}$, $R^{6b}$ and $R^{6c}$ each are hydrogen, or a straight, branched or cyclic $C_1$-$C_{15}$ monovalent hydrocarbon group, $R^{6a}$ and $R^{6b}$, $R^{6a}$ and $R^{6c}$, or $R^{6b}$ and $R^{6c}$ may bond together to form a non-aromatic ring of 3 to 8 carbon atoms with the carbon atom to which they are attached, $R^{7a}$ is hydrogen or a straight, branched or cyclic $C_1$-$C_{15}$ monovalent hydrocarbon group, $R^{7b}$ is a straight, branched or cyclic $C_1$-$C_{15}$ monovalent hydrocarbon group, $R^{7a}$ and $R^{7b}$ may bond together to form a non-aromatic ring of 3 to 8 carbon atoms with the carbon and oxygen atoms to which they are attached, $R^{8a}$ is a straight, branched or cyclic $C_1$-$C_{15}$ monovalent fluorinated hydrocarbon group, $R^{9a}$ is a straight, branched or cyclic $C_1$-$C_{10}$ monovalent fluorinated hydrocarbon group, $R^{10a}$ is a straight, branched or cyclic $C_1$-$C_{15}$ monovalent hydrocarbon group which may contain halogen or oxygen, and $k^2$ is 0 or 1.

In a preferred embodiment, the polymer (B) is selected from the group consisting of (meth)acrylate polymers, (α-trifluoromethyl)acrylate-maleic anhydride copolymers, cycloolefin-maleic anhydride copolymers, polynorbornene, polymers resulting from ring-opening metathesis polymerization of cycloolefins, hydrogenated polymers resulting from ring-opening metathesis polymerization of cycloolefins, polyhydroxystyrene, copolymers of hydroxystyrene with one or more (meth)acrylate, styrene, vinylnaphthalene, vinylanthracene, vinylpyrene, hydroxyvinylnaphthalene, hydroxyvinylanthracene, indene, hydroxyindene, acenaphthylene, or norbornadiene derivatives, and novolac resins.

In a preferred embodiment, the polymer (B) comprises recurring units of at least one type selected from the general formulae (2A) to (2D).

Herein $R^{14}$ is hydrogen, fluorine, methyl or trifluoromethyl, XA is an acid labile group, XB and XC each are a single bond or a straight or branched $C_1$-$C_4$ divalent hydrocarbon group, YA is a substituent group having a lactone structure, ZA is hydrogen, or a $C_1$-$C_1$, fluoroalkyl group or $C_1$-$C_{15}$ fluoroalcohol-containing substituent group, and $k^{14}$ is an integer of 1 to 3.

Preferably the polymer (A) comprising recurring units of formula (1a) is added in an amount of 0.1 to 50 parts by weight per 100 parts by weight of the polymer (B).

The resist composition may further comprise (E) a basic compound and/or (F) a dissolution regulator.

In a fourth aspect, the invention provides:

a pattern forming process comprising the steps of (1) applying the resist composition defined above onto a substrate to form a resist coating, (2) heat treating the resist coating and exposing it to high-energy radiation through a photomask, and (3) developing the exposed coating with a developer;

a pattern forming process comprising the steps of (1) applying the resist composition defined above onto a substrate to form a resist coating, (2) heat treating the resist coating and exposing it to high-energy radiation from a projection lens through a photomask while holding a liquid between the substrate and the projection lens, and (3) developing the exposed coating with a developer; or a pattern forming process comprising the steps of (1) applying the resist composition defined above onto a substrate to form a resist coating, (2) forming a protective coating onto the resist coating, (3) heat treating the resist coating and exposing it to high-energy radiation from a projection lens through a photomask while holding a liquid between the substrate and the projection lens, and (4) developing with a developer.

Most often the liquid is water. The high-energy radiation has a wavelength in the range of 180 to 250 nm.

In a further aspect, the invention provides a pattern forming process comprising the steps of (1) applying the resist composition defined above onto a mask blank to form a resist coating, (2) heat treating the resist coating and exposing it in vacuum to electron beam, and (3) developing with a developer.

Advantageous Effects of Invention

The fluorinated monomer is useful as a raw material for the production of functional, pharmaceutical, and agricultural chemicals and can be prepared from reactants which are readily available and easy to handle. The polymer derived therefrom is useful as an additive polymer to formulate a radiation-sensitive resist composition which has high transparency to radiation having a wavelength of up to 500 nm, especially up to 300 nm and forms a resist pattern having few development defects. The polymer is designed such that any of its properties including water repellency, water slip, fat solubility, acid lability and hydrolysis may be tailored by a choice of a proper structure.

DESCRIPTION OF EMBODIMENTS

The singular forms "a", "an" and "the" include plural referents unless the context clearly dictates otherwise. The notation (Cn-Cm) means a group containing from n to m carbon atoms per group. The abbreviation "phr" is parts by weight per 100 parts by weight of the base resin.

While a certain compound is herein represented by a chemical formula, many compounds have a chemical structure for which there can exist enantiomers or diastereomers. Each chemical formula collectively represents all such stereoisomers, unless otherwise stated. Such stereoisomers may be used alone or in admixture.

Fluorinated Monomer

One embodiment of the invention is a fluorinated monomer having the general formula (1).

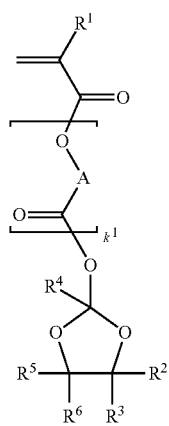
(1)

Herein $R^1$ is hydrogen, fluorine, methyl or trifluoromethyl, $R^2$ and $R^3$ are each independently hydrogen or a straight, branched or cyclic $C_1$-$C_{15}$ monovalent hydrocarbon group, $R^2$ and $R^3$ may bond together to form a non-aromatic ring with the carbon atom to which they are attached, $R^4$ to $R^6$ each are a $C_1$-$C_6$ monovalent fluorinated hydrocarbon group, A is a straight, branched or cyclic $C_1$-$C_{10}$ divalent hydrocarbon group, and $k^1$ is an integer of 0 to 2.

Examples of the straight, branched or cyclic $C_1$-$C_{15}$ monovalent hydrocarbon group represented by $R^2$ and $R^3$ include, but are not limited to, straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, and adamantyl; and substituted forms of the foregoing in which some hydrogen atoms are replaced by fluorine, hydroxyl, alkoxy, carboxy, alkoxycarbonyl, oxo or other radicals.

Examples of the non-aromatic ring (or alicyclic) that is formed by $R^2$ and $R^3$ include, but are not limited to, the following.

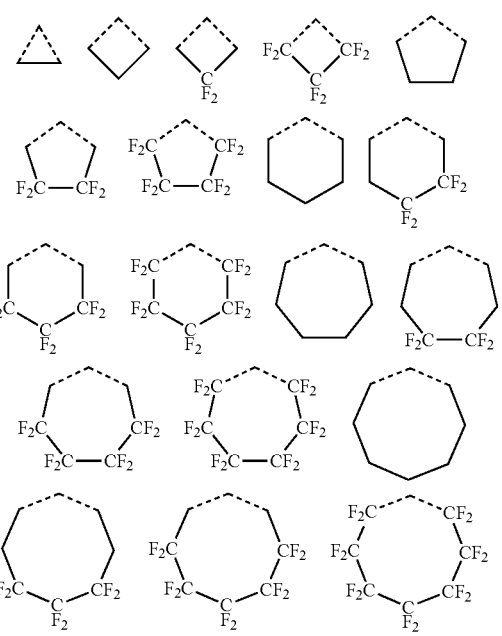

Herein and throughout the specification, the broken line designates a valence bond.

Examples of the $C_1$-$C_6$ monovalent fluorinated hydrocarbon group represented by $R^4$ to $R^6$ are given below, but not limited thereto.

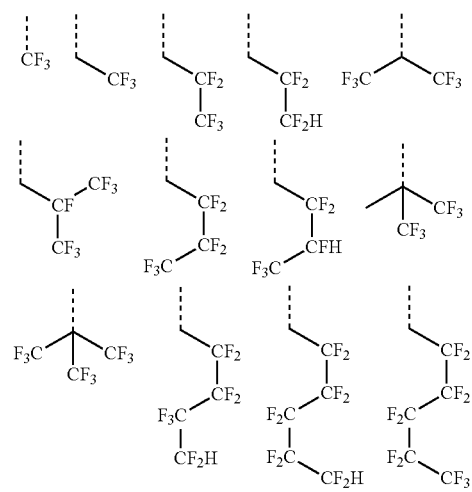

Examples of the straight, branched or cyclic $C_1$-$C_{10}$ divalent hydrocarbon group represented by A are given below.

Illustrative, non-limiting examples of the compound having formula (1) are given below.

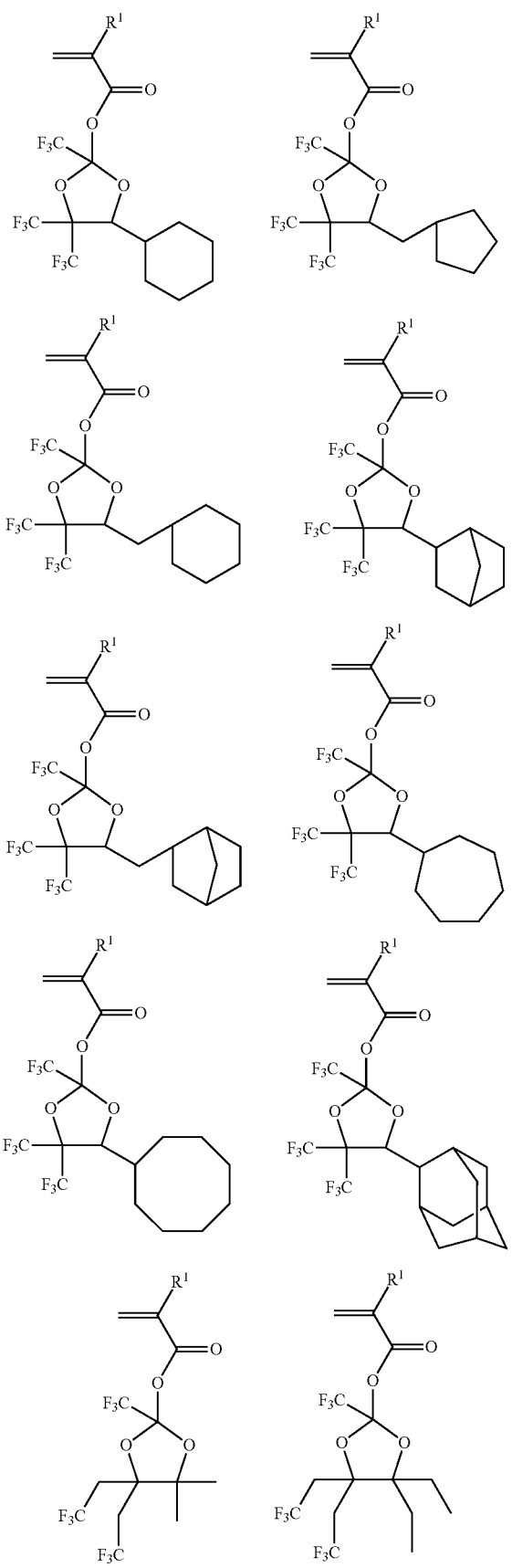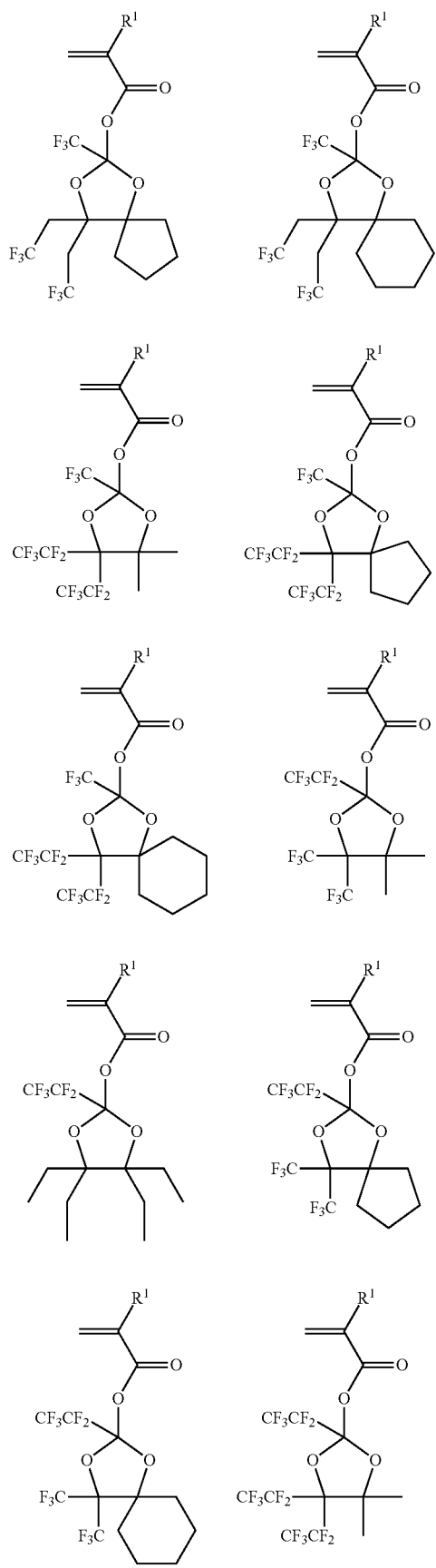

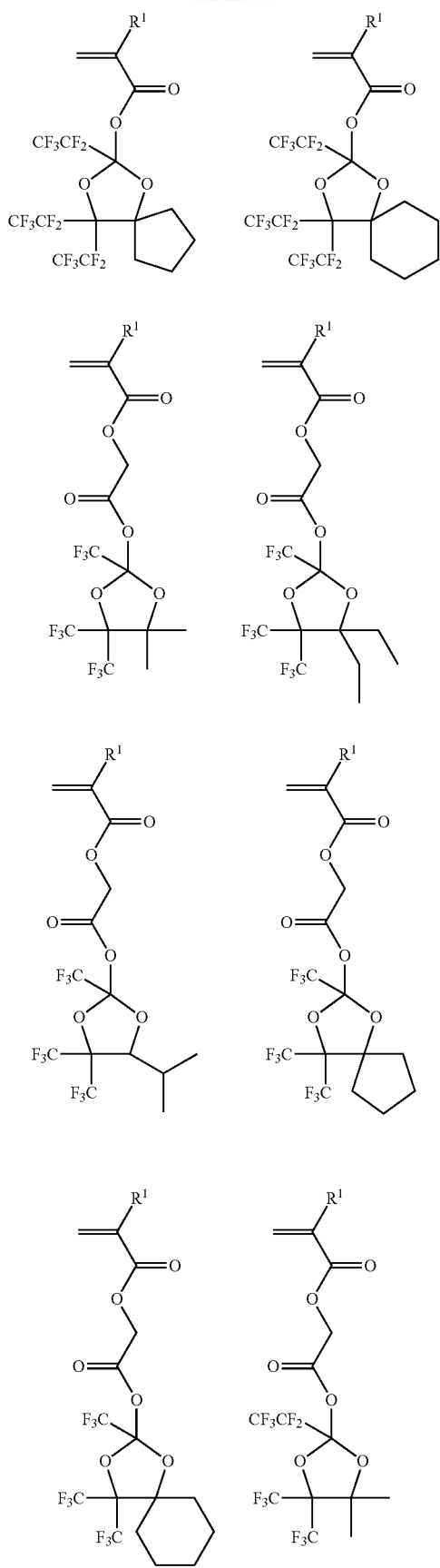
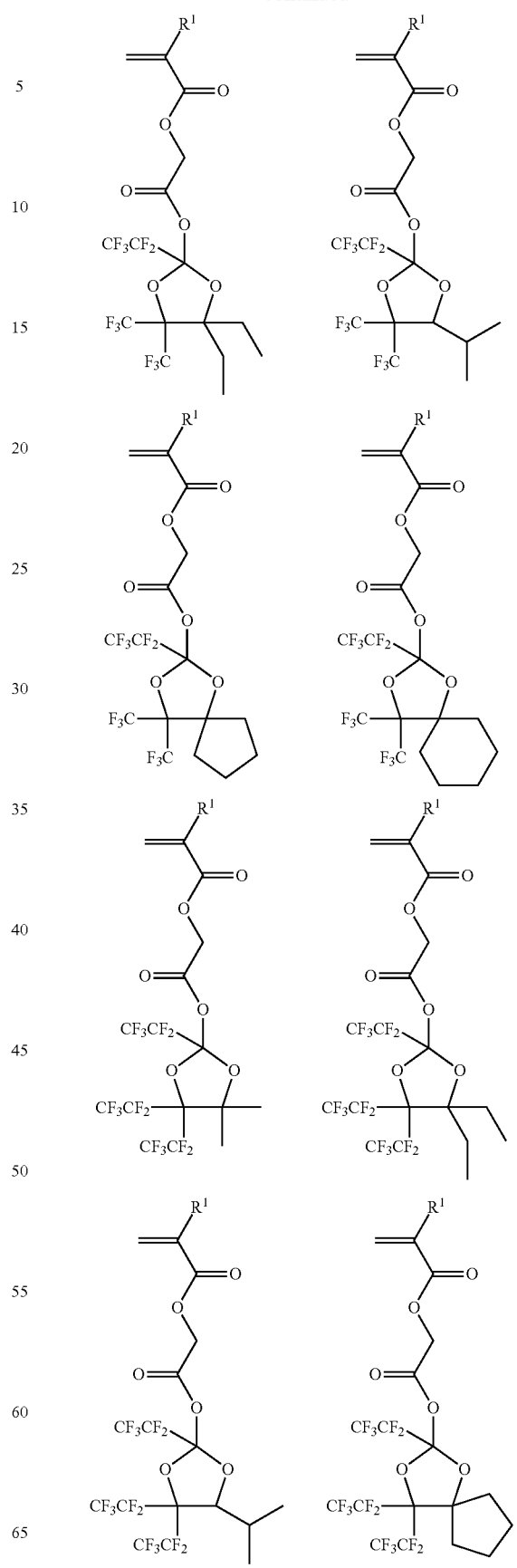

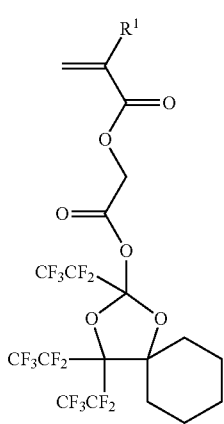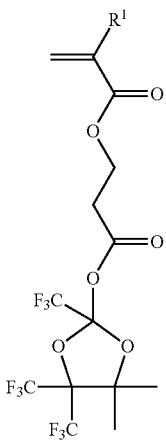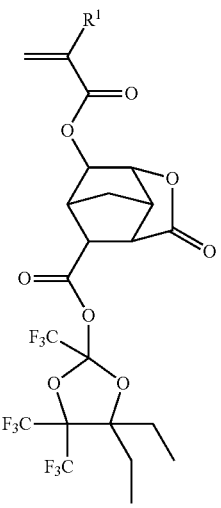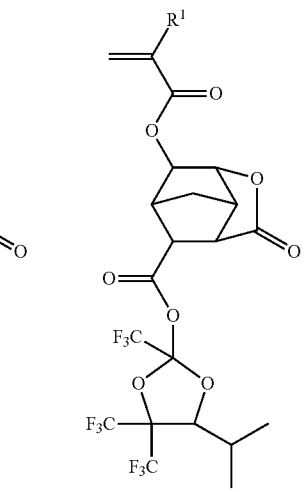
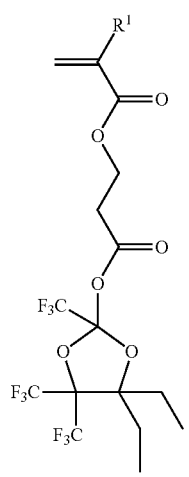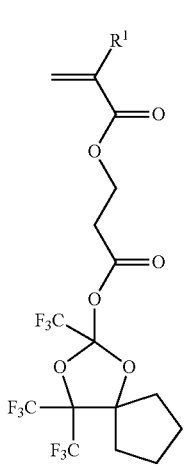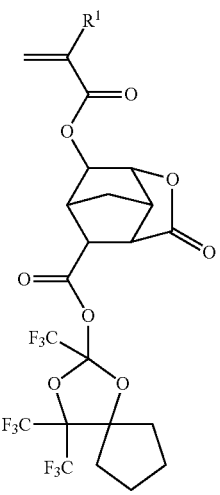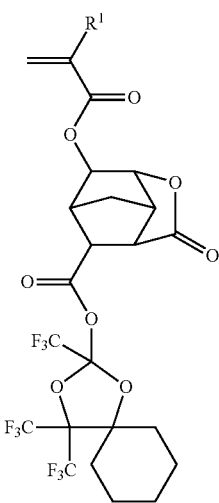
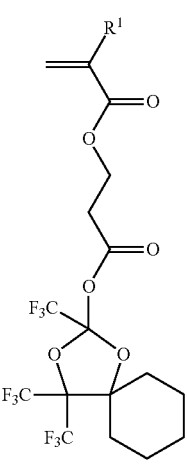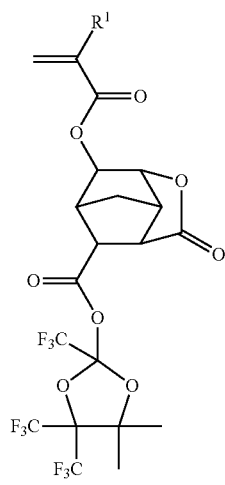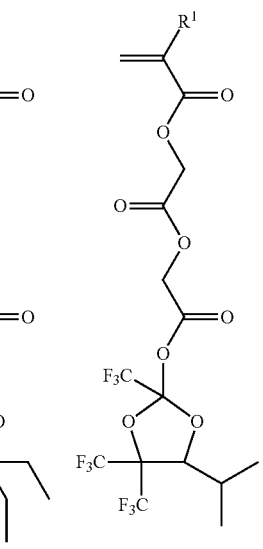

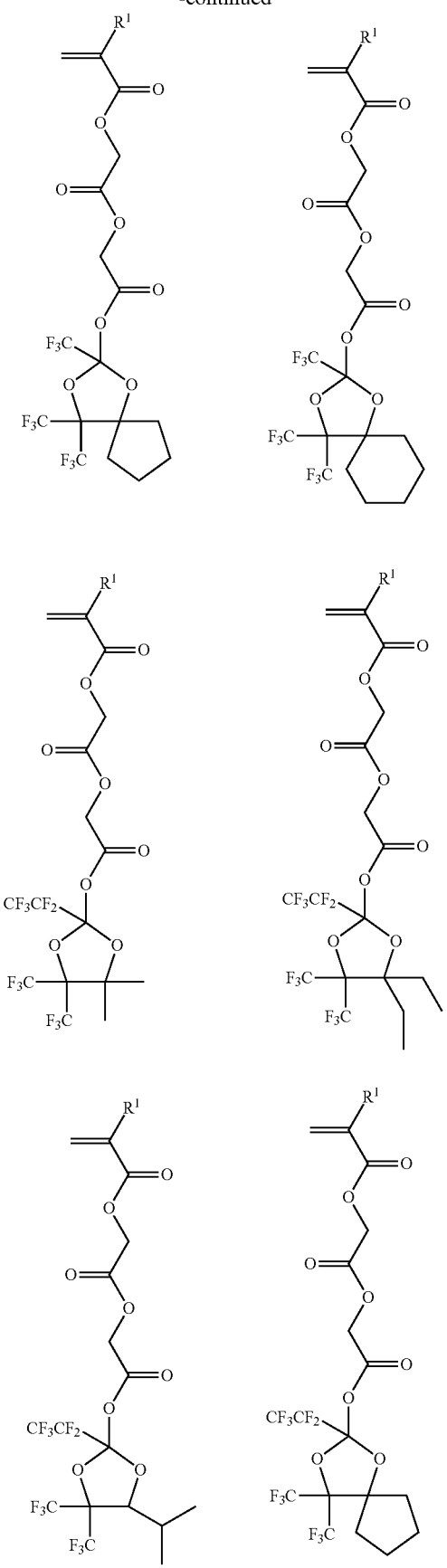
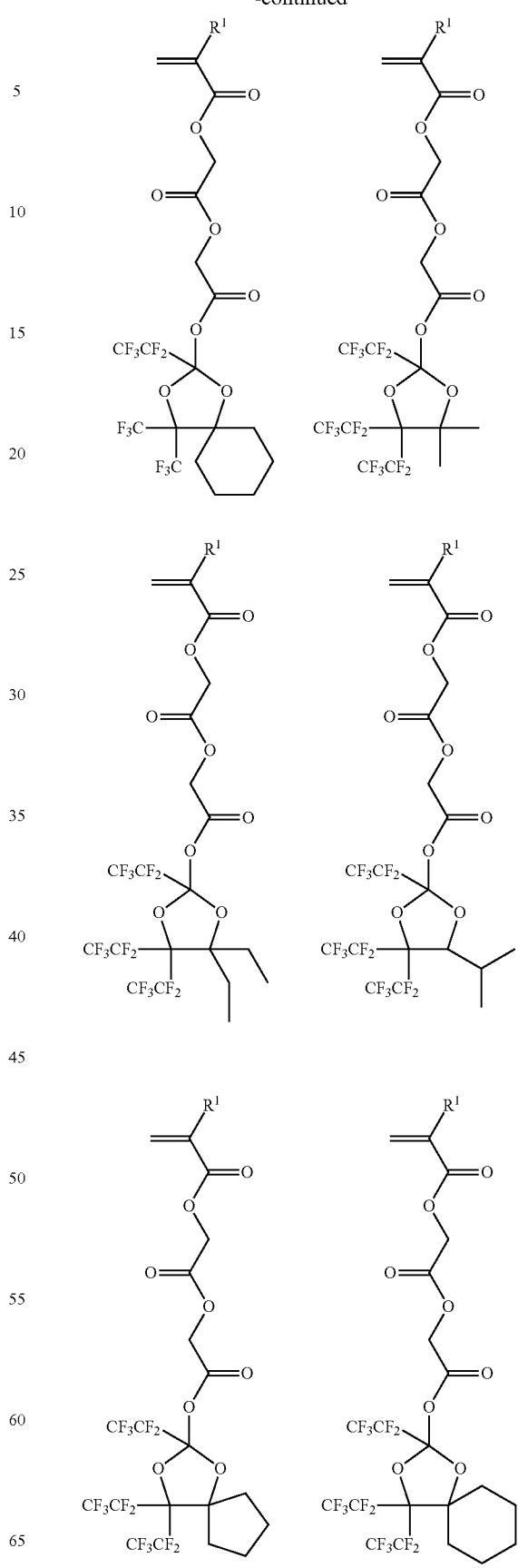

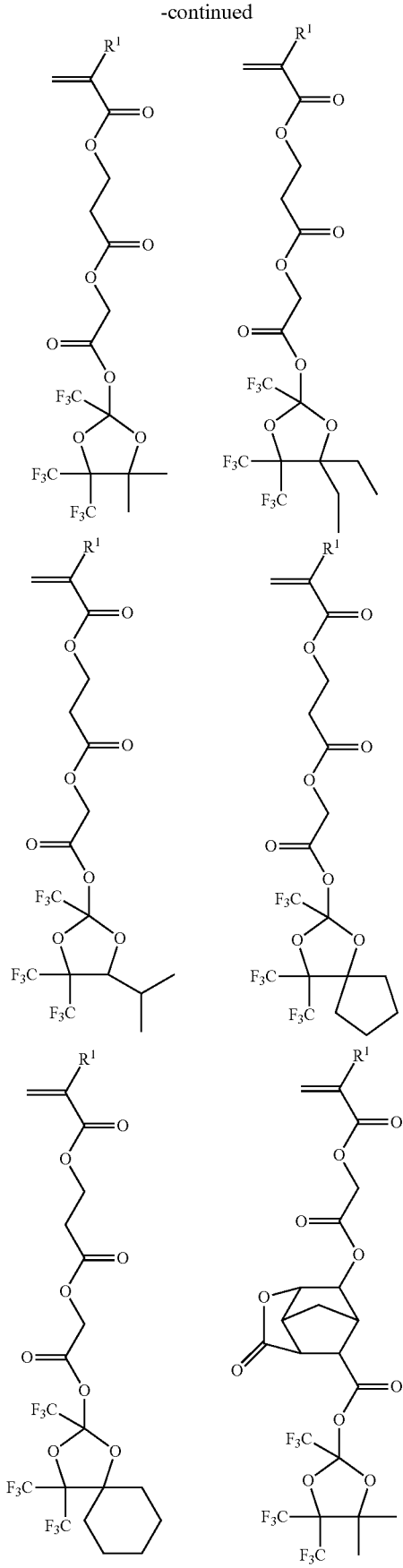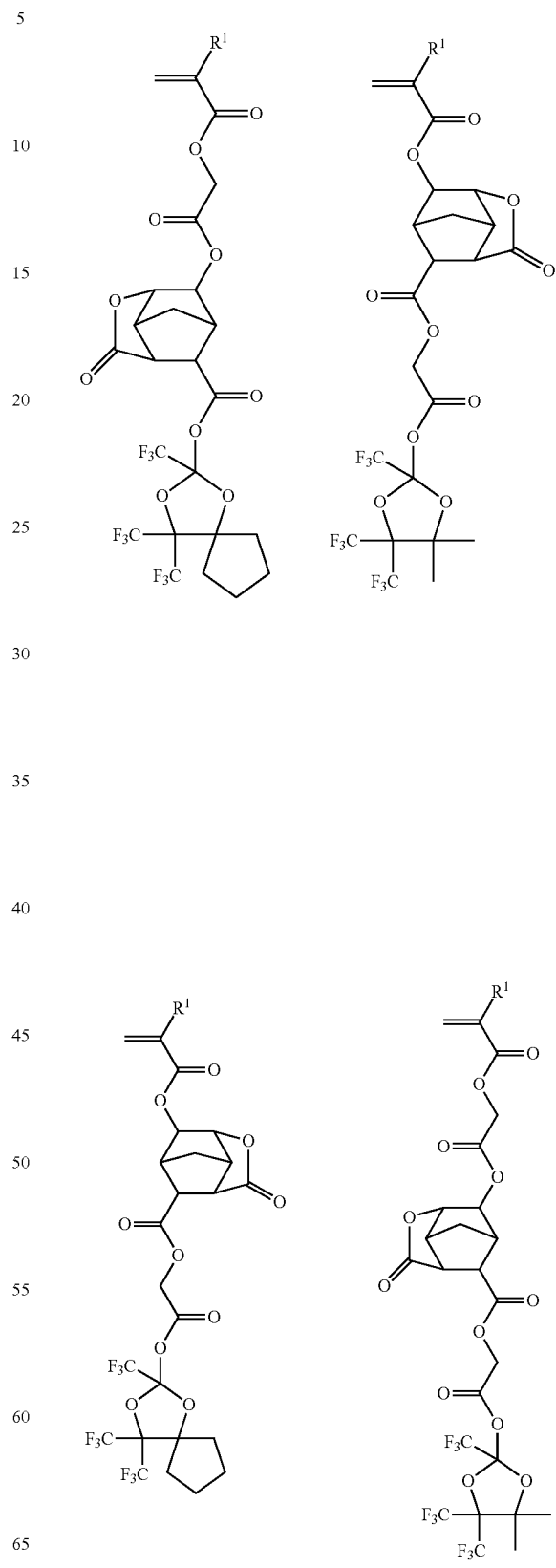

-continued

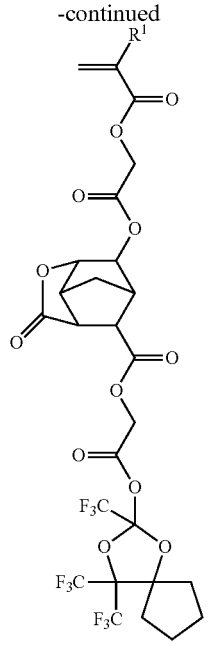

Herein $R^1$ is as defined above.

The fluorinated monomer having formula (1) may be prepared through steps i) and ii) according to the reaction scheme shown below although the preparation method is not limited thereto.

Herein $R^1$ to $R^6$, A and $k^1$ are as defined above. $R^7$ is halogen, hydroxyl or —$OR^9$ wherein $R^9$ is methyl, ethyl or a group of the formula (6):

(6)

wherein $R^4$ is as defined above. $R^8$ is halogen, hydroxyl or —$OR^{10}$ wherein $R^{10}$ is methyl, ethyl or a group of the formula (7):

wherein $R^1$, A and $k^1$ are as defined above.

In the case of $k^1=1$ in formula (1), an alternative process is possible which starts with the reaction product of step i) and includes steps iii) and iv) according to the reaction scheme shown below.

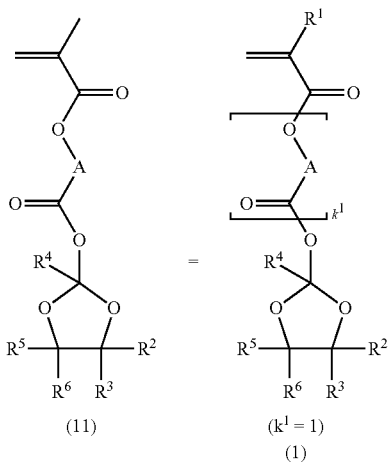

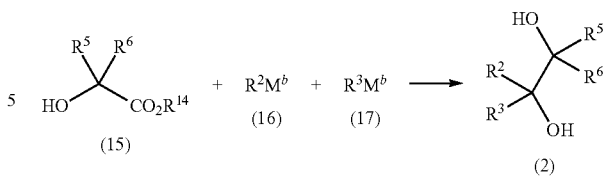

Herein $R^2$ to $R^6$ are as defined above, $R^{14}$ is hydrogen or a straight, branched or cyclic $C_1$-$C_6$ monovalent hydrocarbon group, and $M^b$ is optionally substituted Li, Na, K, MgP, or ZnP wherein P is halogen.

The reaction of step i) may readily proceed in a well-known manner. The preferred acylating agent (3) is an acid chloride of formula (3) wherein $R^7$ is chlorine or an acid anhydride of formula (3) wherein $R^7$ is —$OR^{11}$. In one procedure using an acid chloride, a fluorinated alcohol (2), a corresponding acid chloride (e.g., trifluoroacetic acid chloride or pentafluoropropionic acid chloride), and a base (e.g., triethylamine, pyridine or 4-dimethylaminopyridine) are successively or simultaneously added to a solventless system or to a solvent (e.g., methylene chloride, acetonitrile, diethyl ether, tetrahydrofuran, toluene or hexane), while the reaction system may be cooled or heated as desired. In another procedure using an acid anhydride, a fluorinated alcohol (2), a corresponding acid anhydride (e.g., trifluoroacetic anhydride or pentafluoropropionic anhydride), and a base (e.g., triethylamine, pyridine or 4-dimethylaminopyridine) are successively or simultaneously added to a solvent (e.g., methylene chloride, acetonitrile, diethyl ether, tetrahydrofuran, toluene or hexane), while the reaction system may be cooled or heated as desired. An appropriate amount of acylating agent (3) used, which widely varies with other reaction conditions, is 2.0 to 5.0 moles, is more preferably 2.0 to 3.0 moles per mole of the starting fluorinated alcohol (2). An appropriate amount of the base used, which widely varies with other reaction conditions, is 2.0 to 5.0 moles, more preferably 2.0 to 3.0 moles per mole of the starting fluorinated alcohol (2). The reaction time is determined as appropriate by monitoring the reaction process by gas chromatography (GC) or silica gel thin-layer chromatography (TLC) because it is desirable from the yield aspect to drive the reaction to completion. Usually the reaction time is about 0.5 to about 10 hours. The desired hemi-orthoester (4) may be obtained from the reaction mixture by ordinary aqueous work-up. If necessary, the compound may be purified by standard techniques like distillation and chromatography.

Herein $R^1$ to $R^6$ and A are as defined above, $R^{11}$ is halogen, $R^{12}$ is halogen, hydroxyl, alkoxy or acyloxy, and $M^a$ is Li, Na, K, $Mg_{1/2}$, $Ca_{1/2}$ or substituted or unsubstituted ammonium.

Step i) is reaction of fluorinated alcohol (2) with acylating agent (3) to form cyclic hemi-orthoester compound (4).

In general, when a pinacol of formula (12) is subjected to mono-acylation using acylating agent (3), the equilibrium is biased in favor of a straight mono-acylated compound of formula (13). A cyclic hemi-orthoester (14) is generally impossible to isolate although equilibrium in solution can be observed by NMR spectroscopy or the like.

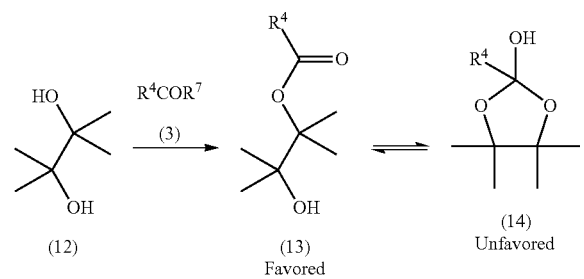

Herein $R^4$ and $R^7$ are as defined above.

In the practice of the invention, when reaction was performed using an alcohol (2) containing fluorinated alkyl as a substituent group on diol, hemi-orthoester (4) could be isolated in a pure and stable way. This is because hemi-orthoester (4) has a high degree of substitution with fluorinated hydrocarbon groups which serve as a strong electron attractive group so that the hemi-orthoester form may become stabilized enough to isolate.

Notably the method for synthesizing fluorinated alcohol (2) which is the starting compound for the synthesis of fluorinated monomer (1) is described in JP-A 2007-204385. For example, a fluorinated alcohol (2) wherein $R^2$ and $R^3$ are monovalent hydrocarbon groups can be synthesized according to the following scheme.

Step ii) is reaction between the hemi-orthoester (4) and an esterifying agent (5) to form a fluorinated monomer (1).

The reaction may readily proceed in a well-known manner. The esterifying agent (5) is preferably an acid chloride of formula (5) wherein $R^8$ is chlorine or a carboxylic acid of formula (5) wherein $R^8$ is hydroxyl. In one procedure using an acid chloride, a hemi-orthoester (4), a corresponding acid chloride (e.g., methacryloyloxyacetic acid chloride), and a base (e.g., triethylamine, pyridine or 4-dimethylaminopyridine) are successively or simultaneously added to a solventless system or to a solvent (e.g., methylene chloride, acetonitrile, toluene or hexane), while the reaction system may be cooled or heated as desired. In another procedure using a carboxylic acid, a hemi-orthoester (4) and a corresponding carboxylic acid (e.g., methacryloyloxyacetic acid) in a solvent (e.g., toluene or hexane) are heated in the presence of an acid catalyst while water formed during reaction may be removed out of the system if desired. Suitable acid catalysts used herein include mineral acids such as hydrochloric acid, sulfuric acid, nitric acid and perchloric acid and organic acids such as p-toluenesulfonic acid and benzenesulfonic acid.

Step iii) is reaction between a hemi-orthoester (4) and an esterifying agent (8) to form a halo ester compound (9) when it is desired to produce a fluorinate monomer of formula (1) wherein $k^1=1$.

The reaction may readily proceed in a well-known manner. The esterifying agent (8) is preferably an acid chloride of formula (8) wherein $R^{12}$ is chlorine or a carboxylic acid of formula (8) wherein $R^{12}$ is hydroxyl. In one procedure using an acid chloride, a hemi-orthoester (4), a corresponding acid chloride (e.g., 2-chloroacetic acid chloride or 4-chlorobutyric acid chloride), and a base (e.g., triethylamine, pyridine or 4-dimethylaminopyridine) are successively or simultaneously added to a solventless system or to a solvent (e.g., methylene chloride, toluene, hexane, diethyl ether, tetrahydrofuran or acetonitrile), while the reaction system may be cooled or heated as desired. In another procedure using a carboxylic acid, a hemi-orthoester (4) and a corresponding carboxylic acid (e.g., 2-chloroacetic acid or 4-chlorobutyric acid) in a solvent (e.g., toluene or hexane) are heated in the presence of an acid catalyst while water formed during reaction may be removed out of the system if desired. Suitable acid catalysts used herein include mineral acids such as hydrochloric acid, sulfuric acid, nitric acid and perchloric acid and organic acids such as p-toluenesulfonic acid and benzenesulfonic acid.

Step iv) is reaction between the halo-ester compound (9) and a carboxylic acid salt (10) to form a monomer (11), i.e., fluorinated monomer (1).

The reaction may be effected by a standard technique. The carboxylic acid salt (10) may be any of commercially available carboxylic acid salts such as metal salts of various carboxylic acids as purchased. Alternatively, the carboxylic acid salt may be formed within the reaction system from a corresponding carboxylic acid such as methacrylic acid or acrylic acid and a base. An appropriate amount of carboxylic acid salt (10) used is 0.5 to 10 moles, more preferably 1.0 to 3.0 moles per mole of the reactant, halo-ester compound (9). If the amount of carboxylic acid salt (10) is less than 0.5 mole, a larger fraction of the reactant may be left unreacted, leading to a substantial drop of percent yield. More than 10 moles of carboxylic acid salt (10) may be uneconomical due to increased material costs and reduced pot yields. In the other embodiment where a carboxylic acid salt is formed within the reaction system from a corresponding carboxylic acid and a base, examples of the base used herein include amines such as ammonia, triethylamine, pyridine, lutidine, collidine, and N,N-dimethylaniline; hydroxides such as sodium hydroxide, potassium hydroxide, and tetramethylammonium hydroxide; carbonates such as potassium carbonate and sodium hydrogen carbonate; metals such as sodium; metal hydrides such as sodium hydride; metal alkoxides such as sodium methoxide and potassium tert-butoxide; organometallics such as butyllithium and ethylmagnesium bromide; and metal amides such as lithium diisopropylamide. One or more bases may be selected from these examples. The amount of the base used is preferably 0.2 to 10 moles, and more preferably 0.5 to 2.0 moles per mole of the corresponding carboxylic acid. If the amount of the base is less than 0.2 mole, a large fraction of the carboxylic acid may become a waste, which is uneconomical. More than 10 moles of the base may lead to a substantial drop of yield due to increased side reactions.

Suitable solvents which can be used in step iv) include hydrocarbons such as toluene, xylene, hexane and heptane; chlorinated solvents such as methylene chloride, chloroform and dichloroethane; ethers such as diethyl ether, tetrahydrofuran, and dibutyl ether; ketones such as acetone and 2-butanone; esters such as ethyl acetate and butyl acetate; nitriles such as acetonitrile; alcohols such as methanol and ethanol; aprotic polar solvents such as N,N-dimethylformamide, N,N-dimethylacetamide, and dimethyl sulfoxide; and water, which may be used alone or in admixture. To the reaction, a phase transfer catalyst such as tetrabutylammonium hydrogensulfate may be added. The amount of phase transfer catalyst added is preferably 0.0001 to 1.0 mole, and more preferably 0.001 to 0.5 mole per mole of the reactant, halo-ester compound (9). Less than 0.0001 mole of the catalyst may fail to achieve the catalytic effect whereas more than 1.0 mole of the catalyst may be uneconomical due to increased material costs.

The temperature of esterifying reaction is preferably in the range of −70° C. to the boiling point of the solvent used. An appropriate temperature may be selected in accordance with other reaction conditions, although it is most often in the range of 0° C. to the boiling point of the solvent used. Since noticeable side reactions occur at higher temperatures, it is important for gaining higher yields that the reaction run at a temperature which is low, but enough to ensure a practically acceptable reaction rate. Also for higher yields, the reaction time is preferably determined by monitoring the reaction process by thin-layer chromatography (TLC) or gas chromatography (GC). Usually the reaction time is about 30 minutes to about 40 hours. The desired fluorinated monomer (1) may be obtained from the reaction mixture by ordinary aqueous work-up. If necessary, the compound may be purified by standard techniques like distillation, recrystallization and chromatography.

Additive Polymer

A second embodiment provides a polymer useful as an additive to a resist composition, and specifically a polymer or high-molecular-weight compound comprising recurring units represented by the general formula (1a). For convenience of description, the polymer comprising recurring units of formula (1a) is referred as "polymer P1," hereinafter.

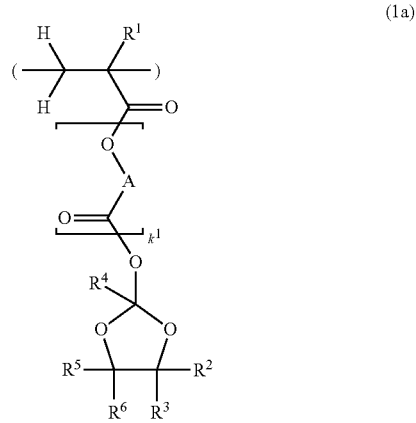

Herein $R^1$ to $R^6$, A and $k^1$ are as defined above.

Polymer P1 is characterized in that the recurring units of formula (1a) each contain a plurality of fluorine atoms. Once polymer P1 is added to a resist composition, polymer P1 itself functions as a surfactant to provide a distribution at the time when a resist film is formed, that polymer P1 is segregated at the resist film surface.

In general, fluorinated polymers exert excellent functions of water repellency and water slip. When polymer P1 is used as a resist additive, it is possible to form a resist film having a surface exerting excellent water repellency and water slip at the same time as its formation. An effect equivalent to the use of resist protective coating material is expectable. This approach is also advantageous in cost because it eliminates the steps of forming and removing a resist protective coating.

Since the recurring unit of formula (1a) contains a fluorinated ester susceptible to alkaline hydrolysis, the unit is readily hydrolyzed in alkaline developer to create a carboxylic acid unit (1aa) as illustrated in the reaction scheme below. Then, when polymer P1 is used as a resist additive, the surface of a resist film after alkaline development becomes more hydrophilic and the surface contact angle thereof is significantly reduced. As a result, the occurrence of blob defects may be inhibited.

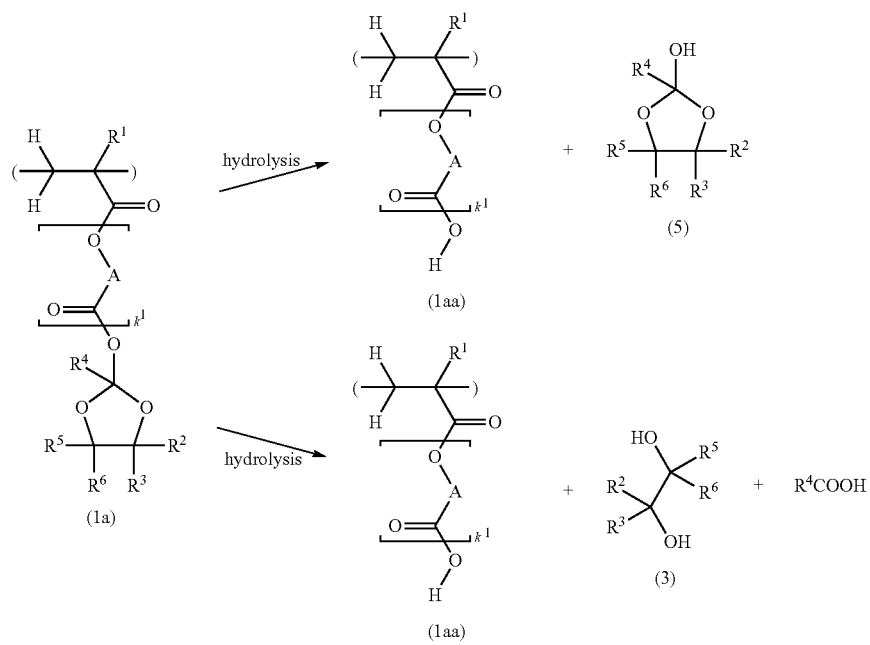

Herein $R^1$ to $R^6$, A and $k^1$ are as defined above.

Polymer P1 may be further improved in water repellency, water slip, alkaline dissolution, and contact angle after development, by incorporating recurring units of one or more type selected from the general formulae (2a) to (2i) in addition to the recurring units of formula (1a).

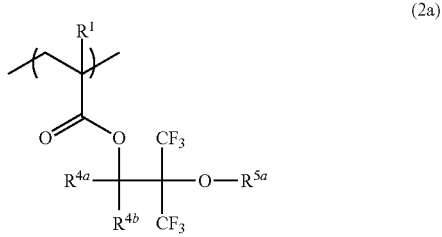
(2a)

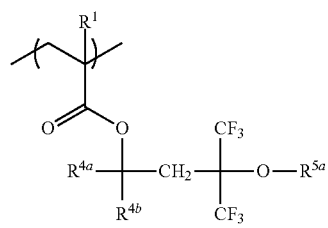
(2b)

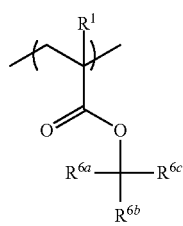
(2c)

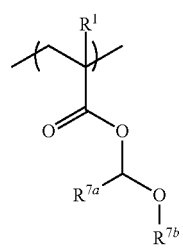
(2d)

(2e) 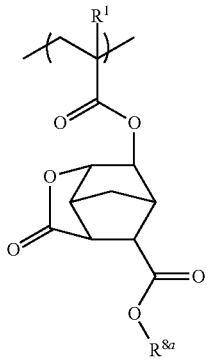

(2f) 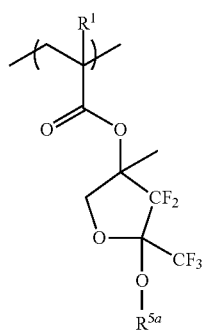

(2g) 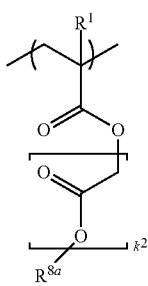

(2h) 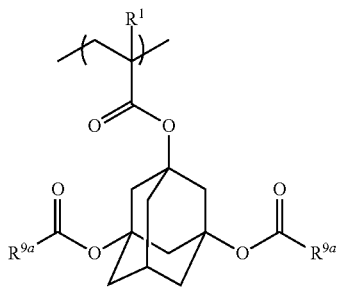

(2i) 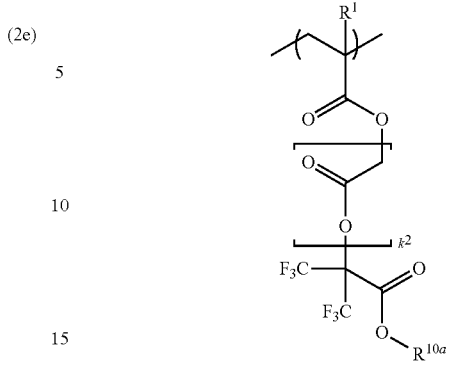

Herein $R^1$ is as defined above. $R^{4a}$ and $R^{4b}$ each are hydrogen or a straight, branched or cyclic $C_1$-$C_{15}$ monovalent hydrocarbon group, or $R^{4a}$ and $R^{4b}$ may bond together to form a non-aromatic ring of 3 to 8 carbon atoms with the carbon atom to which they are attached. $R^{5a}$ is hydrogen, a straight, branched or cyclic $C_1$-$C_{15}$ monovalent hydrocarbon or fluorinated hydrocarbon group, or an acid labile group, and in the case of hydrocarbon group, any constituent moiety —$CH_2$— may be replaced by —O— or —C(=O)—. $R^{6a}$, $R^{6b}$ and $R^{6c}$ each are hydrogen, or a straight, branched or cyclic $C_1$-$C_{15}$ monovalent hydrocarbon group, a pair of $R^{6a}$ and $R^{6b}$, $R^{6a}$ and $R^{6c}$, or $R^{6b}$ and $R^{6c}$ may bond together to form a non-aromatic ring of 3 to 8 carbon atoms with the carbon atom to which they are attached. $R^{7a}$ is hydrogen, or a straight, branched or cyclic $C_1$-$C_{15}$ monovalent hydrocarbon group, $R^{7b}$ is a straight, branched or cyclic $C_1$-$C_{15}$ monovalent hydrocarbon group, a pair of $R^{7a}$ and $R^{7b}$ may bond together to form a non-aromatic ring of 3 to 8 carbon atoms with the carbon and oxygen atoms to which they are attached. $R^{8a}$ is a straight, branched or cyclic $C_1$-$C_{15}$ monovalent fluorinated hydrocarbon group. $R^{9a}$ is a straight, branched or cyclic $C_1$-$C_{10}$ monovalent fluorinated hydrocarbon group. $R^{10a}$ is a straight, branched or cyclic $C_1$-$C_{15}$ monovalent hydrocarbon group which may contain halogen or oxygen. Subscript $k^2$ is 0 or 1.

In formulae (2a) to (2i), the straight, branched or cyclic $C_1$-$C_{15}$ monovalent hydrocarbon groups represented by $R^{4a}$, $R^{4b}$, $R^{5a}$, $R^{6a}$, $R^{6b}$, $R^{6c}$, $R^{7a}$, and $R^{7b}$ are preferably alkyl groups, examples of which include methyl, ethyl, n-propyl, isopropyl, n-butyl, sec-butyl, tert-butyl, tert-amyl, n-pentyl, n-hexyl, n-heptyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl, cyclohexylbutyl, and adamantyl. A pair of $R^{4a}$ and $R^{4b}$, $R^{6a}$ and $R^{6b}$, $R^{6a}$ and $R^{6c}$, $R^{6b}$ and $R^{6c}$, or $R^{7a}$ and $R^{7b}$ may bond together to form a non-aromatic ring of 3 to 8 carbon atoms with the carbon atom (or carbon and oxygen atoms) to which they are attached. In this case, these groups each are an alkylene group, examples of which are the foregoing alkyl groups with one hydrogen atom eliminated, and exemplary rings include cyclopentyl and cyclohexyl.

The straight, branched or cyclic $C_1$-$C_{15}$ monovalent fluorinated hydrocarbon groups represented by $R^{5a}$ and $R^{8a}$ are preferably fluoroalkyl groups, which are typically the foregoing alkyl groups in which some or all hydrogen atoms are substituted by fluorine atoms. Examples include trifluoromethyl, 2,2,2-trifluoroethyl, 3,3,3-trifluoro-1-propyl, 3,3,3-trifluoro-2-propyl, 2,2,3-tetrafluoropropyl, 1,1,1,3,3,3-hexafluoroisopropyl, 2,2,3,3,4,4,4-heptafluorobutyl, 2,2,3,3,4,4,5,5-octafluoropentyl, 2,2,3,3,4,4,5,5,6,6,7,7- dodecafluoroheptyl, 2-(perfluorobutyl)ethyl, 2-(perfluorohexyl)ethyl, 2-(perfluorooctyl)ethyl, 2-(perfluorodecyl)ethyl, and 3,3,4,4,5,5,6,6,6-nonafluorohexyl. The straight, branched or cyclic $C_1$-$C_{10}$ monovalent fluorinated hydrocarbon groups represented by $R^{9a}$ are also preferably fluoroalkyl groups, examples of which include trifluoromethyl, 2,2,2-trifluoroethyl, 3,3,3-trifluoro-1-propyl, 3,3,3-trifluoro-2-propyl, 2,2,3,3-tetrafluoropropyl, 1,1,1,3,3,3-hexafluoroisopropyl, 2,2,3,3,4,4,4-heptafluorobutyl, 2,2,3,3,4,4,5,5-octafluoropentyl, 2,2,3,3,4,4,5,5,6,6,7,7-dodecafluoroheptyl, 2-(perfluorobutyl)ethyl, 2-(perfluorohexyl)ethyl, 2-(perfluorooctyl)ethyl, and 3,3,4,4,5,5,6,6,6-nonafluorohexyl.

The acid labile group represented by $R^{5a}$ may be selected from a variety of such groups. Examples of the acid labile group are groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

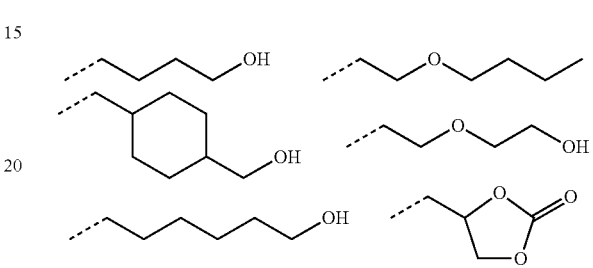

Herein $R^{L01}$ and $R^{L02}$ are hydrogen or straight, branched or cyclic alkyl groups of 1 to 18 carbon atoms, preferably 1 to 10 carbon atoms. $R^{L03}$ is a monovalent hydrocarbon group of 1 to 18 carbon atoms, preferably 1 to 10 carbon atoms, which may contain a heteroatom such as oxygen, examples of which include unsubstituted straight, branched or cyclic alkyl groups and substituted forms of such alkyl groups in which some hydrogen atoms are replaced by hydroxyl, alkoxy, oxo, amino, alkylamino or the like. $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). $R^{L05}$ is an optionally substituted, straight, branched or cyclic $C_1$-$C_{10}$ alkyl group or an optionally substituted $C_6$-$C_{20}$ aryl group. $R^{L06}$ is an optionally substituted, straight, branched or cyclic $C_1$-$C_{10}$ alkyl group or an optionally substituted $C_6$-$C_{20}$ aryl group. $R^{L07}$ to $R^{L16}$ independently represent hydrogen or an optionally substituted monovalent hydrocarbon group of 1 to 15 carbon atoms. Letter y is an integer of 0 to 6, m is equal to 0 or 1, n is equal to 0, 1, 2 or 3, and 2m+n is equal to 2 or 3. The broken line denotes a valence bond.

In formula (L1), exemplary groups of $R^{L01}$ and $R^{L02}$ include methyl, ethyl, propyl, isopropyl, n-butyl, sec-butyl, tert-butyl, cyclopentyl, cyclohexyl, 2-ethylhexyl, n-octyl, and adamantyl. $R^{L03}$ is a monovalent hydrocarbon group of 1 to 18 carbon atoms, preferably 1 to 10 carbon atoms, which may contain a heteroatom such as oxygen, examples of which include unsubstituted straight, branched or cyclic alkyl groups and substituted forms of such alkyl groups in which some hydrogen atoms are replaced by hydroxyl, alkoxy, oxo, amino, alkylamino or the like. Illustrative examples of the straight, branched or cyclic alkyl groups are as exemplified above for $R^{L01}$ and $R^{L02}$, and examples of the substituted alkyl groups are as shown below.

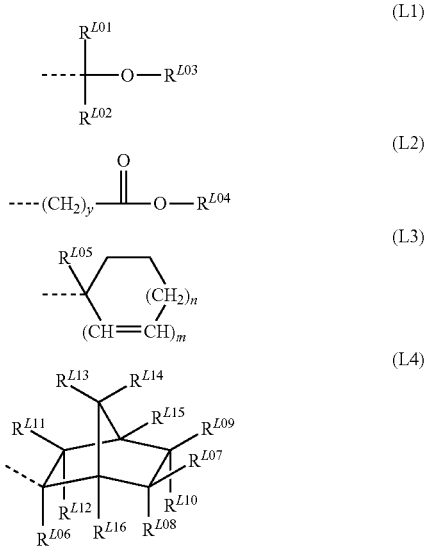

A pair of $R^{L01}$ and $L^{L02}$, $R^{L01}$ and $R^{L03}$, or $R^{L02}$ and $R^{L03}$ may bond together to form a ring with carbon and oxygen atoms to which they are attached. Each of ring-forming $R^{L01}$, $R^{L02}$ and $R^{L03}$ is a straight or branched alkylene group of 1 to 18 carbon atoms, preferably 1 to 10 carbon atoms when they form a ring.

In formula (L2), exemplary tertiary alkyl groups of $R^{L04}$ are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, 2-ethyl-2-adamantyl, and the like. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl.

In formula (L3), examples of the optionally substituted alkyl groups of $R^{L05}$ include straight, branched or cyclic alkyl groups such as methyl, ethyl, propyl, isopropyl, n-butyl, sec-butyl, tert-butyl, tert-amyl, n-pentyl, n-hexyl, cyclopentyl, cyclohexyl, and bicyclo[2.2.1]heptyl, and substituted forms of such groups in which some hydrogen atoms are replaced by hydroxyl, alkoxy, carboxy, alkoxycarbonyl, oxo, amino, alkylamino, cyano, mercapto, alkylthio, sulfo or other radicals or in which a methylene moiety is replaced by oxygen or sulfur. Examples of optionally substituted $C_6$-$C_{20}$ aryl groups include phenyl, methylphenyl, naphthyl, anthryl, phenanthryl, and pyrenyl.

In formula (L4), examples of optionally substituted, straight, branched or cyclic $C_1$-$C_{10}$ alkyl groups and optionally substituted $C_6$-$C_{20}$ aryl groups of $R^{L06}$ are the same as exemplified for $R^{L05}$. Exemplary $C_1$-$C_{15}$ monovalent hydrocarbon groups of $R^{L07}$ to $R^{L16}$ are straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of these groups in which some hydrogen atoms are replaced by hydroxyl, alkoxy, carboxy, alkoxycarbonyl, oxo, amino, alkylamino, cyano, mercapto, alkylthio, sulfo or other radicals. Alternatively, two of $R^{L07}$ to $R^{L16}$ may bond together to form a ring with the carbon atom(s) to which they are attached (for example, a pair of $R^{L07}$ and $R^{L08}$, $R^{L07}$ and $R^{L09}$, $R^{L08}$ and $R^{L10}$, $R^{L09}$ and $R^{L11}$ and $R^{L12}$, $R^{L13}$ and $R^{L14}$, or a similar pair form a ring). Each of $R^{L07}$ to $R^{L16}$ represents a divalent $C_1$-$C_{15}$ hydrocarbon group (typically alkylene) when they form a ring, examples of which are those exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, or a similar pair).

Of the acid labile groups of formula (L1), the straight and branched ones are exemplified by the following groups.

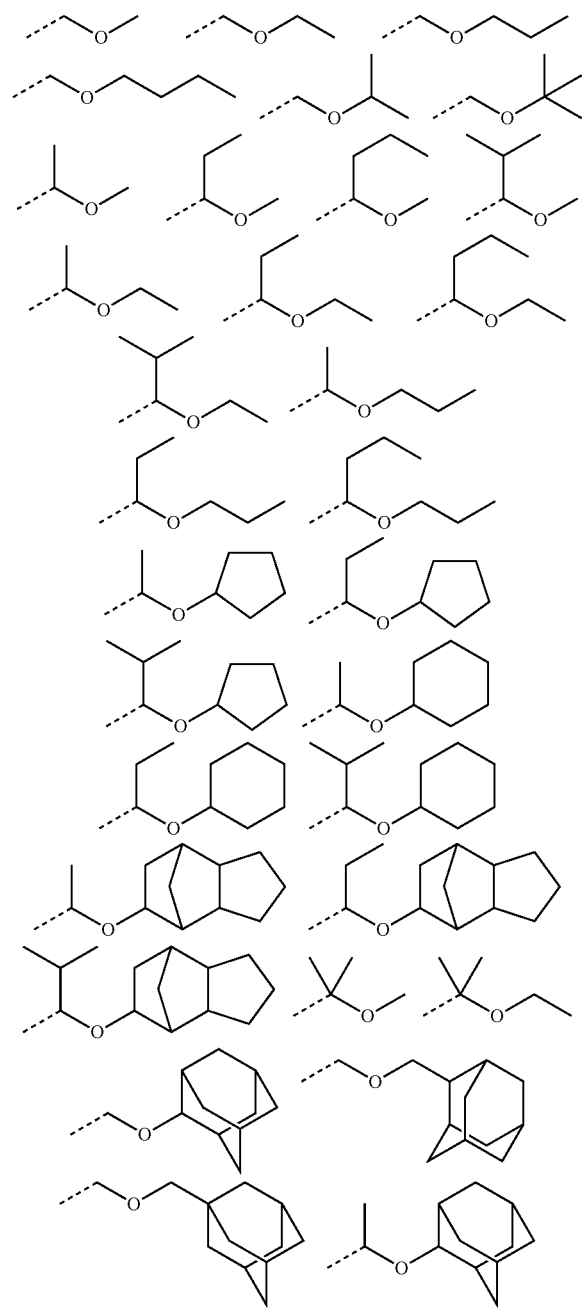

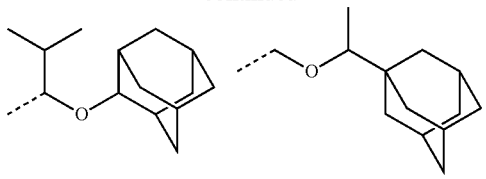

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-(bicyclo[2.2.1]heptan-2-yl)cyclopentyl, 1-(7-oxabicyclo[2.2.1]heptan-2-yl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl.

Of the acid labile groups of formula (L4), those groups of the following formulae (L4-1) to (L4-4) are preferred.

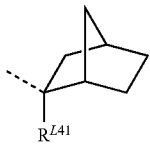
(L4-1)

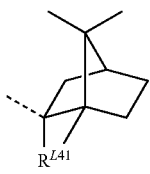
(L4-2)

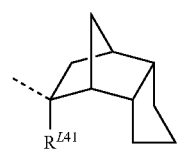
(L4-3)

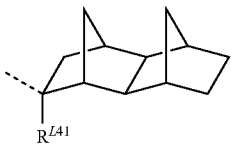
(L4-4)

In formulas (L4-1) to (L4-4), the broken line denotes a bonding site and direction. $R^{L41}$ is each independently a monovalent hydrocarbon group, typically a straight, branched or cyclic $C_1$-$C_{10}$ alkyl group, such as methyl, ethyl, propyl, isopropyl, n-butyl, sec-butyl, tert-butyl, tert-amyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two selected from groups having the following general formulas (L4-3-1) and (L4-3-2).

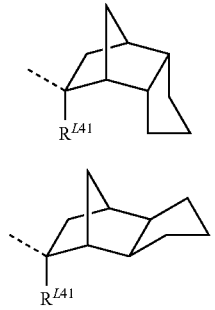

(L4-3-1)

(L4-3-2)

Note that $R^{L41}$ is as defined above.

Similarly, the general formula (L4-4) represents one or a mixture of two or more selected from groups having the following general formulas (L4-4-1) to (L4-4-4).

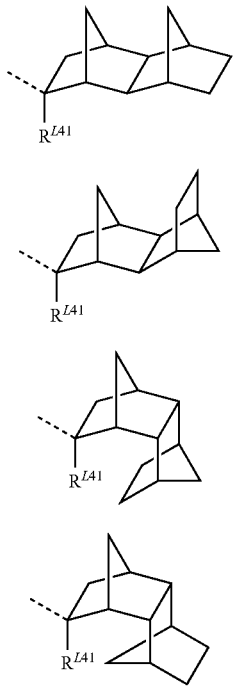

(L4-4-1)

(L4-4-2)

(L4-4-3)

(L4-4-4)

Note that $R^{L41}$ is as defined above.

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1]heptane ring, which ensures high reactivity for acid catalyzed elimination reaction (see JP-A 2000-336121). In preparing these monomers having a tertiary exo-alkyl group of bicyclo[2.2.1]heptane structure as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

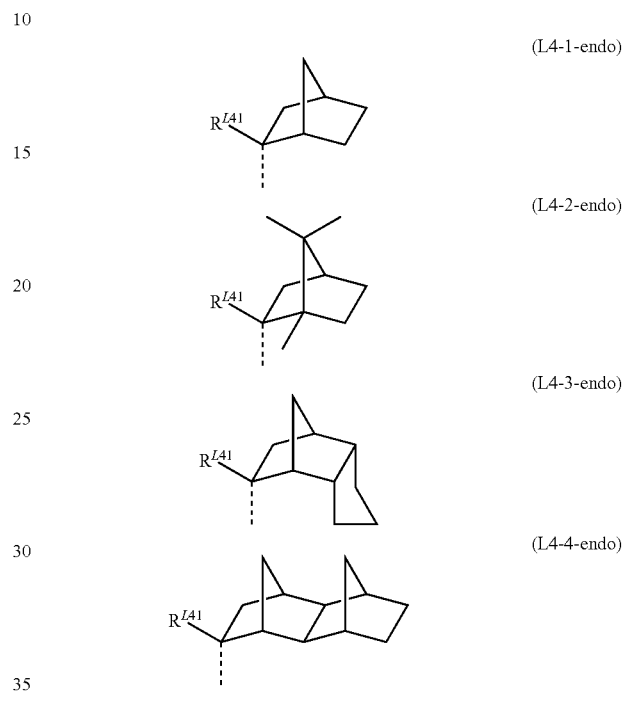

(L4-1-endo)

(L4-2-endo)

(L4-3-endo)

(L4-4-endo)

Note that $R^{L41}$ is as defined above.

Illustrative examples of the acid labile group of formula (L4) are given below.

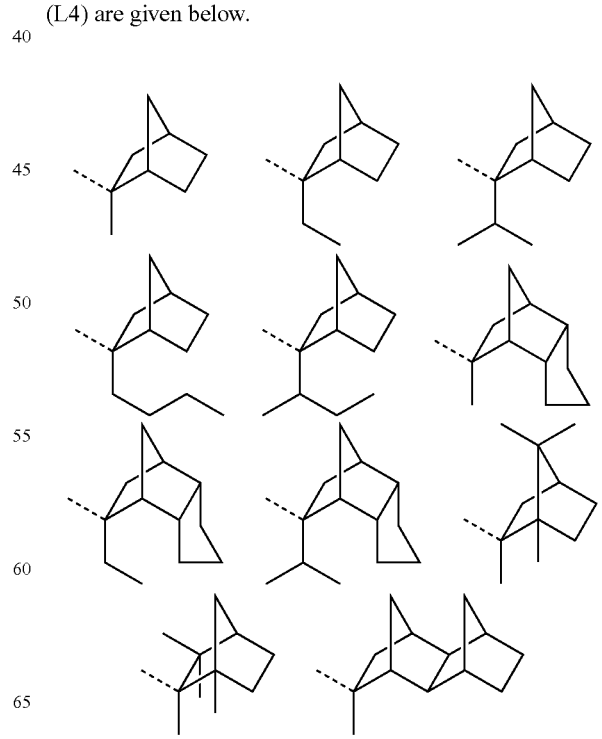

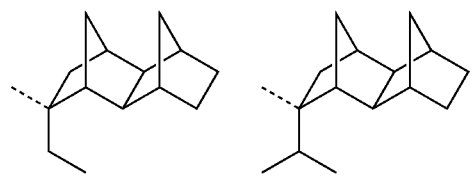
Examples of the tertiary $C_4$-$C_{20}$ alkyl groups, trialkylsilyl groups in which each alkyl moiety has 1 to 6 carbon atoms, and $C_4$-$C_{20}$ oxoalkyl groups, represented by $R^{5a}$, are as exemplified for $R^{LO4}$ and the like.
Illustrative examples of the recurring units of formulae (2a) to (2i) are given below, but not limited thereto.
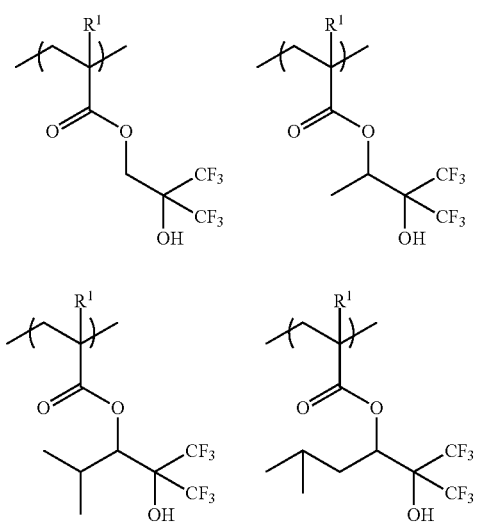
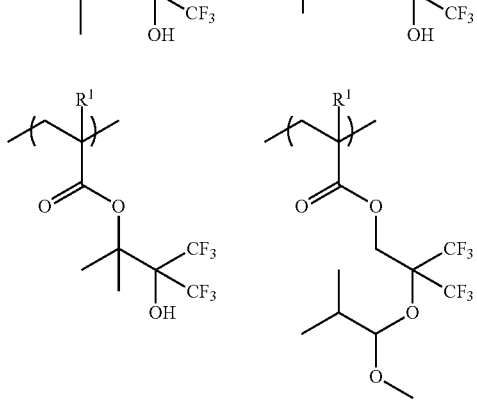
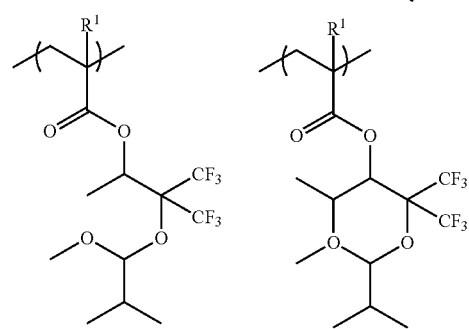
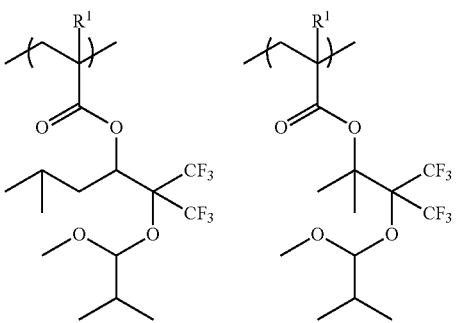
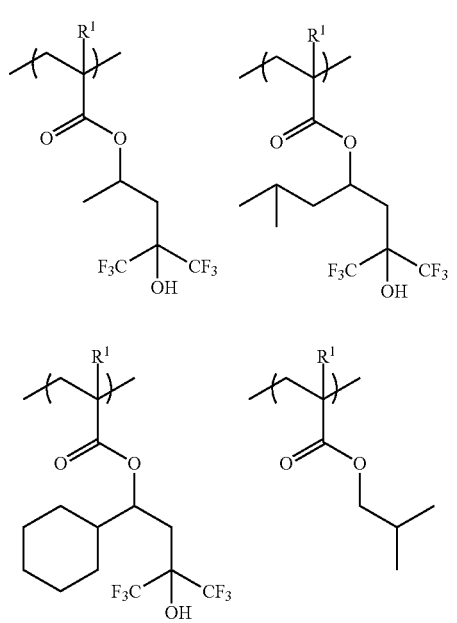
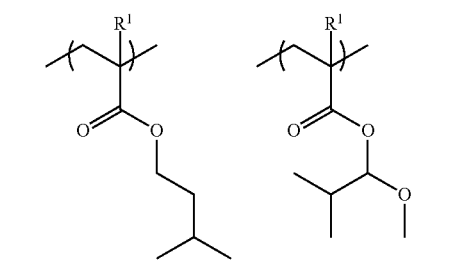
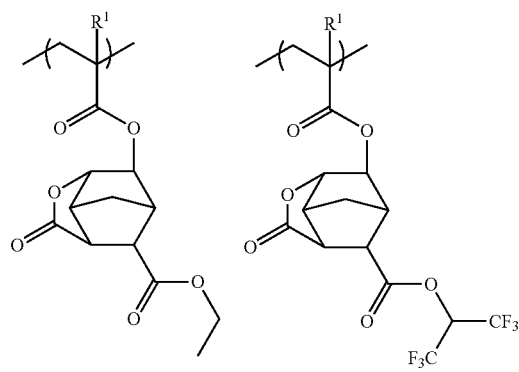

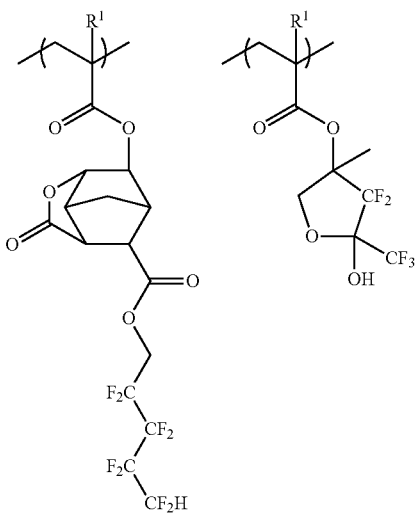
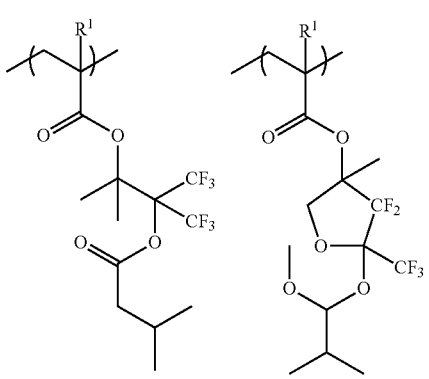
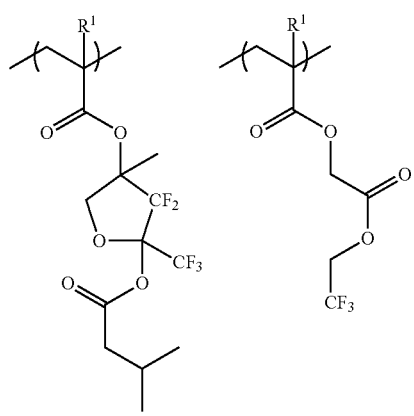
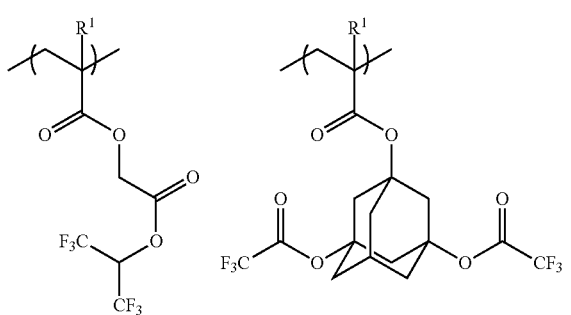
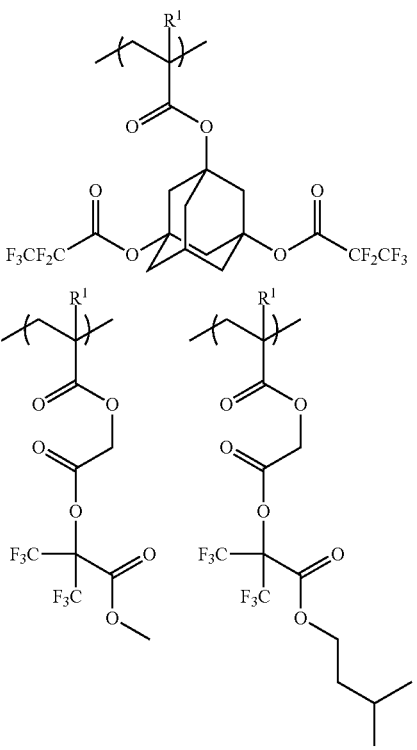

Herein $R^1$ is as defined above.

Although polymer P1 comprising recurring units of formula (1a) in combination with recurring units of formulae (2a) to (2i) exerts satisfactory performance, recurring units of one or more types selected from formulae (3a) to (3e), (4a) to (4e), (5a) to (5c), and (6a) to (6c) may be further incorporated therein for the purposes of imparting further water repellency and water slip, and controlling alkaline solubility and developer affinity.

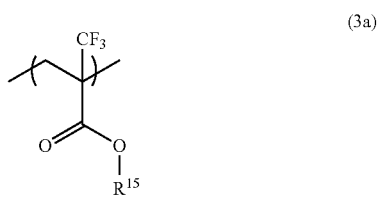

(3a)

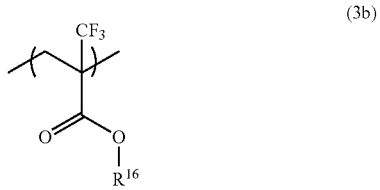

(3b)

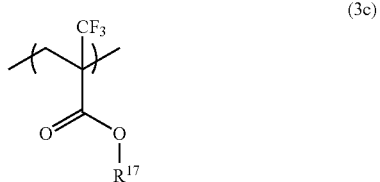

(3c)

-continued

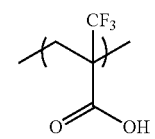 (3d)

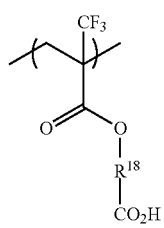 (3e)

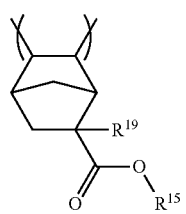 (4a)

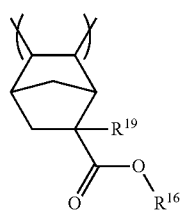 (4b)

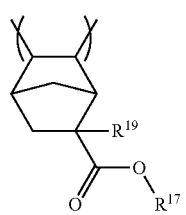 (4c)

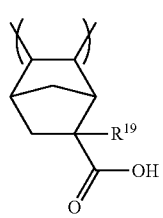 (4d)

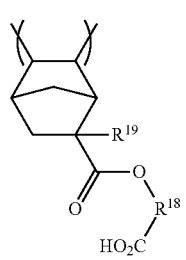 (4e)

-continued

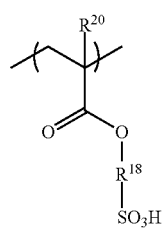 (5a)

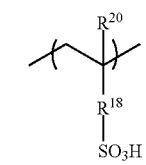 (5b)

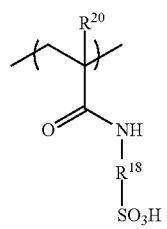 (5c)

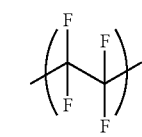 (6a)

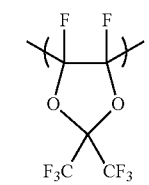 (6b)

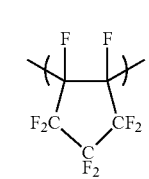 (6c)

Herein $R^{15}$ is a $C_1$-$C_{15}$ monovalent hydrocarbon or fluorinated hydrocarbon group, $R^{15}$ is an adhesive group, $R^{17}$ is an acid labile group, $R^{19}$ is a single bond or a $C_1$-$C_{15}$ divalent organic group, typically alkylene, and $R^{19}$ and $R^{20a}$ each are hydrogen, methyl or trifluoromethyl.

Examples of the $C_1$-$C_{15}$ monovalent hydrocarbon or fluorinated hydrocarbon group represented by $R^{15}$ are the same as illustrated for $R^{5a}$ and $R^{8a}$.

The adhesive group represented by $R^{16}$ may be selected from a variety of such groups, typically those groups shown below.

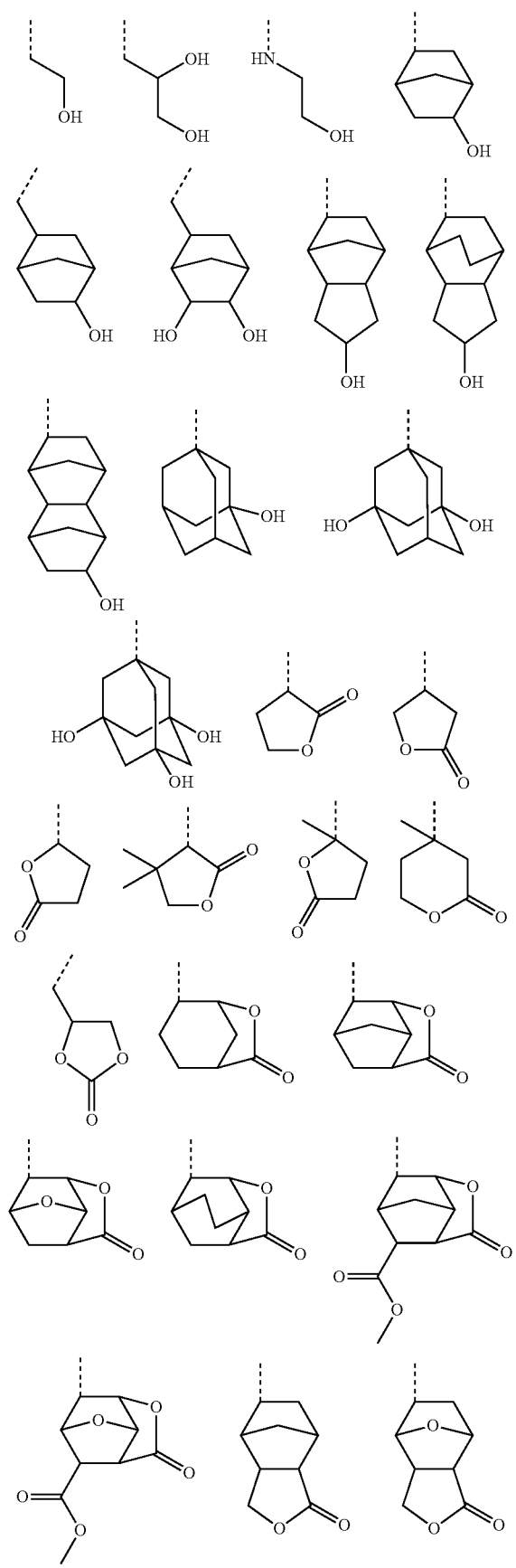
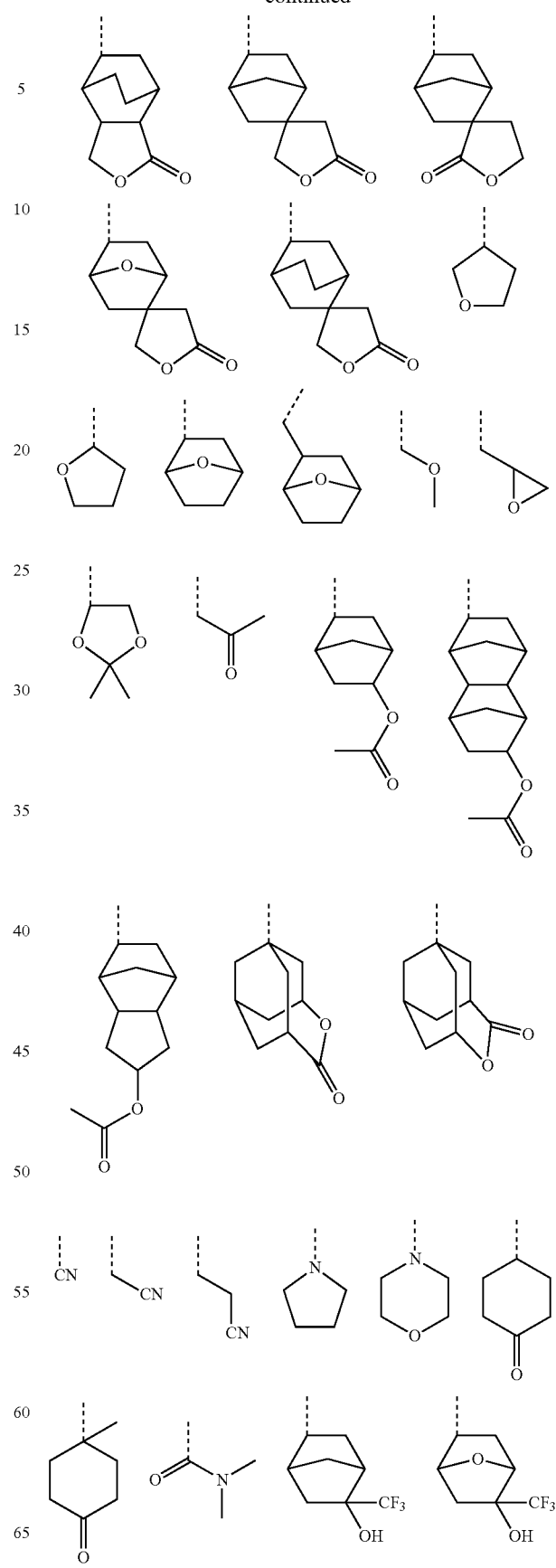

-continued

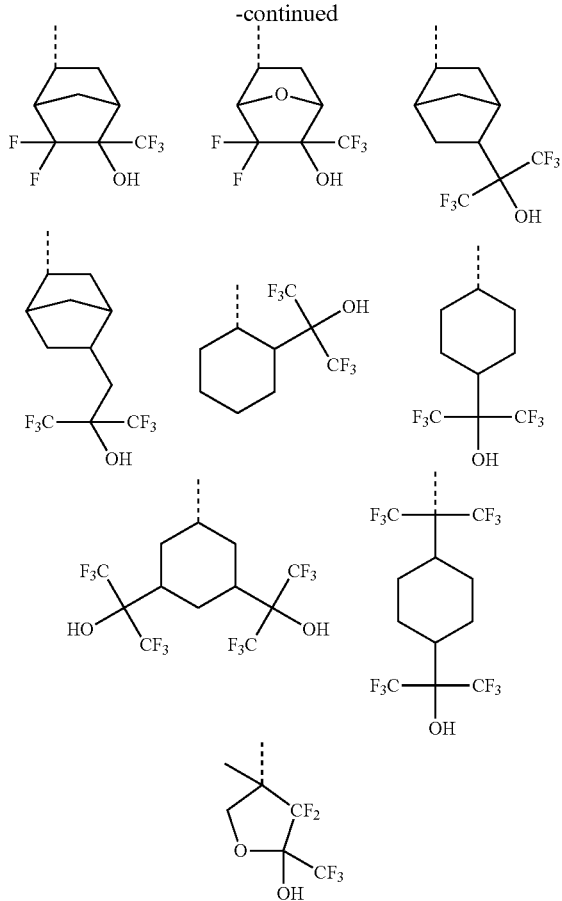

Herein, the broken line designates a valence bond.

The acid labile group represented by $R^{17}$ may be selected from those groups illustrated for Rya.

Suitable $C_1$-$C_{15}$ divalent organic groups represented by $R^{18}$ include the above-illustrated monovalent hydrocarbon groups with one hydrogen atom eliminated (e.g., methylene and ethylene) and groups of the following formulae.

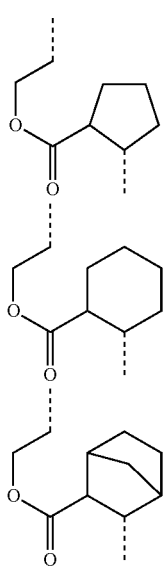

-continued

Herein, the broken line designates a valence bond.

Polymer Synthesis

The polymer P1 used herein may be synthesized by general polymerization processes including radical polymerizataion using initiators such as 2,2'-azobisisobutyronitrile (AIBN), and ionic (or anionic) polymerization using alkyllithium or the like. The polymerization may be carried out by a standard technique. Preferably polymer P1 is prepared by radical polymerization while the polymerization conditions may be determined in accordance with the type and amount of initiator, temperature, pressure, concentration, solvent, additives, and the like.

Examples of the radical polymerization initiator used herein include azo compounds such as 2,2'-azobisisobutyronitrile (AIBN), 2,2'-azobis(4-methoxy-2,4-dimethylvaleronitrile), 2,2'-azobis(2,4-dimethylvaleronitrile), 2,2'-azobis (2,4,4-trimethylpentane), and dimethyl 2,2'-azobis (isobutyrate); peroxides such as tert-butylperoxypivalate, lauroyl peroxide, benzoyl peroxide, and tert-butylperoxylaurate; water-soluble polymerization initiators such as potassium persulfate; and redox initiators comprising a peroxide (e.g., potassium persulfate or hydrogen peroxide) combined with a reducing agent (e.g., sodium sulfite). Although the amount of polymerization initiator used may vary with its type and other polymerization conditions, it is generally used in an amount of 0.001 to 10 mol %, and preferably 0.01 to 6 mol % based on the total moles of monomers to be polymerized.

During the synthesis of polymer μl, any known chain transfer agent such as dodecyl mercaptan or 2-mercaptoethanol may be added for molecular weight control purpose. The amount of chain transfer agent added is preferably 0.01 to 10 mol % based on the total moles of monomers to be polymerized.

Polymer P1 may be synthesized by combining suitable monomers selected from polymerizable monomers corresponding to recurring units of formulae (1a), (2a) to (2i), (3a) to (3e), (4a) to (4e), (5a) to (5c), and (6a) to (6c), adding an initiator and chain transfer agent to the monomer mixture, and effecting polymerization.

In polymer P1 wherein U1 stands for a total molar number of a monomer or monomers corresponding to units of formula (1a), U2 stands for a total molar number of a monomer or monomers corresponding to units of formulae (2a) to (2i), and U3 stands for a total molar number of a monomer or monomers corresponding to units of formulae (3a) to (3e), (4a) to (4e), (5a) to (5c), and (6a) to (6c), with the proviso that U1+U2+U3=U (=100 mol %), values of U1, U2, and U3 are preferably determined so as to meet:

0<U1/U<1, more preferably 0.1≤U1/U≤0.8, even more preferably 0.1≤U1/U≤0.7, $0 \leq U2/U < 1$, more preferably $0.1 \leq U2/U \leq 0.8$, even more preferably $0.2 \leq U2/U \leq 0.8$, and $0 \leq U3/U < 1$, more preferably $0 \leq U3/U \leq 0.4$, even more preferably $0 \leq U3/U \leq 0.2$.

In conducting polymerization, a solvent may be used if necessary. Any solvent may be used as long as it does not interfere with the desired polymerization reaction. Typical solvents used herein include esters such as ethyl acetate, n-butyl acetate, and γ-butyrolactone; ketones such as acetone, methyl ethyl ketone, and methyl isobutyl ketone; aliphatic or aromatic hydrocarbons such as toluene, xylene and cyclohexane; alcohols such as isopropyl alcohol and ethylene glycol monomethyl ether; and ether solvents such as diethyl ether, dioxane, and tetrahydrofuran, which may be used alone or in admixture. Although the amount of solvent used may vary with the desired degree of polymerization (or molecular weight), the amount of initiator added, and other polymerization conditions such as polymerization temperature, it is generally used in such an amount as to provide a concentration of 0.1 to 95% by weight, preferably 5 to 90% by weight of monomers to be polymerized.

Although the temperature of the polymerization reaction may vary with the identity of polymerization initiator or the boiling point of solvent, it is preferably in the range of 20 to 200° C., and more preferably 50 to 140° C. Any desired reactor or vessel may be used for the polymerization reaction.

From the solution or dispersion of the polymer thus synthesized, the organic solvent or water serving as the reaction medium is removed by any well-known techniques. Suitable techniques include, for example, re-precipitation followed by filtration, and heat distillation under vacuum.

Desirably polymer P1 has a weight average molecular weight (Mw) of 1,000 to 500,000, and especially 2,000 to 30,000, as determined in tetrahydrofuran solvent by gel permeation chromatography (GPC) using polystyrene standards. This is because a polymer with too low a Mw may be dissolvable in water whereas too high a Mw may lead to a decline of alkali solubility or cause coating defectives during spin coating.

In polymer P1, $R^{5a}$ in formula (2a), (2b) and (2f) and $R^{17}$ in formula (3c) and (4c) may be introduced by post-protection reaction. Specifically, a polymer may be synthesized by polymerizing a monomer wherein $R^{5a}$ and $R^{17}$ are hydrogen to synthesize an intermediate polymer, then effecting post-protection reaction to substitute $R^{5a}$ and $R^{17}$ for some or all hydroxyl groups in the intermediate polymer.

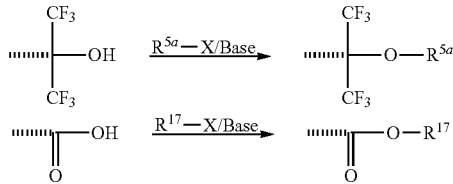

Herein $R^{5a}$ and $R^{17}$ are as defined above, and X is chlorine, bromine or iodine.

The desired (post-protected) polymer is obtainable through post-protection reaction by reacting the intermediate polymer with a base in an amount of 1 to 2 equivalents relative to the desired degree of substitution of hydroxyl groups, and then with $R^{5a}$—X or $R^{17}$—X in an amount of 1 to 2 equivalents relative to the base.

The post-protection reaction may be effected in a solvent, which is selected from hydrocarbons such as benzene and toluene, and ethers such as dibutyl ether, diethylene glycol diethyl ether, diethylene glycol dimethyl ether, tetrahydrofuran and 1,4-dioxane, alone or in admixture. Suitable bases used herein include, but are not limited to, sodium hydride, n-butyllithium, lithium diisopropylamide, triethylamine, and pyridine.

Resist Composition

When polymer P1 is added to a resist composition, a total amount of polymer(s) P1 is preferably 0.1 to 50 parts, and more preferably 0.5 to 10 parts by weight per 100 parts by weight of a base resin (B). At least 0.1 part of polymer P1 is effective for improving the receding contact angle with water of a resist film at its surface. When the amount of polymer P1 is up to 50 parts, a resist film has a sufficiently low rate of dissolution in alkaline developer to maintain the height of a resultant fine size pattern.

In the resist composition of the invention, polymer P1 is used in admixture with a base resin (B) to be described below. Since polymer P1 contains a plurality of fluorine atoms, overall polymer P1 functions as a surfactant so that it may segregate in an upper layer of a resist film being spin coated. The resulting resist film displays improved water repellency and water slip on its surface and prevents water-soluble components from being leached out of the resist material. Also, polymer P1 which contains an alkaline hydrolysis-susceptible structure as mentioned above may enhance the hydrophilic property of the resist film surface after development, inhibiting the occurrence of blob defects.

The resist composition contains (B) a base resin or polymer having a lactone ring-derived structure and/or hydroxyl group-containing structure and/or maleic anhydride-derived structure which becomes soluble in alkaline developer under the action of acid. The polymers which can serve as the base resin (B) include (meth)acrylate polymers, (α-trifluoromethyl)acrylate-maleic anhydride copolymers, cycloolefin-maleic anhydride copolymers, polynorbornene, cycloolefin ring-opening metathesis polymerization (ROMP) polymers, hydrogenated cycloolefin ROMP polymers, polyhydroxystyrene, copolymers of hydroxystyrene with one or more of (meth)acrylate, styrene, vinylnaphthalene, vinylanthracene, vinylpyrene, hydroxyvinylnaphthalene, hydroxyvinylanthracene, indene, hydroxyindene, acenaphthylene, and norbornadiene derivatives, and novolac resins. Suitable polymers possessing a lactone ring-derived structure and/or hydroxyl group-containing structure and/or maleic anhydride-derived structure and having an acid labile group so that the polymer may become soluble in alkaline developer under the action of acid are described in U.S. Pat. No. 7,537,880 or JP-A 2008-111103, paragraphs [0072] to [0120]. The polymer serving as base resin (B) is not limited to one type and a mixture of two or more polymers may be added. The use of plural polymers allows for easy adjustment of resist properties.

The base resin (B) may comprise recurring units of at least one type selected from the general formulae (2A) to (2D).

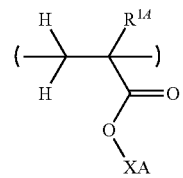

(2A)

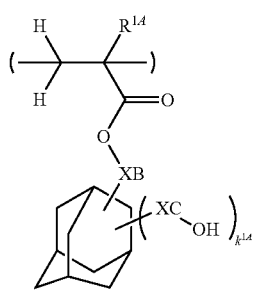 (2B)

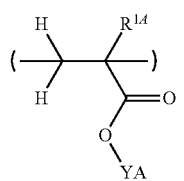 (2C)

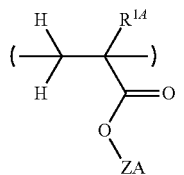 (2D)

Herein $R^{1A}$ is hydrogen, fluorine, methyl or trifluoromethyl, XA is an acid labile group, XB and XC are each independently a single bond or a straight or branched $C_1$-$C_4$ divalent hydrocarbon group (typically alkylene), YA is a substituent group having a lactone structure, ZA is hydrogen, or a $C_1$-$C_{15}$ fluoroalkyl group or $C_1$-$C_{15}$ fluoroalcohol-containing substituent group, and $k^{1A}$ is an integer of 1 to 3.

A polymer comprising recurring units of formula (2A) is decomposed under the action of an acid to generate carboxylic acid so that the polymer may become alkali soluble. While the acid labile group XA may be selected from a variety of such groups, it may be as exemplified above for $R^{5a}$ in formulae (2a) to (2i).

Examples of recurring units of formula (2A) are given below, but not limited thereto.

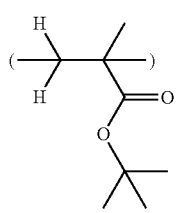 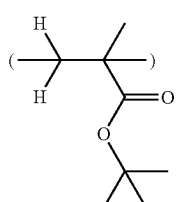

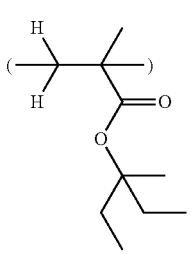 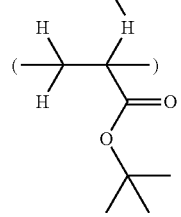

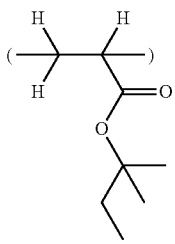 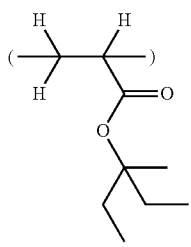

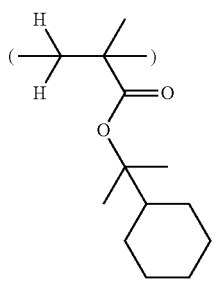 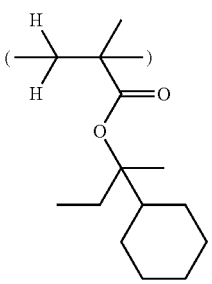

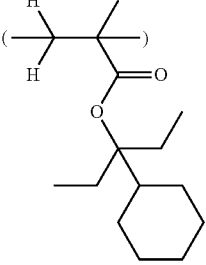 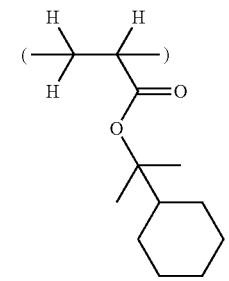

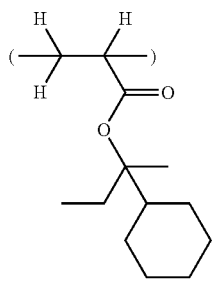 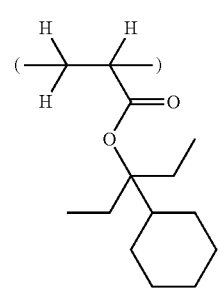

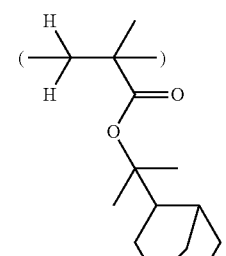 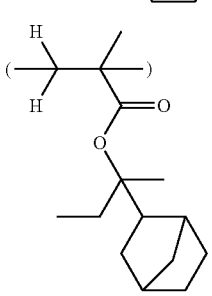

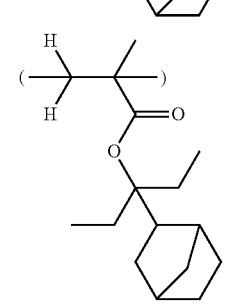 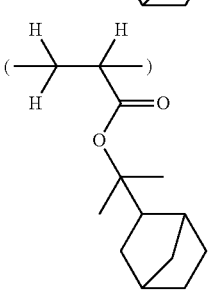

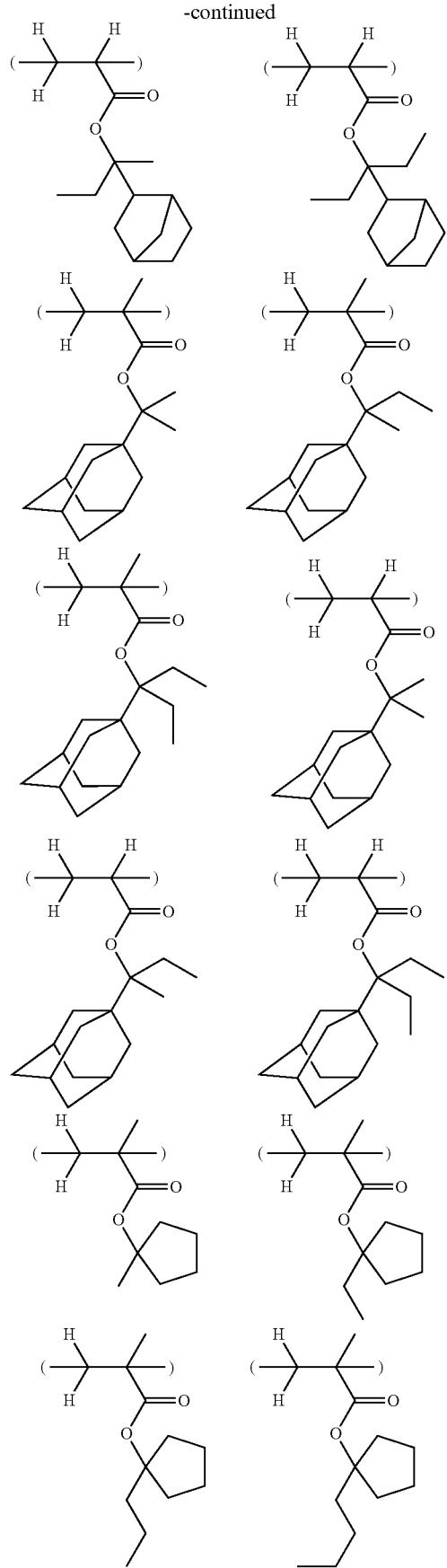
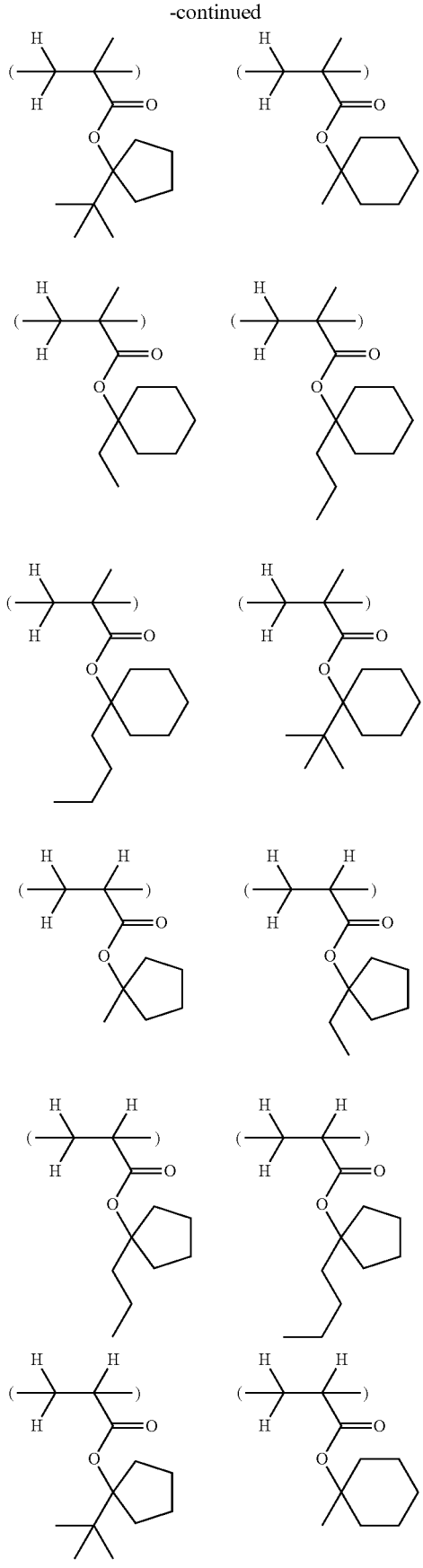

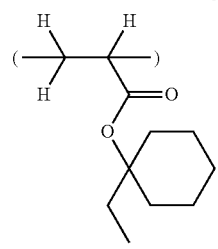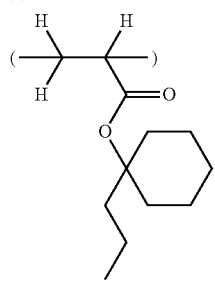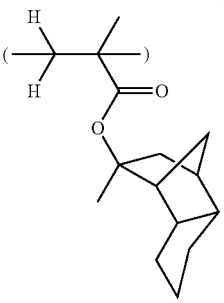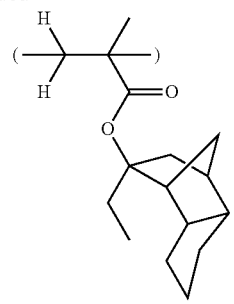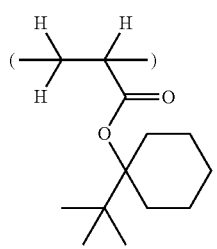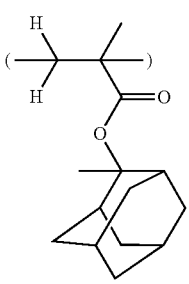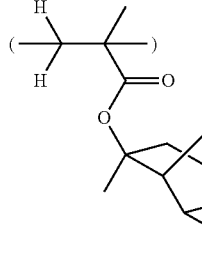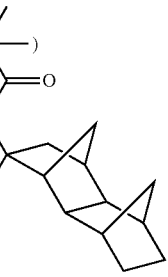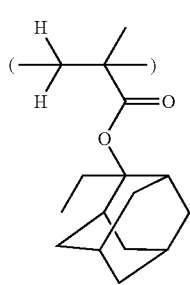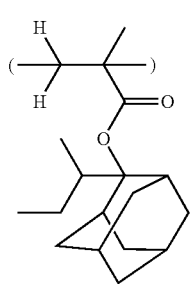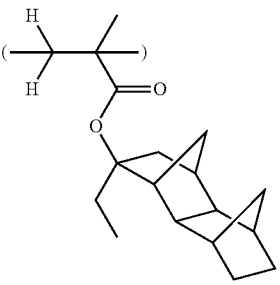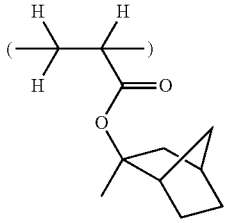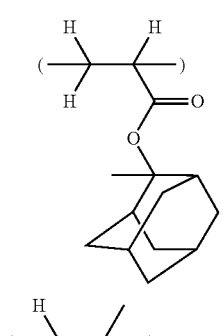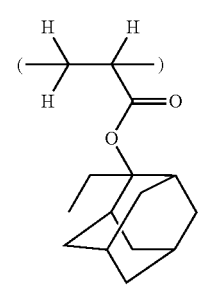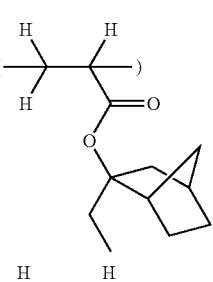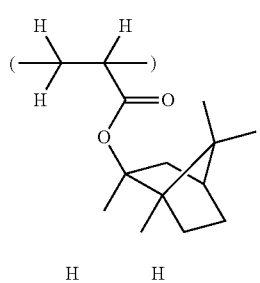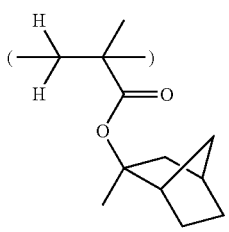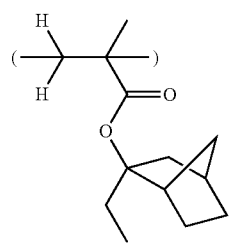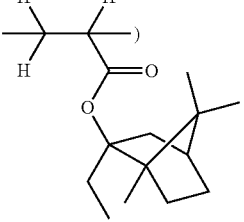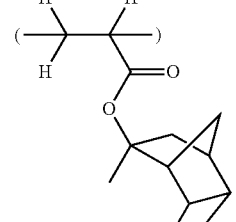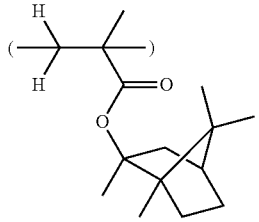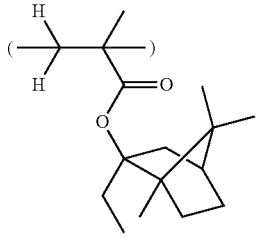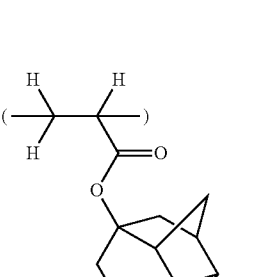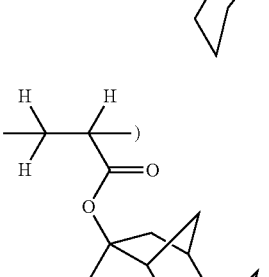

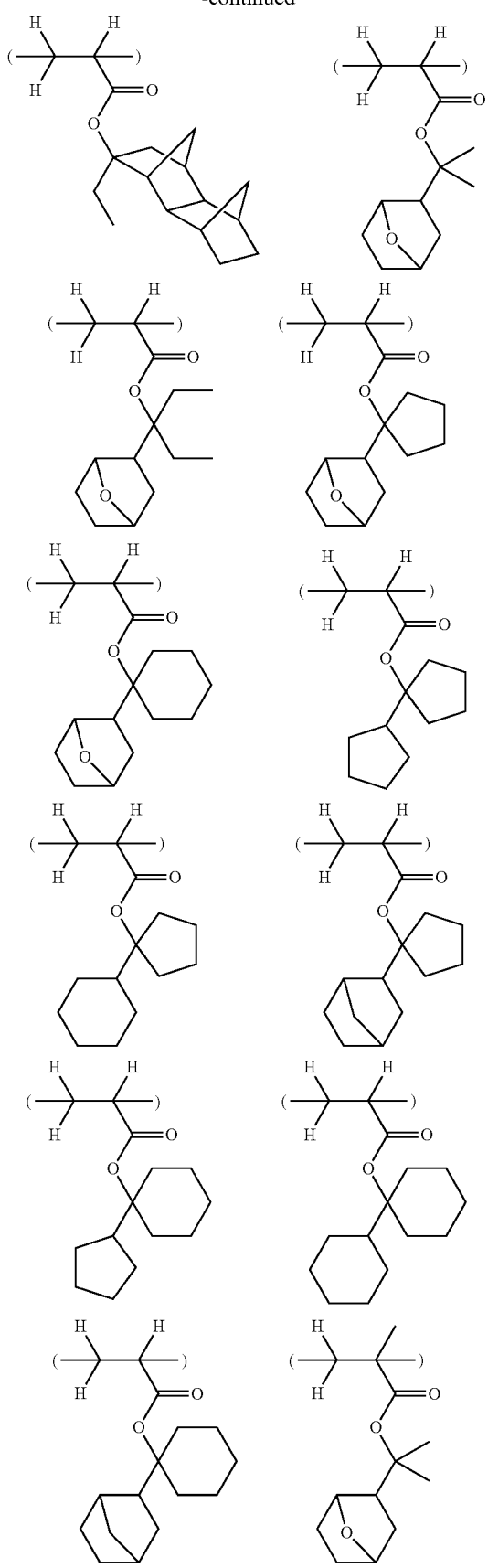
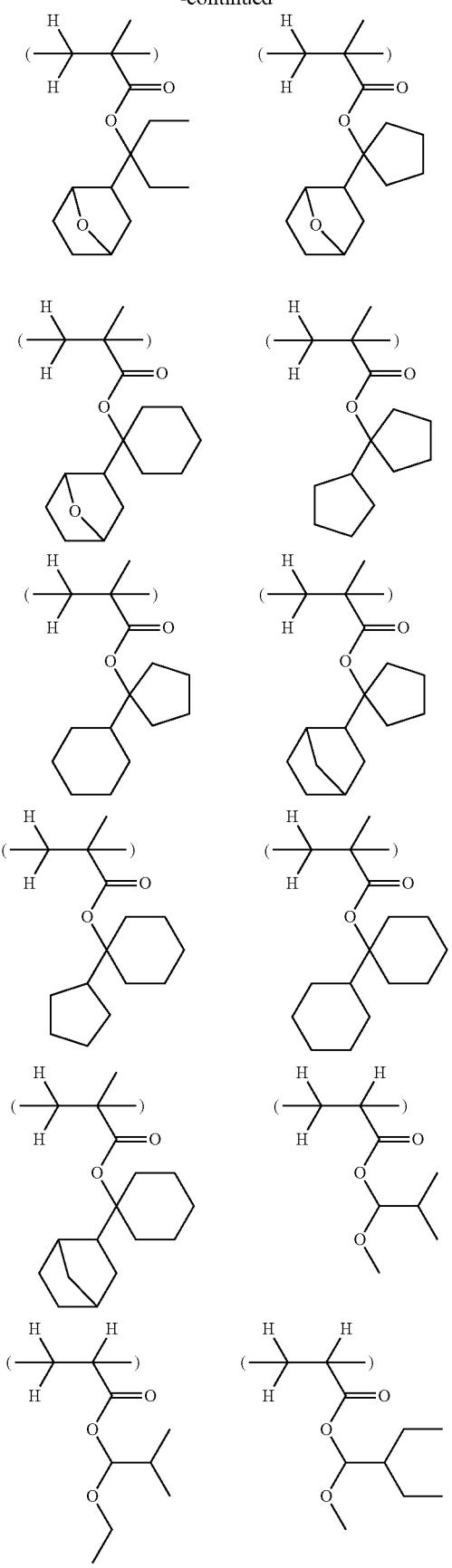

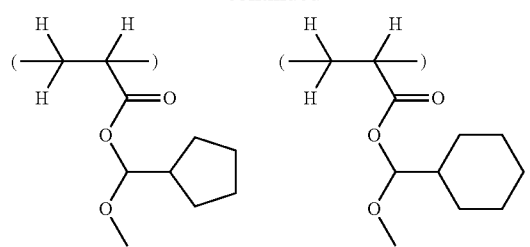
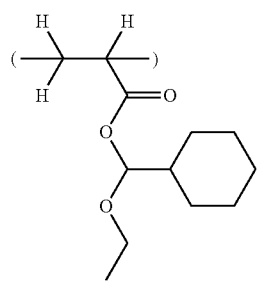
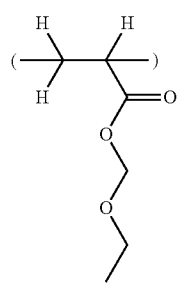
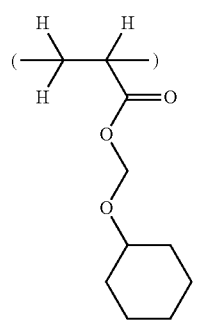
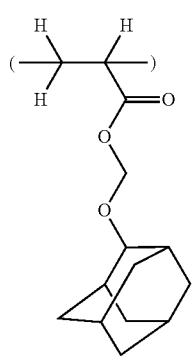
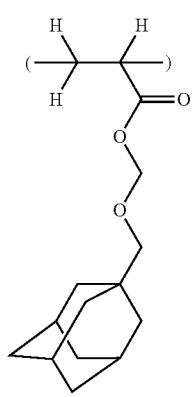
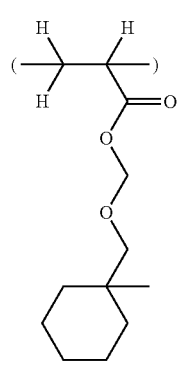
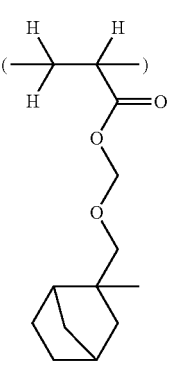
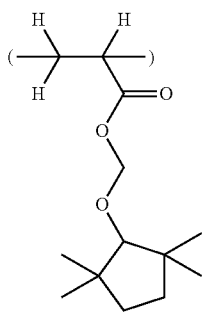
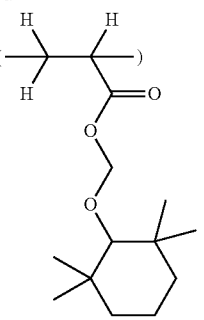
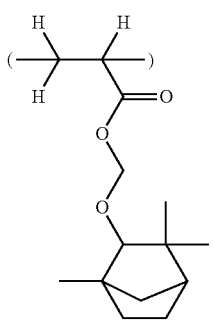
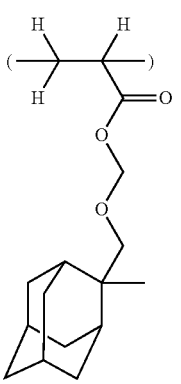
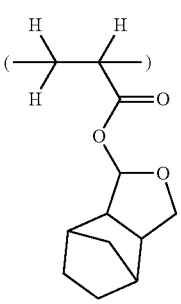
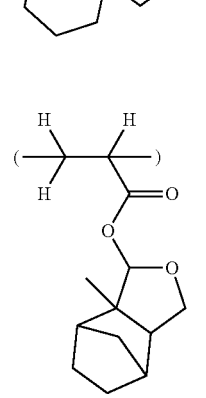
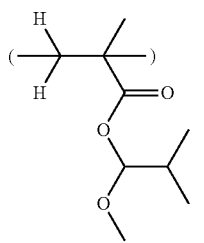
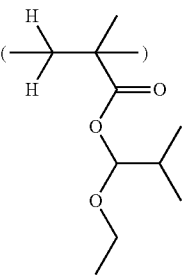
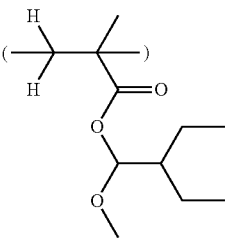

-continued
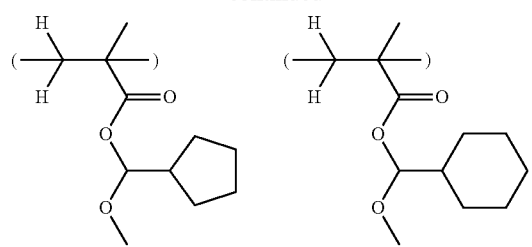
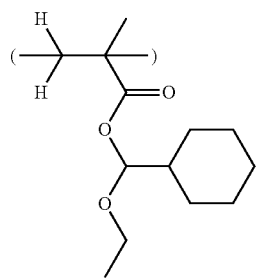
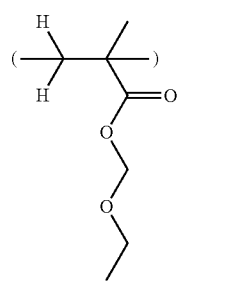
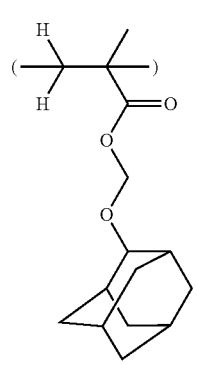
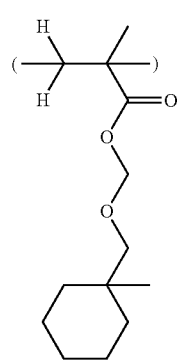
-continued
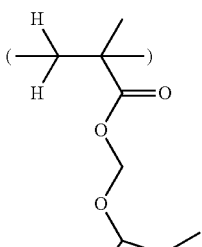
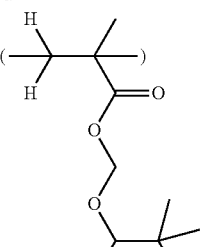
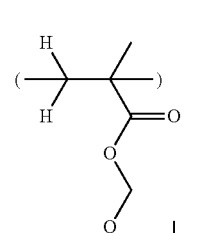
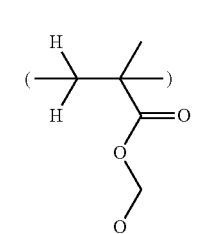
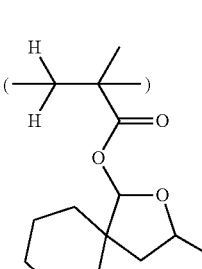
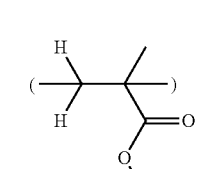
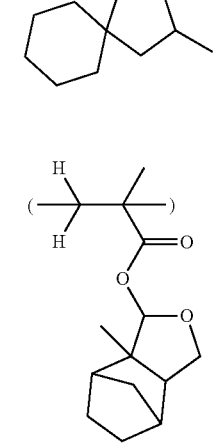
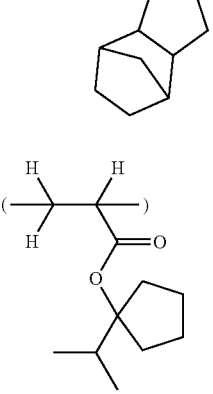
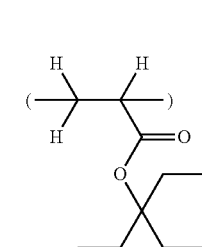
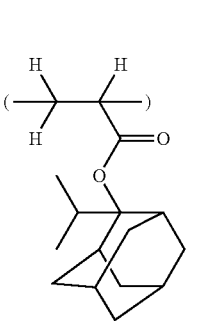

-continued
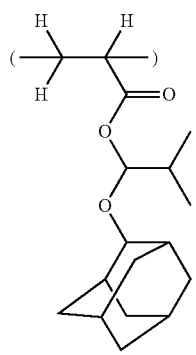 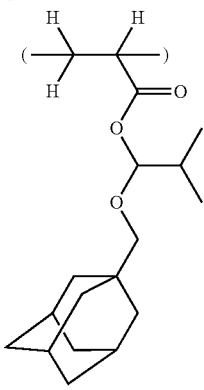 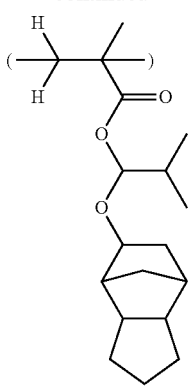 [SMILES: CCC(C)(C)C(=O)OC(OC1CC2CC1C1CCCC21)C(C)C]
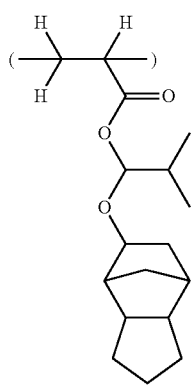 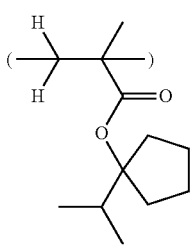
Examples of recurring units of formula (2B) are given below, but not limited thereto.
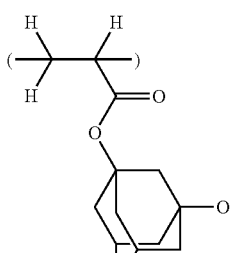 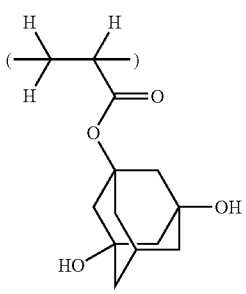
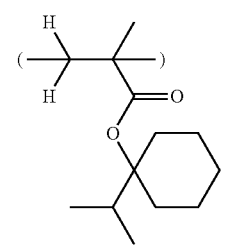 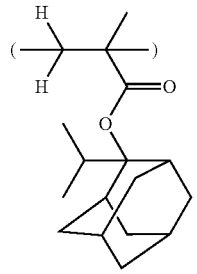
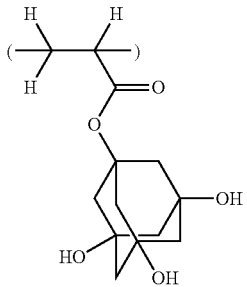 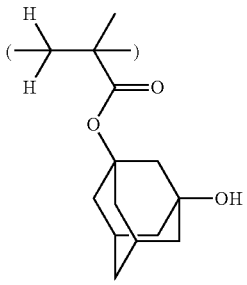
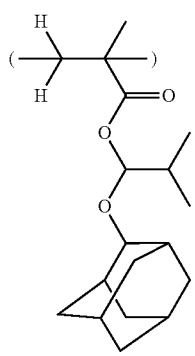 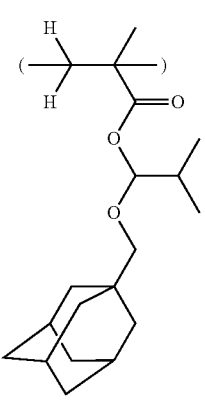
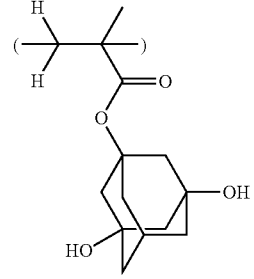 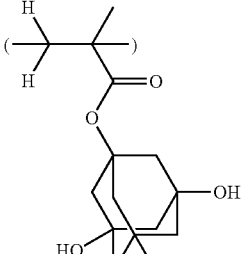
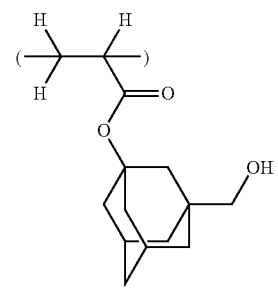 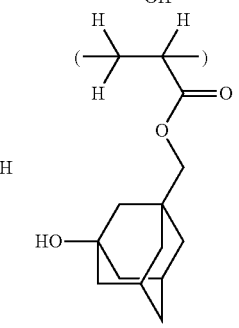

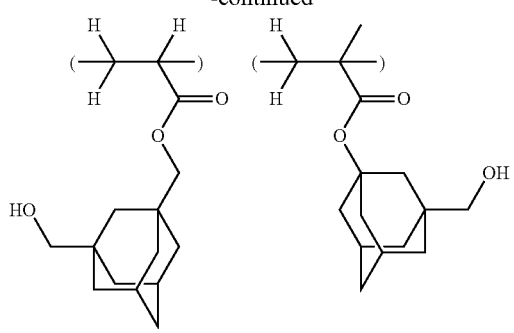
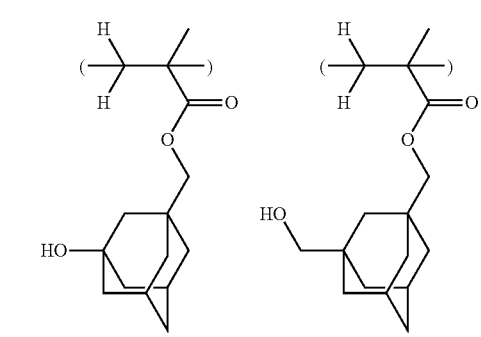
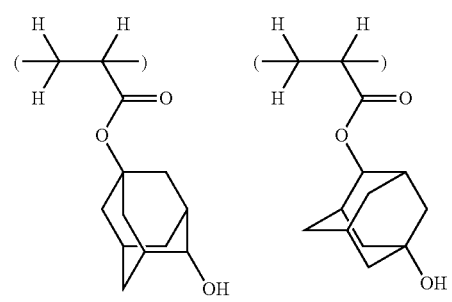
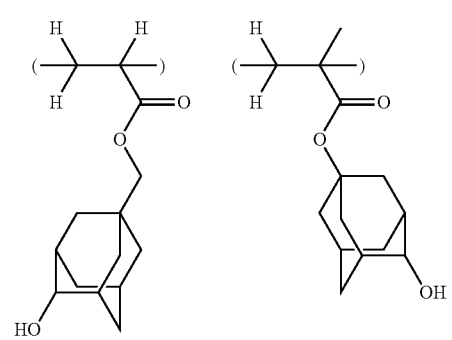
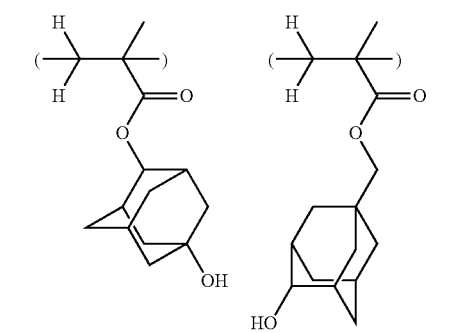
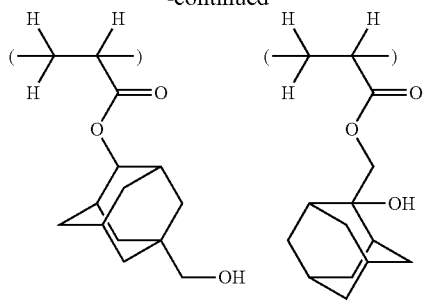
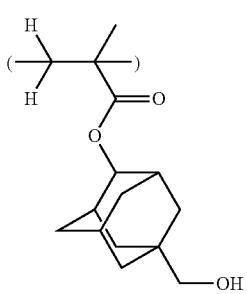
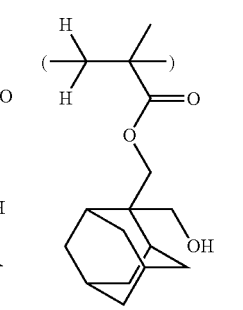
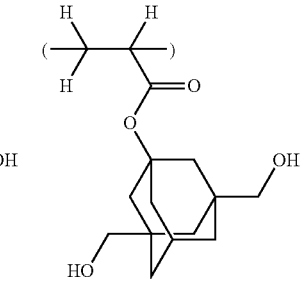
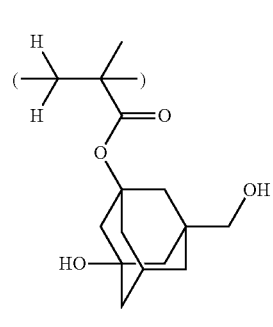

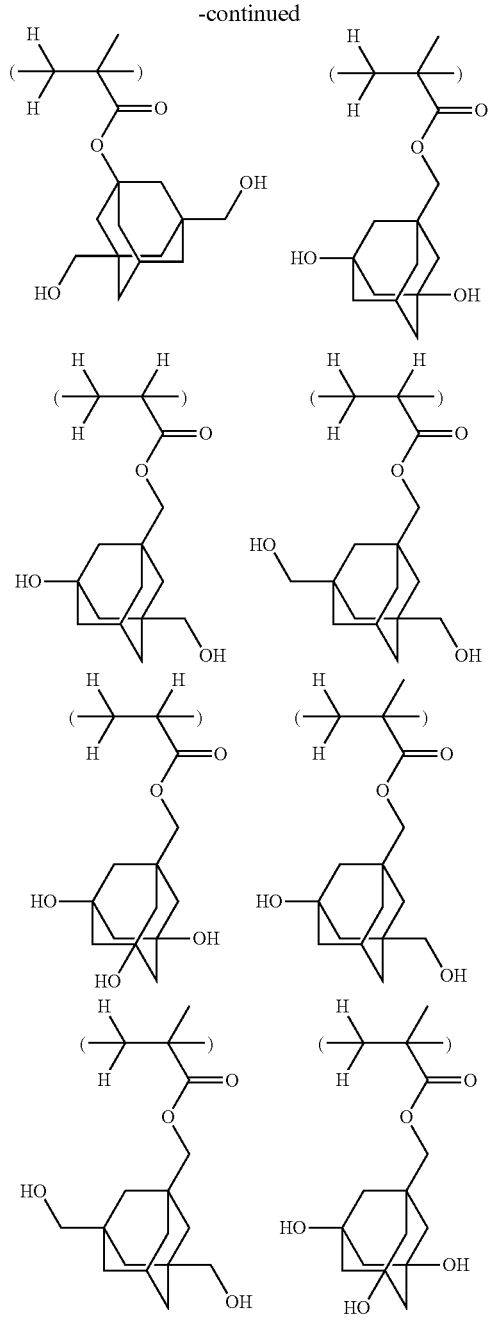
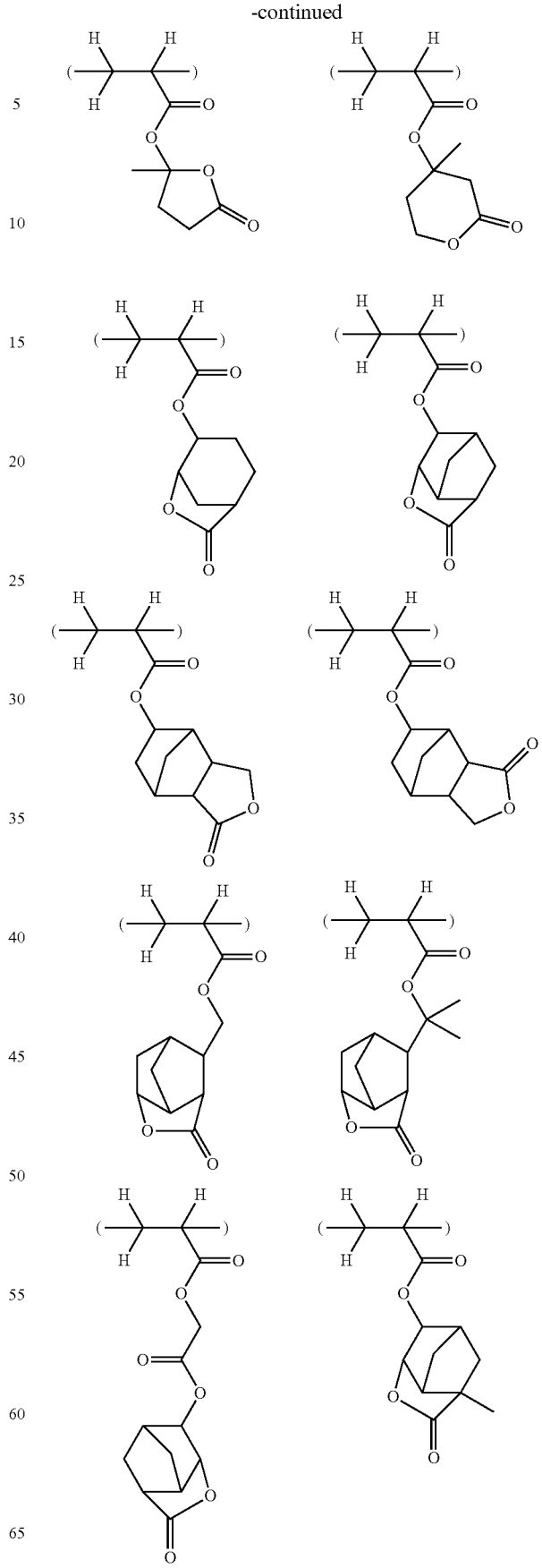
Examples of recurring units of formula (2C) are given below, but not limited thereto.
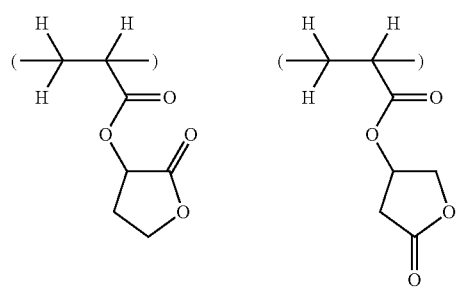

-continued
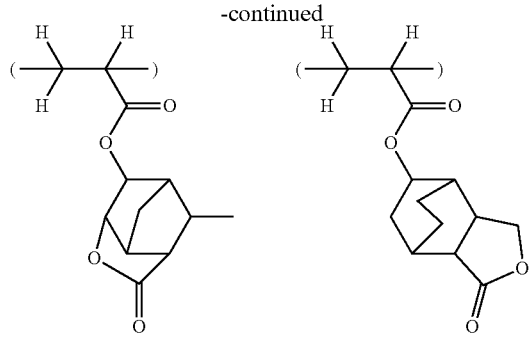
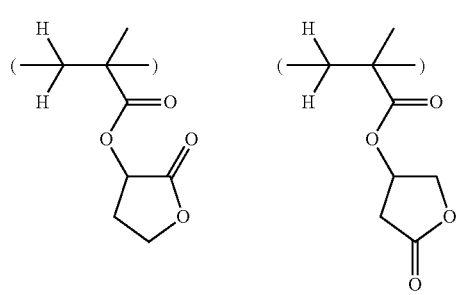
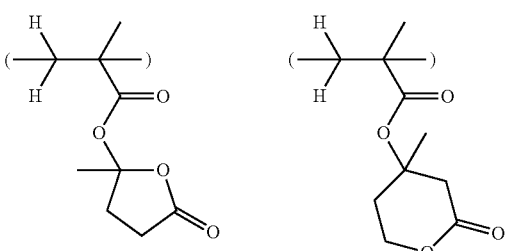
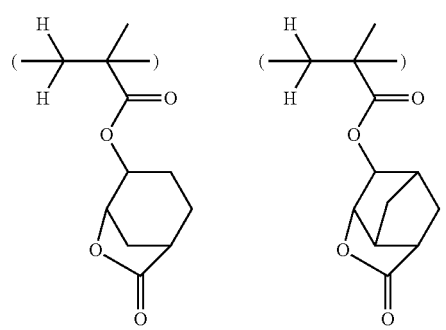
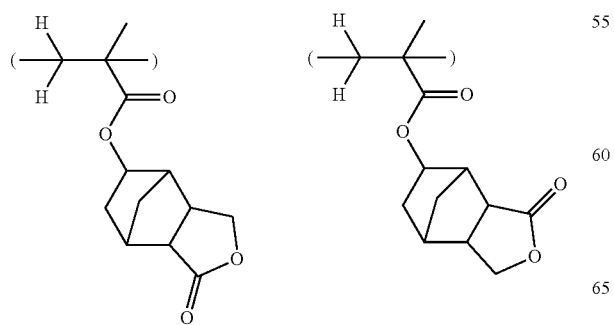
-continued
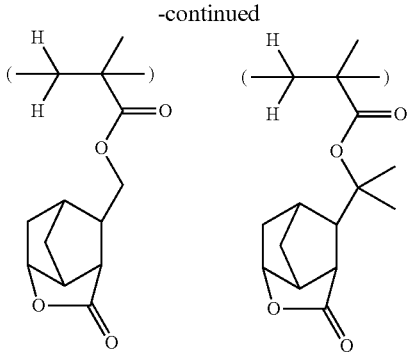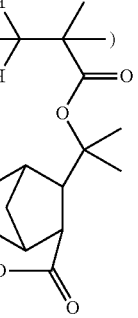
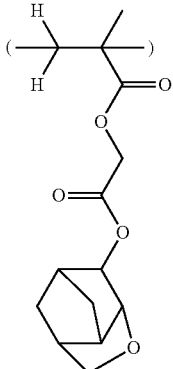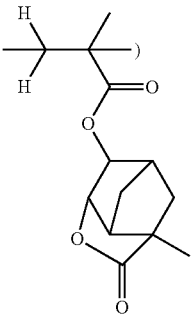
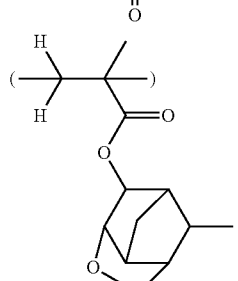
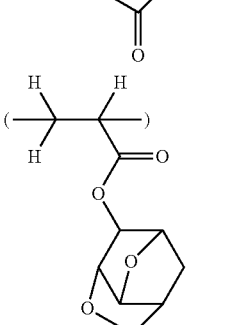
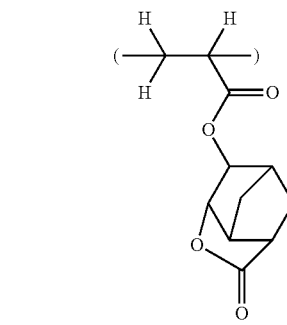

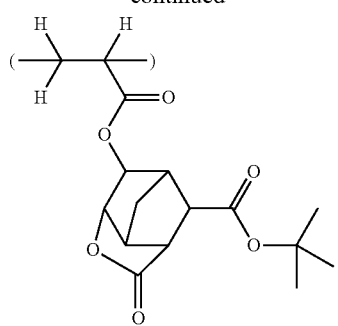
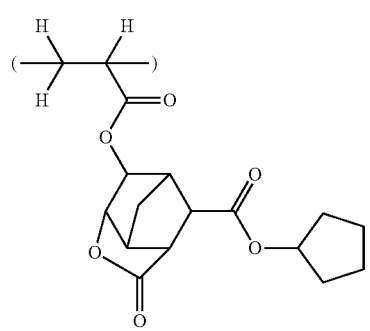
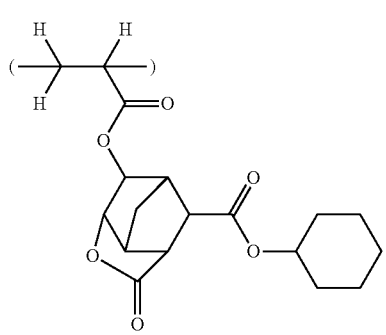
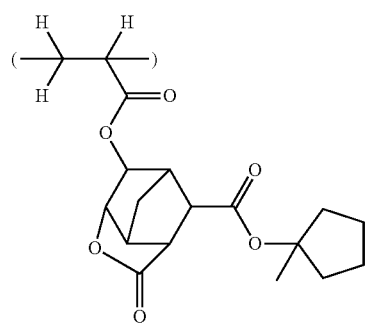
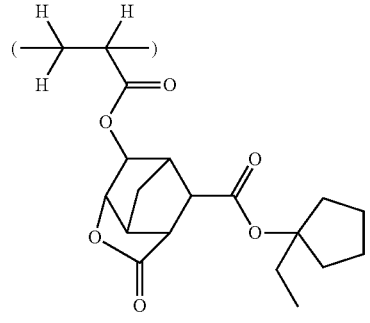
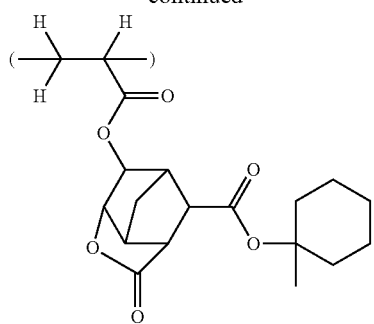
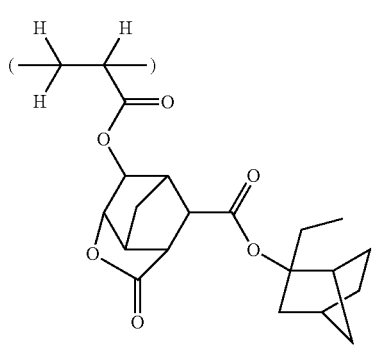
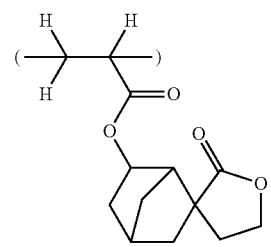
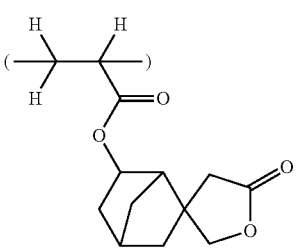
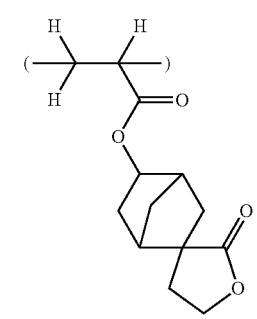
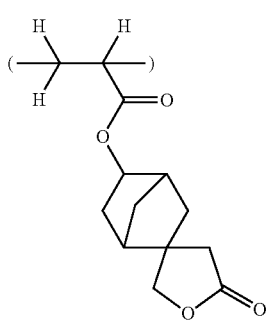

73
-continued
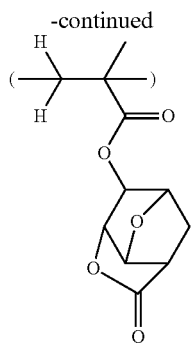
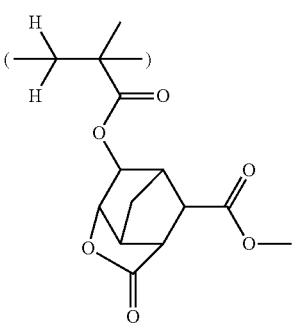
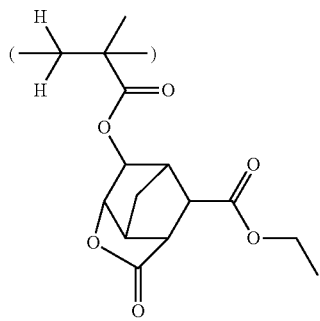
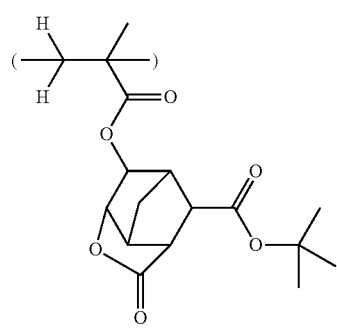
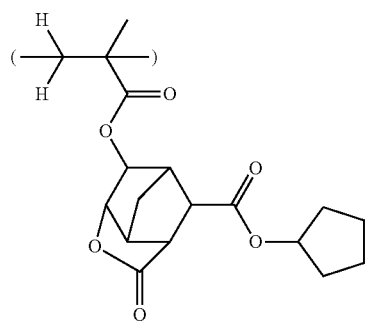
74
-continued
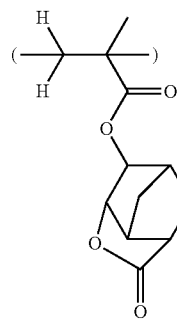
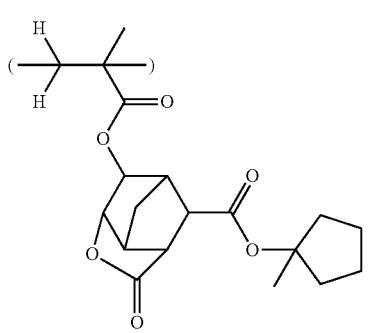
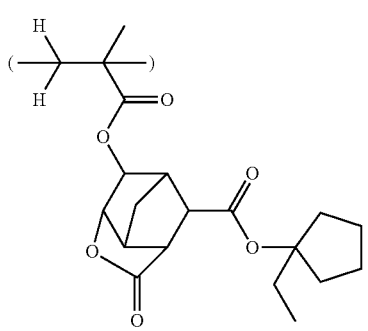
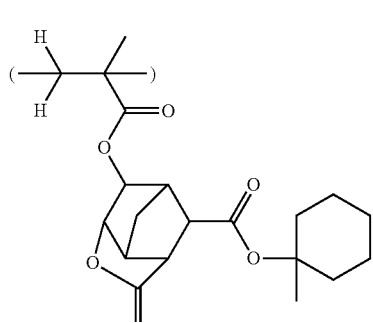
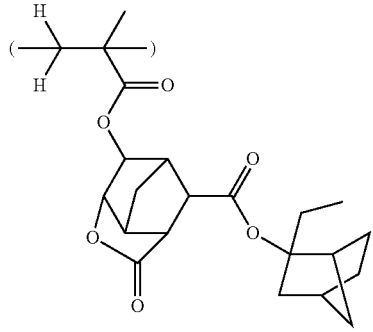

-continued
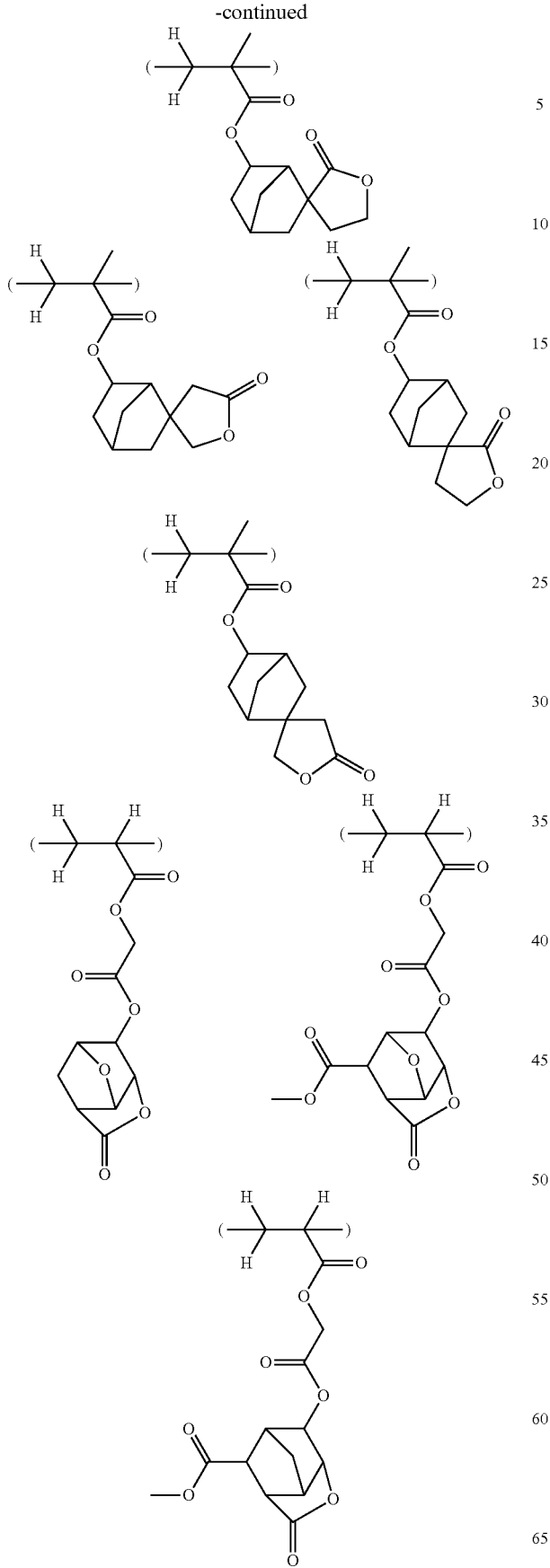
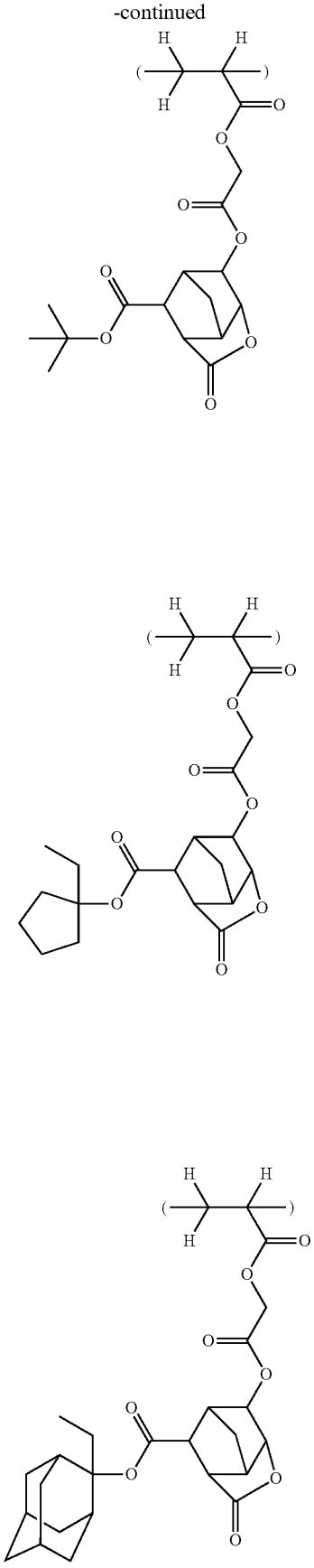

77
-continued
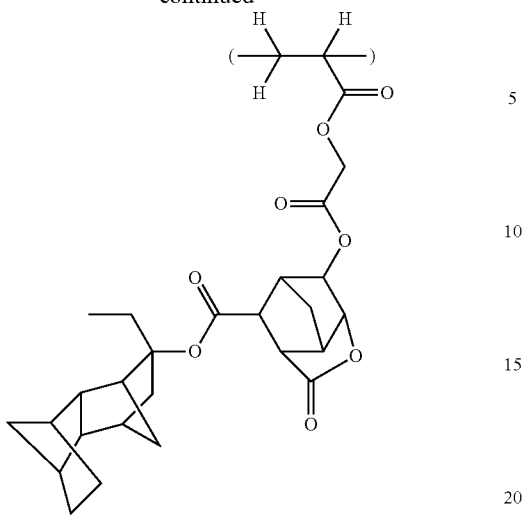
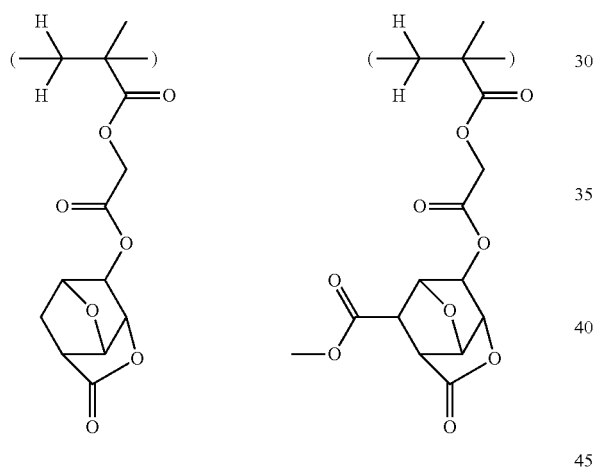
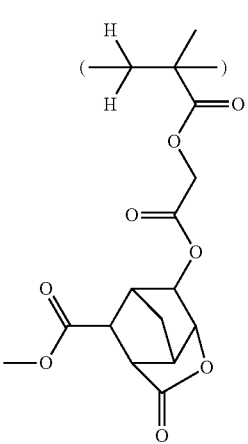
78
-continued
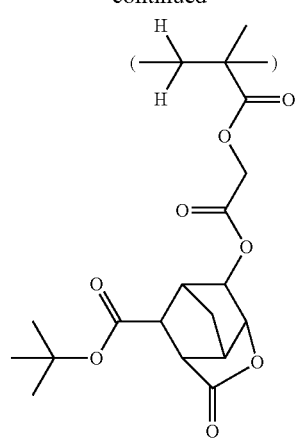
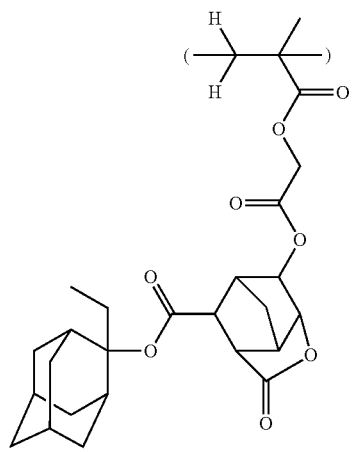

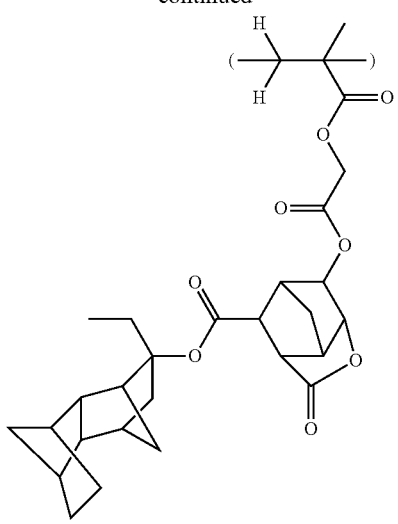
Examples of recurring units of formula (2D) are given below, but not limited thereto.
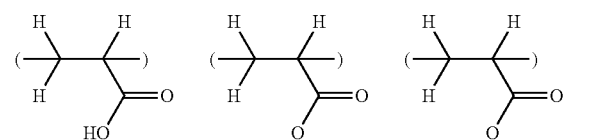
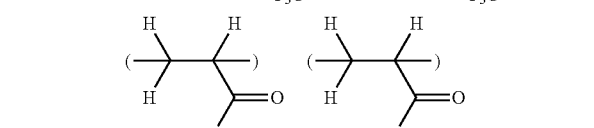
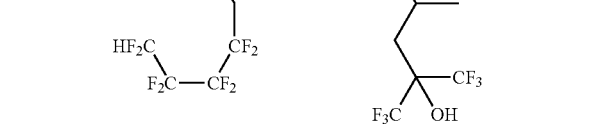
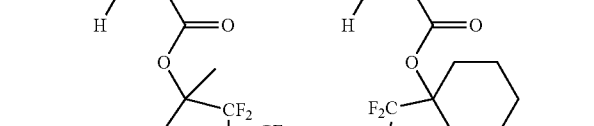
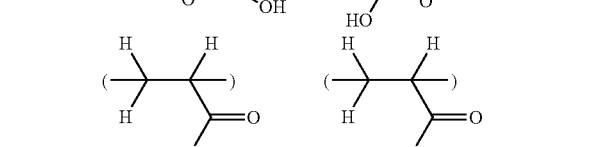
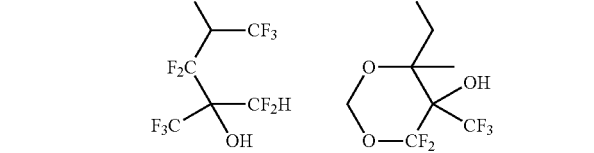
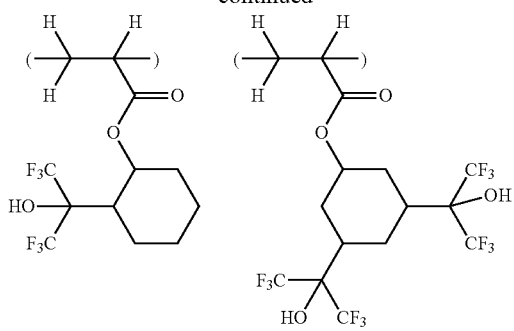
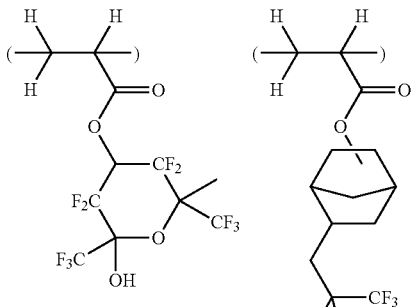
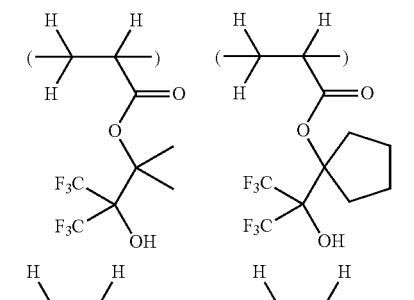
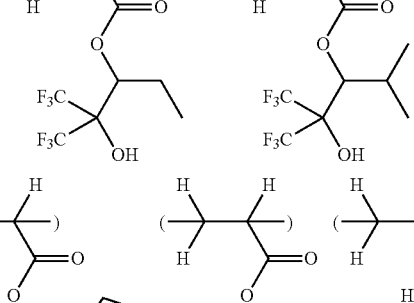
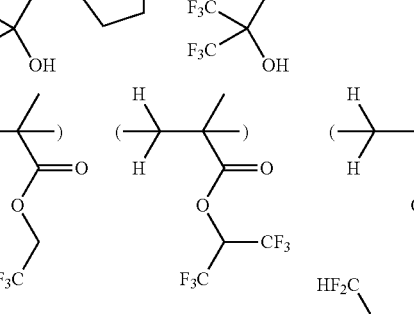

-continued

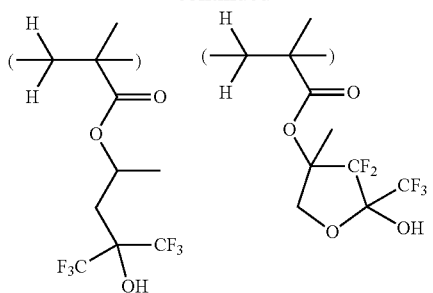
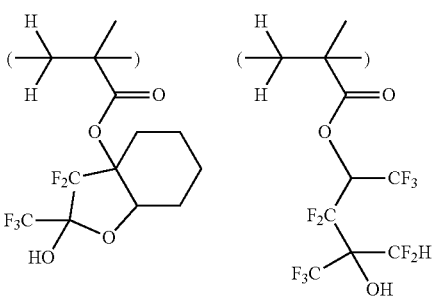
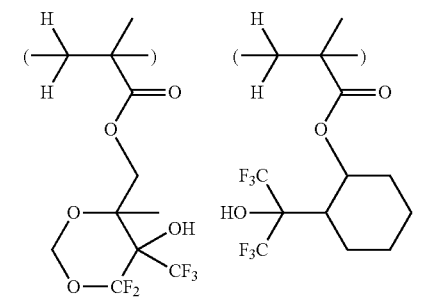
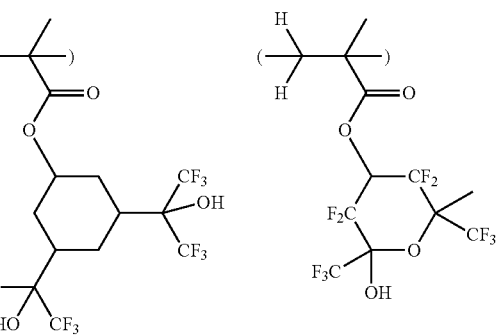
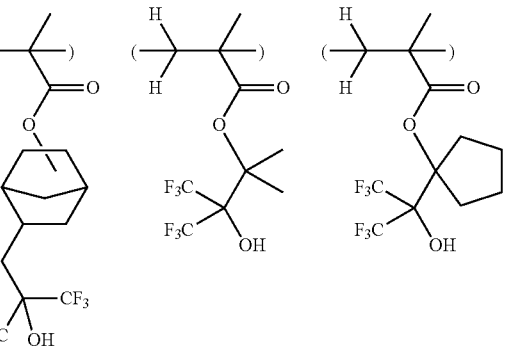

-continued

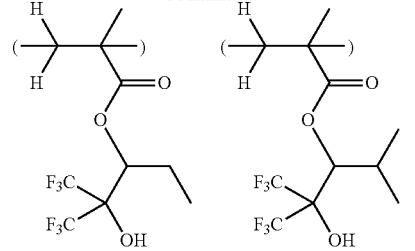
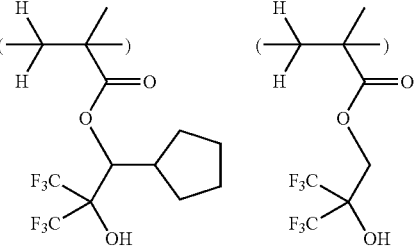

In order that the resist composition function as a chemically amplified positive resist composition, (C) a compound capable of generating an acid upon exposure to high-energy radiation, referred to as "photoacid generator" or PAG, may be compounded. The PAG may be any compound capable of generating an acid upon exposure of high-energy radiation. Suitable PAGs include sulfonium salts, iodonium salts, sulfonyldiazomethane, N-sulfonyloxyimide, and oxime-O-sulfonate acid generators. Exemplary acid generators are described in JP-A 2010-002599, paragraphs [0091] to [0117].

The preferred PAGs are those compounds of the general formula (C)-1.

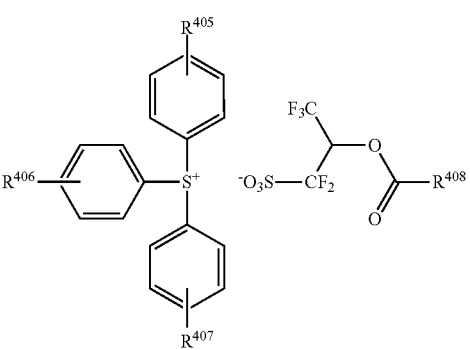

(C)-1

Herein $R^{405}$, $R^{406}$, and $R^{407}$ are each independently hydrogen or a straight, branched or cyclic $C_1$-$C_{20}$ monovalent hydrocarbon group which may contain a heteroatom, typically an alkyl or alkoxy group. $R^{408}$ is a straight, branched or cyclic $C_7$-$C_{30}$ monovalent hydrocarbon group which may contain a heteroatom.

Examples of the hydrocarbon groups optionally containing a heteroatom, represented by $R^{405}$, $R^{406}$, and $R^{407}$, include methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, butyladamantyl, and modified forms of the foregoing in which any carbon-carbon bond is separated by a hetero-atomic grouping such as —O—, —S—, —SO—, —SO$_2$—, —NH—, —C(=O)—, —C(=O)O—, or —C(=O)NH—, or any hydrogen atom is replaced by a functional radical such as —OH, —NH$_2$, —CHO, or —CO$_2$H. Examples of the straight, branched or cyclic C$_7$-C$_{30}$ monovalent hydrocarbon groups optionally containing a heteroatom, represented by R$^{408}$, are shown below, but not limited thereto.
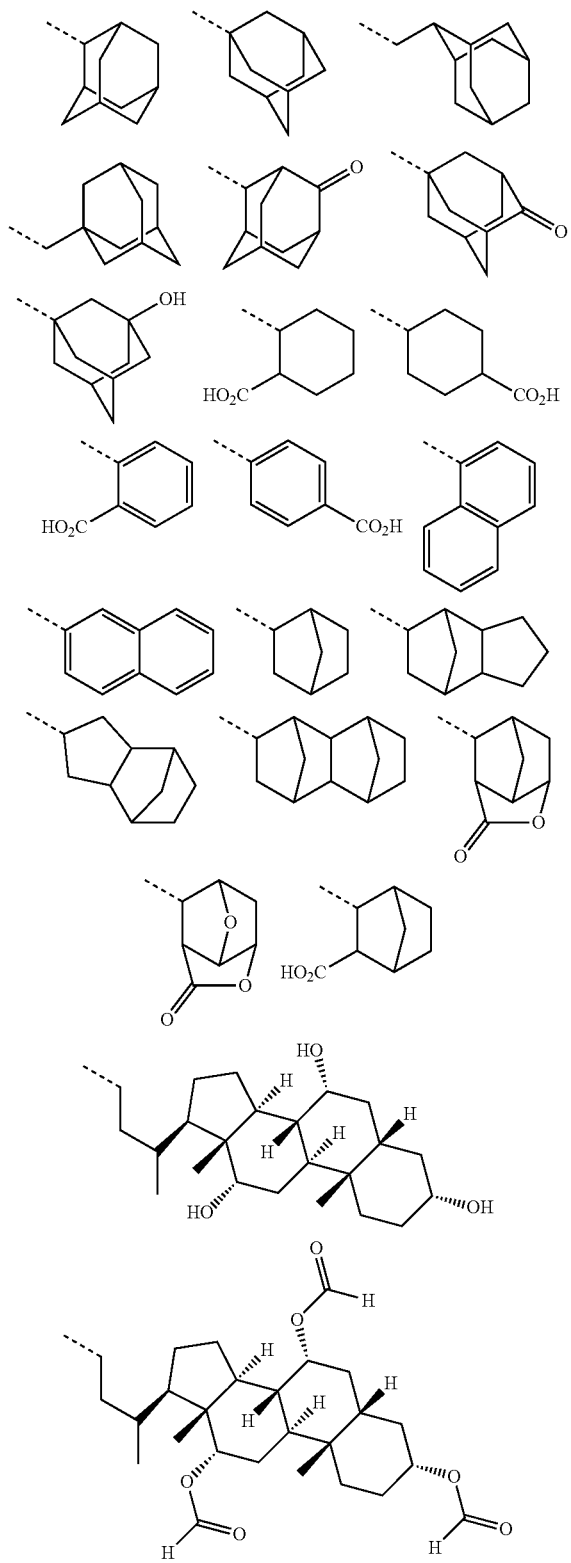
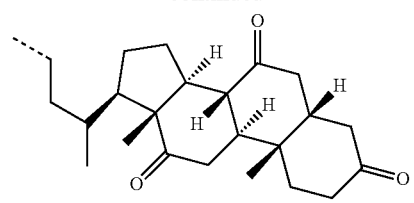
Illustrative examples of acid generators (C)-1 are shown below, but not limited thereto.
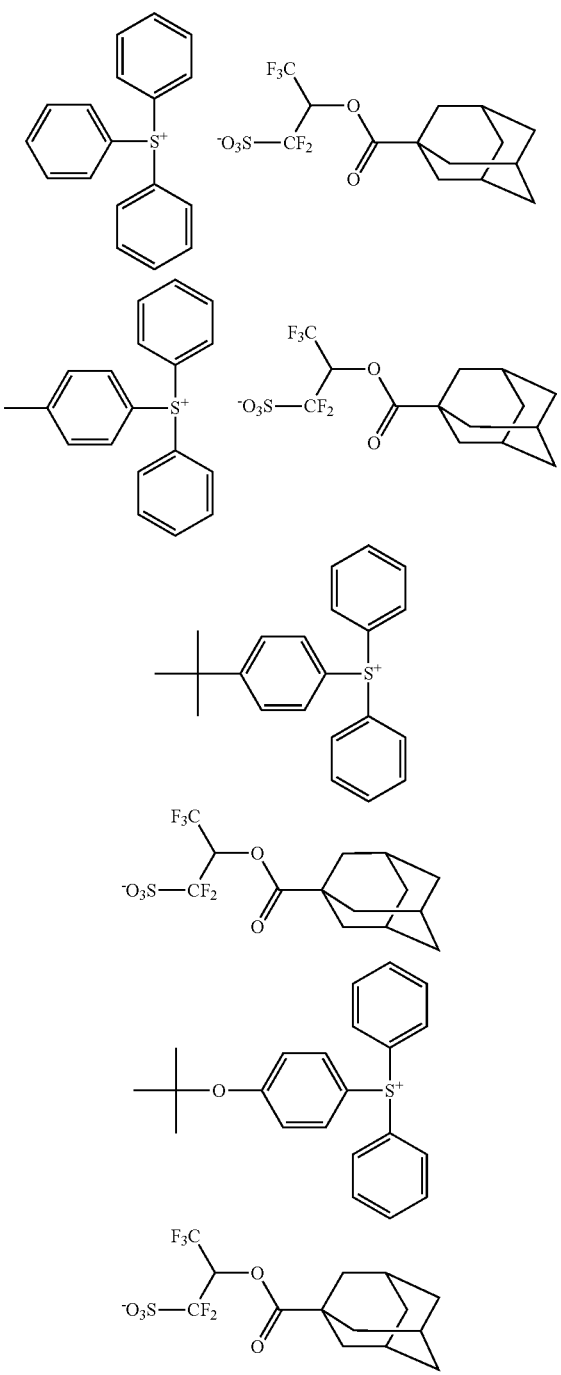

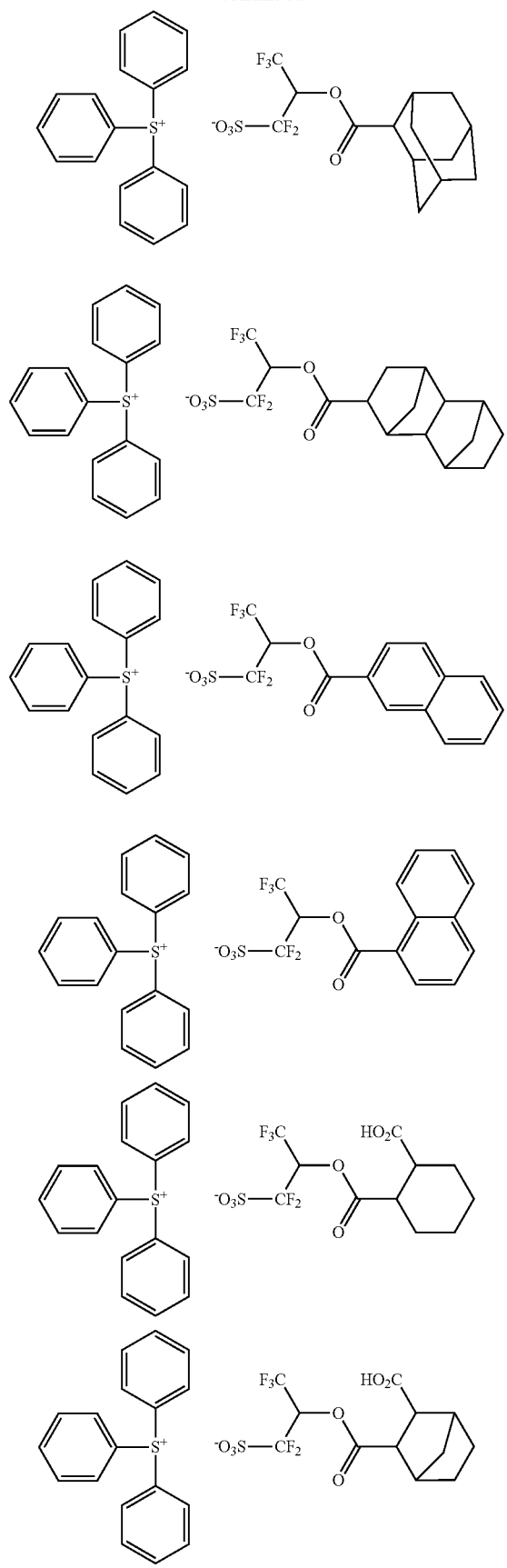
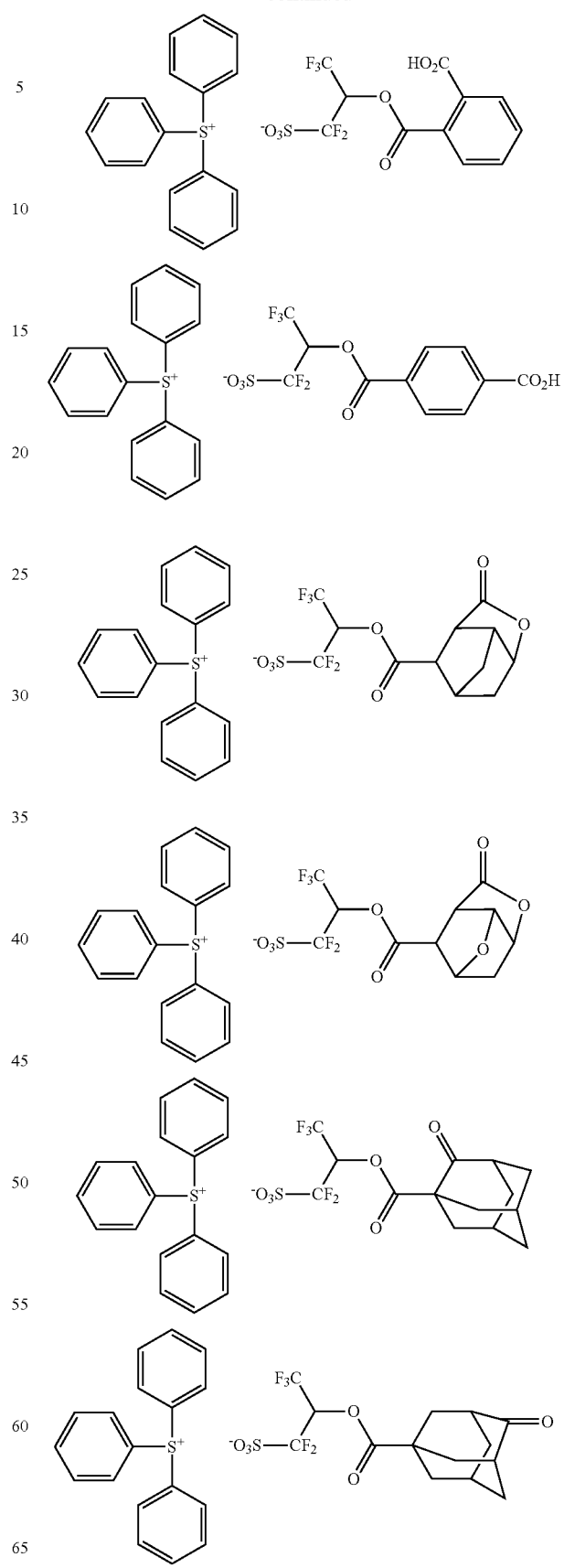

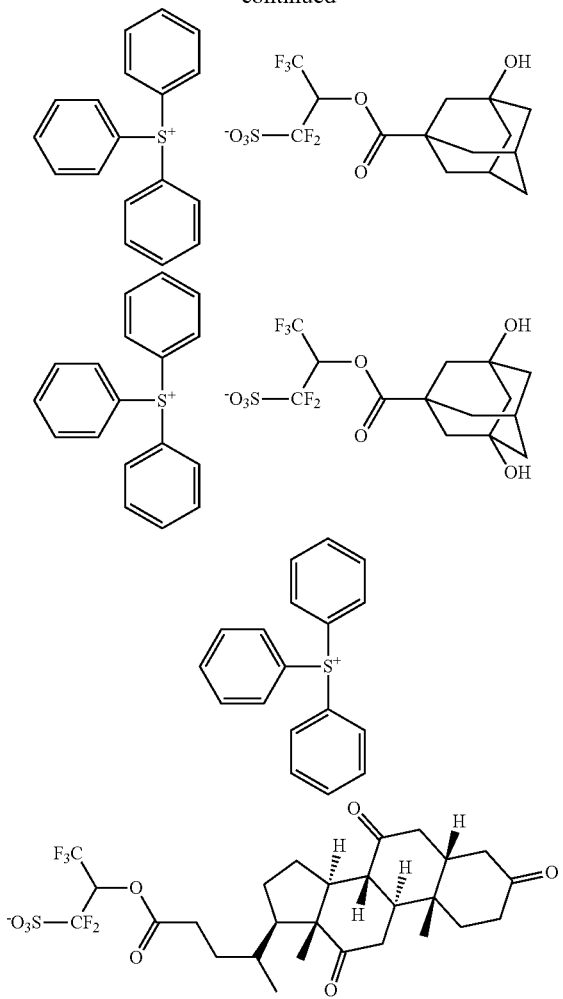

It is noted that an acid diffusion controlling function may be provided when two or more PAGs are used in admixture provided that one PAG is an onium salt capable of generating a weak acid. Specifically, in a system using a mixture of a PAG capable of generating a strong acid (e.g., fluorinated sulfonic acid) and an onium salt capable of generating a weak acid (e.g., non-fluorinated sulfonic acid or carboxylic acid), if the strong acid generated from the PAG upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If the PAG capable of generating a strong acid is also an onium salt, an exchange from the strong acid (generated upon exposure to high-energy radiation) to a weak acid as above can take place, but it never happens that the weak acid (generated upon exposure to high-energy radiation) collides with the unreacted onium salt capable of generating a strong acid to induce a salt exchange. This is because of a likelihood of an onium cation forming an ion pair with a stronger acid anion.

An amount of the PAG added as component (C) is not particularly limited as long as the objects of the invention are not compromised. The amount of PAG is 0.1 to 20 parts, more preferably 0.1 to 10 parts, and most preferably 0.1 to 5 parts by weight per 100 parts by weight of the base resin in the composition. An excess of the PAG may cause some problems such as degraded resolution and foreign particles left after development/resist film stripping. The PAG may be used alone or in admixture of two or more. The transmittance of the resist film can be controlled by using a PAG having a low transmittance at the exposure wavelength and adjusting the amount of the PAG added. As long as PAG is up to 20 phr, the resulting photoresist film has a fully high transmittance and a minimal likelihood of degraded resolution. The PAG may be used alone or in admixture of two or more. The transmittance of the resist film can be controlled by using a PAG having a low transmittance at the exposure wavelength and adjusting the amount of the PAG added.

The resist composition may further comprise one or more of (D) an organic solvent, (E) a basic compound, (F) a dissolution regulator, (G) a surfactant, and (H) an acetylene alcohol derivative.

The organic solvent (D) used herein may be any organic solvent in which polymer P1, the base resin, PAG, and other components are soluble. Exemplary solvents are described in JP-A 2008-111103, paragraph [0144]. The organic solvents may be used alone or in combinations of two or more thereof. An appropriate amount of the organic solvent used is 200 to 3,000 parts, especially 400 to 2,500 parts by weight per 100 parts by weight of the base resin (B). It is recommended to use diethylene glycol dimethyl ether, 1-ethoxy-2-propanol, propylene glycol monomethyl ether acetate (PGMEA), and mixtures thereof because the acid generator is most soluble therein.

As the basic compound (E), nitrogen-containing organic compounds are preferred and may be used alone or in admixture. Those compounds capable of suppressing the rate of diffusion when the acid generated by the acid generator diffuses within the resist film are useful. The inclusion of nitrogen-containing organic compound holds down the rate of acid diffusion within the resist film, resulting in better resolution. In addition, it suppresses changes in sensitivity following exposure and reduces substrate and environment dependence, as well as improving the exposure latitude and the pattern profile.

Suitable nitrogen-containing organic compounds include primary, secondary, and tertiary aliphatic amines, mixed amines, aromatic amines, heterocyclic amines, nitrogen-containing compounds having carboxyl group, nitrogen-containing compounds having sulfonyl group, nitrogen-containing compounds having hydroxyl group, nitrogen-containing compounds having hydroxyphenyl group, amide, imide and carbamate derivatives. Illustrative examples are described in JP-A 2008-111103, paragraphs [0149] to [0163]. The basic compound is preferably used in an amount of 0.001 to 2 parts, more preferably 0.01 to 1 part by weight per 100 parts by weight of the base resin (B). At least 0.001 phr achieves the desired addition effect whereas up to 2 phr minimizes the risk of reducing sensitivity.

The dissolution regulator or inhibitor (F) which can be added to the resist composition is a compound having on the molecule at least two phenolic hydroxyl groups which are protected with an acid labile group, or a compound having on the molecule at least one carboxyl group which is protected with an acid labile group. Exemplary regulators are described in JP-A 2008-122932, paragraphs [0155] to [0178].

Optionally, the resist composition of the invention may further comprise (G) a surfactant which is commonly used for facilitating the coating operation. The surfactant may be added in conventional amounts so long as this does not compromise the objects of the invention.

Illustrative, non-limiting examples of the surfactant (G) include nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkylaryl ethers such as polyoxyethylene octylphenol ether and polyoxyethylene nonylphenol ether, polyoxyethylene polyoxypropylene block copolymers, sorbitan fatty acid esters such as sorbitan monolaurate, sorbitan monopalmitate, and sorbitan monostearate, and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorochemical surfactants such as EFTOP EF301, EF303 and EF352 (JEMCO Inc.), Megaface F171, F172, F173, R08, R30, R90 and R94 (DIC Corp.), Fluorad FC-430, FC-431, FC-4430 and FC-4432 (Sumitomo 3M Co., Ltd.), Asahiguard AG710, Surflon S-381, S-382, S-386, SC101, SC102, SC103, SC104, SC105, SC106, KH-10, KH-20, KH-30 and KH-40 (Asahi Glass Co., Ltd.), and Surfynol E1004 (Nissin Chemical Industry Co., Ltd.); organosiloxane polymers KP341, X-70-092 and X-70-093 (Shin-Etsu Chemical Co., Ltd.), acrylic acid or methacrylic acid Polyflow No. 75 and No. 95 (Kyoeisha Ushi Kagaku Kogyo Co., Ltd.). Additional useful surfactants include partially fluorinated oxetane ring-opened polymers having the structural formula (surf-1) below.

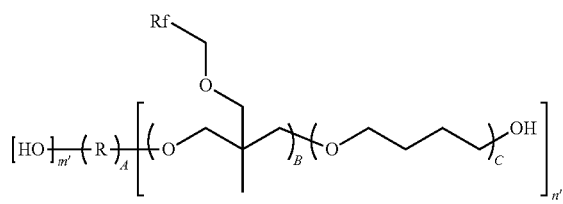

It is provided herein that R, Rf, A, B, C, m', and n' are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

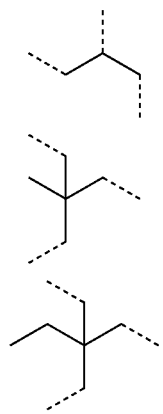

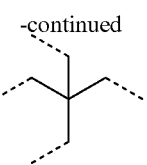

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m' is an integer of 0 to 3, n' is an integer of 1 to 4, and the sum of m' and n', which represents the valence of R, is an integer of 2 to 4. A is equal to 1, B is an integer of 2 to 25, and C is an integer of 0 to 10. Preferably, B is an integer of 4 to 20, and C is 0 or 1. Note that the above structural formula does not prescribe the arrangement of respective constituent units while they may be arranged either in blocks or randomly. For the preparation of surfactants in the form of partially fluorinated oxetane ring-opened polymers, reference should be made to U.S. Pat. No. 5,650,483, for example.

Of the foregoing surfactants, FC-4430, Surflon S-381, Surfynol E1004, KH-20, KH-30, and oxetane ring-opened polymers of formula (surf-1) are preferred. These surfactants may be used alone or in admixture.

In the resist composition, the surfactant is preferably compounded in an amount of up to 2 parts, and especially up to 1 part by weight, per 100 parts by weight of the base resin. The amount of the surfactant, if added, is preferably at least 0.01 phr.

Optionally, the resist composition may further comprise (H) an acetylene alcohol derivative. Exemplary compounds are described in JP-A 2008-122932, paragraphs [0180] to [0181].

Optionally, the resist composition may further comprise (I) a fluorinated alcohol. When the resist composition contains (E) a basic compound, the fluorinated ester in recurring units (1a) of polymer P1 is subject to gradual hydrolysis during storage, which may lead to a decline of water repellent and water slip performance during the immersion lithography process. In such a case, (I) a fluorinated alcohol may be added to the resist composition for suppressing the hydrolysis which is otherwise promoted by the basic compound (E), thus enhancing storage stability.

Examples of the fluorinated alcohol include, but are not limited to, 2,2,2-trifluoroethanol, 2,2,3,3-tetrafluoro-1-propanol, 1,3-difluoro-2-propanol, 1,1,1,3,3,3-hexafluoro-2-propanol, 1,1,1,3,3,3-hexafluoro-2-trifluoromethyl-2-propanol, 2,2,3,4,4,4-hexafluoro-1-butanol, 2,2,2,2',2',2'-hexafluorocumylalcohol, and 2,2,3,3,4,4,5,5-octafluoro-1-pentanol.

The fluorinated alcohol (I) is preferably used in an amount of 0.01 to 10 parts, more preferably 0.01 to 5 parts by weight per part by weight of the basic compound (E).

Pattern Forming Process

It is now described how to form a pattern using the resist composition of the invention. A pattern may be formed from the resist composition using any well-known lithography process. The preferred process includes at least the steps of forming a resist coating on a substrate, exposing it to high-energy radiation, and developing it with a developer.

The resist composition is applied onto a substrate, typically a silicon wafer by a suitable coating technique such as spin coating. The coating is prebaked on a hot plate at a temperature of 60 to 150° C. for 1 to 10 minutes, preferably 80 to 140° C. for 1 to 5 minutes, to form a resist film of 0.01 to 2.0 µm thick. It is noted in conjunction with spin coating that if the resist composition is coated onto the surface of a substrate which has been wetted with the resist solvent or a solution miscible with the resist solvent, then the amount of the resist composition dispensed can be reduced (see JP-A H09-246173).

A mask having the desired pattern is then placed over the photoresist film, and the film exposed through the mask to an electron beam or to high-energy radiation such as deep-UV, excimer laser or x-ray in a dose of 1 to 200 $mJ/cm^2$, and preferably 10 to 100 $mJ/cm^2$. The high-energy radiation used herein preferably has a wavelength in the range of 180 to 250 nm.

Light exposure may be dry exposure in air or nitrogen atmosphere, or immersion lithography of providing a liquid, typically water between the resist film and the projection lens. The liquid used for immersion is a liquid having a refractive index of at least 1 and high transparency at the exposure wavelength, such as water or alkane. EB or EUV exposure in vacuum is also acceptable.

The resist film formed from the resist composition has such barrier properties to water that it may inhibit resist components from being leached out in water and as a consequence, eliminate a need for a protective coating in the immersion lithography and reduce the cost associated with protective coating formation or the like. The resist film has so high a receding contact angle with water that few liquid droplets may be left on the surface of the photoresist film after immersion lithography scanning, minimizing pattern formation failures induced by liquid droplets left on the film surface.

In another version of immersion lithography, a protective coating may be formed on top of the resist film. The resist protective coating may be either of the solvent stripping type or of the developer dissolution type. A resist protective coating of the developer dissolution type is advantageous for process simplicity because it can be stripped during development of a resist film of the resist composition. The resist protective coating used in the immersion lithography may be formed from a coating solution, for example, a topcoat solution of a polymer having acidic units such as 1,1,1,3,3,3-hexafluoro-2-propanol, carboxyl or sulfo groups which is insoluble in water and soluble in an alkaline developer liquid, in a solvent selected from alcohols of at least 4 carbon atoms, ethers of 8 to 12 carbon atoms, and mixtures thereof. The resist protective coating is not limited thereto.

The resist protective coating may be formed by spin coating a topcoat solution onto a prebaked resist film, and prebaking on a hot plate at 50 to 150° C. for 1 to 10 minutes, preferably at 70 to 140° C. for 1 to 5 minutes. Preferably the protective coating has a thickness in the range of 10 to 500 nm. As in the case of resist compositions, the amount of the protective coating material dispensed in forming a protective coating by spin coating may be reduced by previously wetting the resist film surface with a suitable solvent and applying the protective coating material thereto.

After exposure to high-energy radiation through a photomask, the resist film is post-exposure baked (PEB) on a hot plate at 60 to 150° C. for 1 to 5 minutes, and preferably at 80 to 140° C. for 1 to 3 minutes.

Where a resist protective coating is used, sometimes water is left on the protective coating prior to PEB. If PEB is performed in the presence of residual water, water can penetrate through the protective coating to suck up the acid in the resist during PEB, impeding pattern formation. To fully remove the water on the protective coating prior to PEB, the water on the protective coating should be dried or recovered by suitable means, for example, spin drying, purging the protective coating surface with dry air or nitrogen, or optimizing the shape of a water recovery nozzle on the relevant stage or a water recovery process.

After the exposure, development is carried out by a conventional method such as dip, puddle, or spray development with an aqueous alkaline solution such as tetramethylammonium hydroxide (TMAH) solution. The developer may have a concentration of 0.1 to 5 wt %, preferably 2 to 3 wt %. A typical developer is a 2.38 wt % TMAH aqueous solution. The development time is 10 to 300 seconds, and preferably 0.5 to 2 minutes. These steps result in the formation of the desired pattern on the substrate.

Where polymer P1 is used as an additive to a resist material for use with mask blanks, a resist solution is prepared by adding polymer P1 to a base resin and dissolving them in an organic solvent. The resist solution is coated on a mask blank substrate of $SiO_2$, Cr, CrO, CrN, MoSi or the like. A SOG film and an organic undercoat film may intervene between the resist film and the blank substrate to construct a three-layer structure which is also acceptable herein.

As the base resin of the resist composition for use with mask blanks, novolac resins and hydroxystyrene are often used. Those resins in which alkali soluble hydroxyl groups are substituted by acid labile groups are used for positive resists while these resins in combination with crosslinking agents are used for negative resists. Base polymers which can be used herein include copolymers of hydroxystyrene with one or more of (meth)acrylic derivatives, styrene, vinylnaphthalene, vinylanthracene, vinylpyrene, hydroxyvinylnaphthalene, hydroxyvinylanthracene, indene, hydroxyindene, acenaphthylene, and norbornadiene derivatives.

Once the resist coating is formed, the structure is exposed to EB in vacuum using an EB image-writing system. The exposure is followed by post-exposure baking (PEB) and development in an alkaline developer for 10 to 300 seconds, thereby forming a pattern.

EXAMPLE

Examples are given below by way of illustration and not by way of limitation. The abbreviations Mw and Mn are weight and number average molecular weights, respectively, as measured in tetrahydrofuran solvent by gel permeation chromatography (GPC) versus polystyrene standards, and Mw/Mn is a polydispersity index.

Synthesis Example 1

Fluorinated monomers (1) corresponding to recurring units of formula (1a) which are essential for the polymer to be used as an additive polymer in resist compositions according to the invention were synthesized according to the following formulation.

Synthesis Example 1-1

Synthesis of Monomer 1

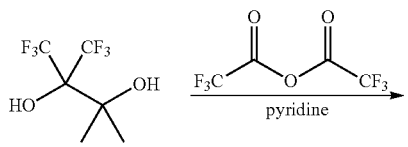

Fluorinated Alcohol 1

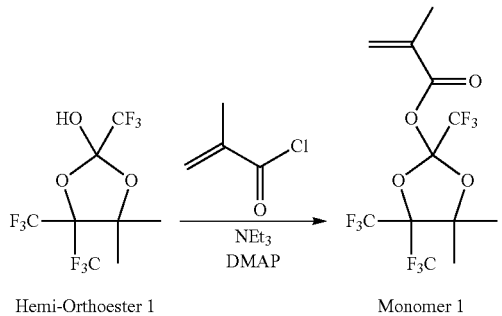

Hemi-Orthoester 1        Monomer 1

Synthesis Example 1-1-1

Synthesis of Hemi-Orthoester 1

A flask was charged with 100 g of Fluorinated Alcohol 1, 87 g of pyridine, and 300 g of acetonitrile. To the contents below 20° C., 232 g of trifluoroacetic anhydride was added dropwise. Stirring was continued at room temperature for 2 hours, after which the reaction solution was poured into 300 g of water to quench the reaction. This was followed by ordinary aqueous work-up and vacuum distillation, obtaining 126 g of Hemi-Orthoester 1 (yield 87%).

Boiling point: 99° C./21 kPa

IR (D-ATR): ν=3608, 3435, 1777, 1403, 1375, 1281, 1223, 1175, 1153, 1079, 1053, 1024, 991, 969, 955, 929, 903, 870, 777, 754, 746, 739, 723, 638 cm$^{-1}$ $^1$H-NMR (600 MHz in DMSO-d$_6$): δ=1.62 (3H, m), 1.74 (3H, m), 10.03 (1H, s) ppm $^{19}$F-NMR (565 MHz in DMSO-d$_6$, trifluoroacetic acid standard): δ=−84.76 (3F, m), −71.97 (3F, m), −70.02 (3F, m) ppm

Synthesis Example 1-1-2

Synthesis of Monomer 1

A flask was charged with 80 g of Hemi-Orthoester 1, 40.2 g of triethylamine, 3 g of 4-dimethylaminopyridine, and 160 g of acetonitrile. To the contents below 20° C., 31.2 g of methacrylic acid chloride in 80 g of acetonitrile was added dropwise. Stirring was continued at room temperature for 4 hours, after which the reaction solution was poured into 240 g of water and 360 g of a 9/1 mixture of hexane and diethyl ether to quench the reaction. This was followed by ordinary aqueous work-up and vacuum distillation, obtaining 61 g of the target compound (yield 75%).

Boiling point: 85° C./1.3 kPa

IR (D-ATR): ν=1762, 1639, 1488, 1459, 1441, 1383, 1298, 1253, 1195, 1158, 1142, 1110, 1074, 1021, 1009, 970, 953, 928, 872, 858, 826, 805, 750, 722, 698, 678, 666, 625 cm$^{-1}$ $^1$H-NMR (600 MHz in DMSO-d$_6$): δ=1.71 (3H, m), 1.74 (3H, m), 1.89 (3H, s), 5.96 (1H, m), 6.13 (1H, s) ppm $^{19}$F-NMR (565 MHz in DMSO-d$_6$, trifluoroacetic acid standard): δ=−79.59 (3F, m), −72.16 (3F, m), −69.97 (3F, m) ppm

Synthesis Example 1-2

Synthesis of Monomer 2

Monomer 2 was synthesized by the same procedure as in Synthesis Example 1-1-2 aside from using acrylic acid chloride instead of methacrylic acid chloride. Yield 83%.

Synthesis Example 1-3

Synthesis of Monomer 3

Monomer 3 was synthesized by the same procedure as in Synthesis Example 1-1-2 aside from using α-trifluoromethylacrylic acid chloride instead of methacrylic acid chloride. Yield 80%.

Synthesis Example 1-4

Synthesis of Monomer 4

Monomer 4 was synthesized by the same procedure as in Synthesis Example 1-1 aside from using pentafluoropropionic anhydride instead of trifluoroacetic anhydride. Two-step yield 71%.

Synthesis Example 1-5

Synthesis of Monomer 5

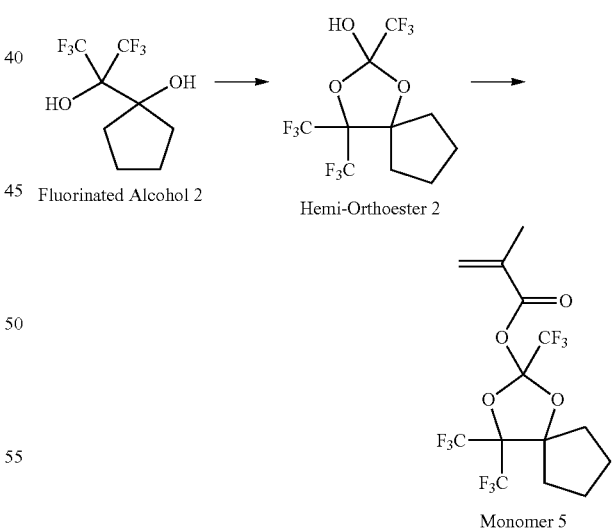

Monomer 5 was synthesized by the same procedure as in Synthesis Example 1-1 aside from using Fluorinated Alcohol 2 instead of Fluorinated Alcohol 1. Two-step yield 70%.

Boiling point: 44-45° C./15 Pa

IR (D-ATR): ν=2970, 2935, 2888, 1761, 1639, 1456, 1440, 1406, 1382, 1296, 1249, 1208, 1166, 1123, 1102, 1073, 1021, 998, 978, 950, 929, 906, 871, 804, 750, 718, 694, 640, 602 cm$^{-1}$ $^1$H-NMR (600 MHz in DMSO-$d_6$): δ=1.65 (1H, m), 1.74-1.95 (4H, m), 1.88 (3H, s), 2.16-2.19 (3H, m), 5.96 (1H, m), 6.13 (1H, s) ppm $^{19}$F-NMR (565 MHz in DMSO-$d_6$, trifluoroacetic acid standard): δ=−80.34 (3F, m), −73.10 (3F, m), −71.29 (3F, m) ppm Synthesis Example 1-6

Synthesis of Monomer 6

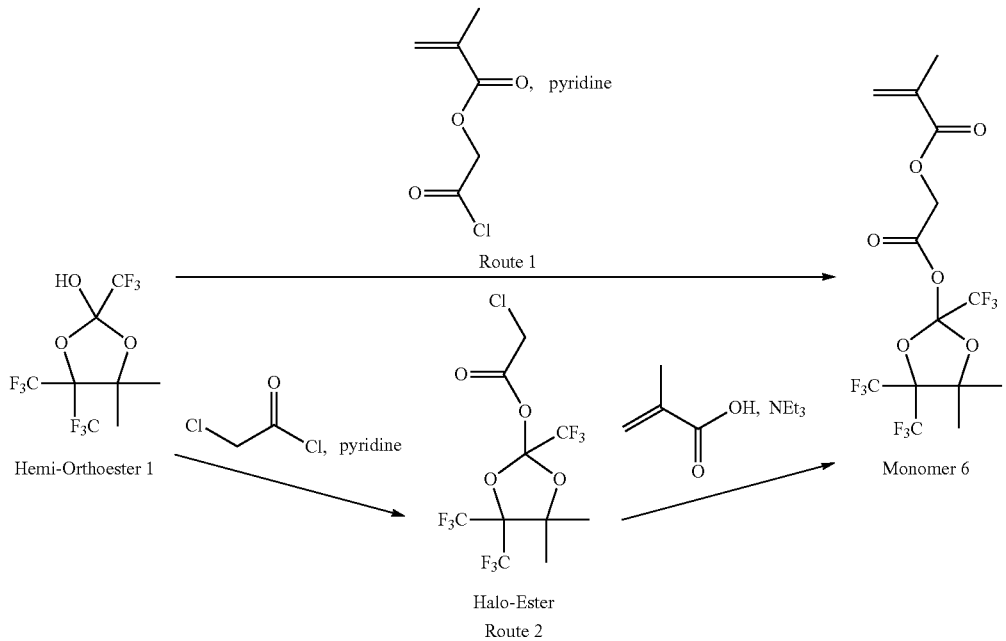

Hemi-Orthoester 1

Halo-Ester

Monomer 6

Synthesis Example 1-6-1

Synthesis of Monomer 6 via Route 1

Monomer 6 was synthesized by the same procedure as in Synthesis Example 1-1-2 aside from using methacryloyloxyacetic acid chloride instead of methacrylic acid chloride. Yield 72%.

Boiling point: 72° C./11 Pa

IR (D-ATR): ν=1810, 1733, 1639, 1487, 1455, 1421, 1403, 1385, 1321, 1298, 1253, 1197, 1158, 1146, 1119, 1084, 1061, 1018, 995, 971, 952, 857, 814, 751, 722, 689, 672, 650, 616, 603, 585, 568 cm$^{-1}$ $^1$H-NMR (600 MHz in DMSO-$d_6$): δ=1.75 (6H, m), 1.90 (3H, m), 4.97 (2H, m), 5.81 (1H, m), 6.12 (1H, m) ppm $^{19}$F-NMR (565 MHz in DMSO-$d_6$, trifluoroacetic acid standard): δ=−80.11 (3F, m), −72.07 (3F, s), −69.63 (3F, m) ppm Synthesis Example 1-6-2

Synthesis of Monomer 6 via Route 2

Monomer 6 was synthesized by the alternative procedure of Route 2.

Synthesis Example 1-6-2-1

Synthesis of Halo-Ester

Halo-Ester was synthesized by the same procedure as in Synthesis Example 1-1-2 aside from using 2-chloroacetic acid instead of methacrylic acid chloride. Yield 64%.

Boiling point: 102° C./13 Pa

IR (D-ATR): ν=1809, 1791, 1488, 1412, 1403, 1384, 1299, 1235, 1197, 1159, 1143, 1118, 1081, 1018, 996, 971, 925, 858, 838, 810, 755, 722, 677, 631, 616, 558 cm$^{-1}$ $^1$H-NMR (600 MHz in DMSO-$d_6$): δ=1.65 (1H, m), 1.75 (6H, m), 4.68 (2H, s) ppm $^{19}$F-NMR (565 MHz in DMSO-$d_6$, trifluoroacetic acid standard): δ=−79.97 (3F, m), −72.14 (3F, s), −69.73 (3F, m) ppm Synthesis Example 1-6-2-2

Synthesis of Monomer 6

A flask was charged with 80 g of Halo-Ester, 34.5 g of methacrylic acid, and 240 g of N,N-dimethylformamide. To the contents below 20° C., 30.4 g of triethylamine was added dropwise, followed by stirring at room temperature for 4 hours. By work-up as in Synthesis Example 1-1-2, Monomer 6 was recovered (yield 74%).

Synthesis Example 1-7

Synthesis of Monomer 7

Monomer 7 was synthesized by the same procedure as in Synthesis Example 1-1-2 aside from using acryloyloxyacetic acid chloride instead of methacrylic acid chloride. Yield 74%.

Synthesis Example 1-8

Synthesis of Monomer 8

Monomer 8 was synthesized by the same procedure as in Synthesis Example 1-1 aside from using pentafluoropropionic anhydride instead of trifluoroacetic anhydride and methacryloyloxyacetic acid chloride instead of methacrylic acid chloride. Yield 69%.

Synthesis Example 1-9

Synthesis of Monomer 9

Monomer 9 was synthesized by the same procedure as in Synthesis Example 1-1-2 aside from using Hemi-Orthoester 2 (Synthesis Example 1-5) instead of Hemi-Orthoester 1 and methacryloyloxyacetic acid chloride instead of methacrylic acid chloride. Yield 73%.

Monomers 1 to 9 of Synthesis Examples are identified below by their structural formula.

Monomer 1

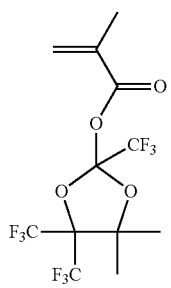

Monomer 2

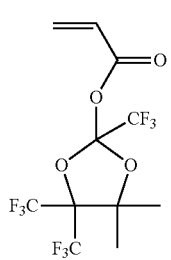

Monomer 3

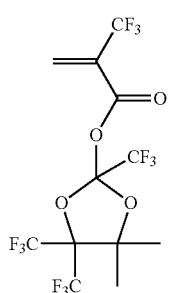

Monomer 4

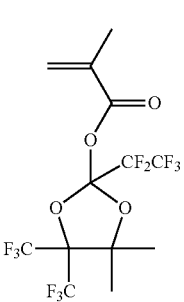

-continued

Monomer 5

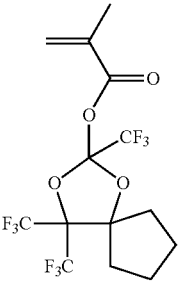

Monomer 6

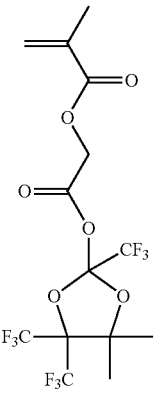

Monomer 7

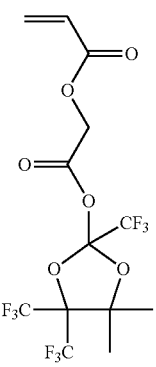

Monomer 8

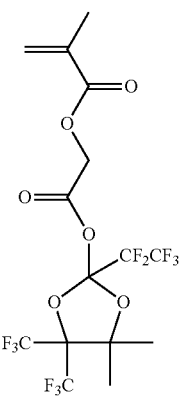

Monomer 9

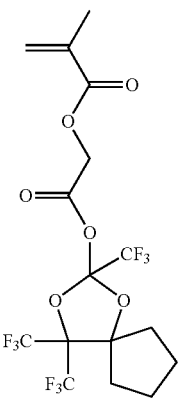

Synthesis Example 2

Polymers were synthesized according to the following formulation.

Synthesis Example 2-1

Synthesis of Polymer 1

In a nitrogen atmosphere, a flask was charged with 10.70 g of Monomer 6, 4.59 g of 4,4,4-trifluoro-3-hydroxy-2-methyl-3-trifluoromethylbutan-2-yl methacrylate, 0.45 g of dimethyl 2,2'-azobis(isobutyrate), and 15 g of a 9/1 mixture of toluene and methyl ethyl ketone to form a monomer solution at a temperature of 20-25° C. In a nitrogen atmosphere, another flask was charged with 7.5 g of a 9/1 mixture of toluene and methyl ethyl ketone, which was heated at 80° C. with stirring. The monomer solution was added dropwise thereto over 4 hours. After the completion of dropwise addition, the solution was stirred for a further 2 hours for polymerization while maintaining the temperature of 80° C. At the end of maturing, the solution was cooled to room temperature and added dropwise to 150 g of hexane whereupon a copolymer precipitated. The copolymer was collected by filtration, washed with 90 g of hexane, and separated as a white solid. The white solid was vacuum dried at 50° C. for 20 hours, yielding the target polymer, designated Polymer 1, in white powder solid form. Amount 11.6 g, yield 74%.

Polymer 1
($c$ = 0.60, $d$ = 0.40, Mw = 8,700)

Synthesis Examples 2-2 to 2-19 and Comparative Synthesis Examples 1-1 to 1-3

Synthesis of Polymers 2 to 19 and comparative Polymers 20 to 22

Polymers were synthesized by the same procedure as in Synthesis Example 2-1, aside from changing the type and amount of monomers. It is noted that the values of formulation in Table 1 are molar ratios of monomer units. The structures of units in Table 1 are shown in Table 2.

TABLE 1

|  |  | Polymer | Unit 1 (ratio) | Unit 2 (ratio) | Unit 3 (ratio) | Mw |
|---|---|---|---|---|---|---|
| Synthesis Example | 2-1 | Polymer 1 | Y-3M (0.60) | Y-7M (0.40) | — | 8,700 |
|  | 2-2 | Polymer 2 | Y-1M (0.60) | Y-7M (0.40) | — | 5,200 |
|  | 2-3 | Polymer 3 | Y-2M (0.60) | Y-7M (0.40) | — | 5,300 |
|  | 2-4 | Polymer 4 | Y-4M (0.60) | Y-7M (0.40) | — | 8,800 |
|  | 2-5 | Polymer 5 | Y-5M (0.60) | Y-7M (0.40) | — | 8,900 |
|  | 2-6 | Polymer 6 | Y-6M (0.60) | Y-7M (0.40) | — | 8,900 |
|  | 2-7 | Polymer 7 | Y-3M (0.60) | Y-8M (0.40) | — | 8,900 |
|  | 2-8 | Polymer 8 | Y-3M (0.40) | Y-7M (0.40) | Y-9M (0.20) | 8,900 |
|  | 2-9 | Polymer 9 | Y-3M (0.40) | Y-7M (0.40) | Y-10M (0.20) | 8,900 |
|  | 2-10 | Polymer 10 | Y-3M (0.40) | Y-7M (0.40) | Y-11M (0.20) | 8,700 |
|  | 2-11 | Polymer 11 | Y-3M (0.40) | Y-7M (0.40) | Y-12M (0.20) | 8,900 |
|  | 2-12 | Polymer 12 | Y-3M (0.40) | Y-7M (0.40) | Y-13M (0.20) | 9,000 |
|  | 2-13 | Polymer 13 | Y-3M (0.40) | Y-7M (0.40) | Y-14M (0.20) | 8,900 |
|  | 2-14 | Polymer 14 | Y-4M (0.40) | Y-7M (0.40) | Y-9M (0.20) | 8,900 |
|  | 2-15 | Polymer 15 | Y-4M (0.40) | Y-7M (0.40) | Y-10M (0.20) | 8,900 |
|  | 2-16 | Polymer 16 | Y-4M (0.40) | Y-7M (0.40) | Y-11M (0.20) | 8,800 |
|  | 2-17 | Polymer 17 | Y-4M (0.40) | Y-7M (0.40) | Y-12M (0.20) | 8,900 |
|  | 2-18 | Polymer 18 | Y-4M (0.40) | Y-7M (0.40) | Y-13M (0.20) | 9,100 |
|  | 2-19 | Polymer 19 | Y-4M (0.50) | Y-7M (0.40) | Y-14M (0.10) | 8,900 |
| Comparative Synthesis Example | 1-1 | Polymer 20 | — | Y-7M (1.00) | — | 8,700 |
|  | 1-2 | Polymer 21 | — | Y-7M (0.40) | Y-11M (0.60) | 9,000 |
|  | 1-3 | Polymer 22 | — | Y-7M (0.40) | Y-15M (0.60) | 9,100 |

TABLE 2
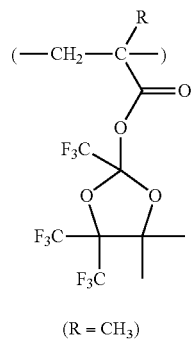 Y-1M
(R = CH₃)
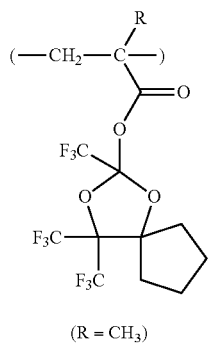 Y-2M
(R = CH₃)
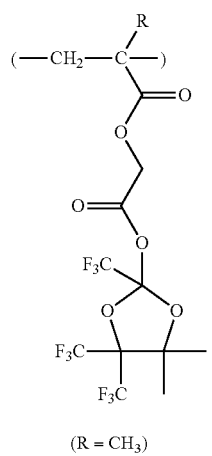 Y-3M
(R = CH₃)
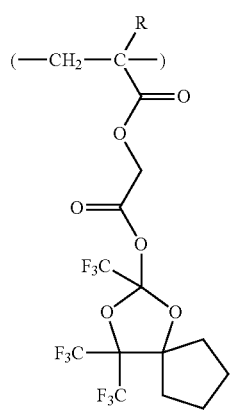 Y-4M
(R = CH₃)
TABLE 2-continued
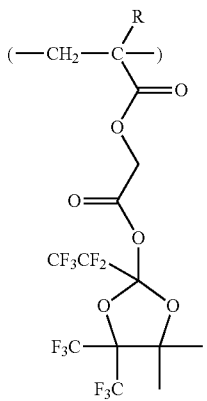 Y-5M
(R = CH₃)
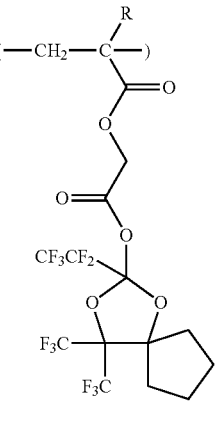 Y-6M
(R = CH₃)
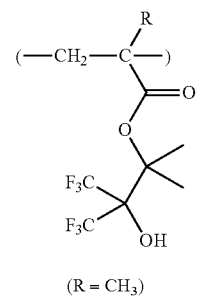 Y-7M
(R = CH₃)
Y-8M
(R = CH₃)

TABLE 2-continued

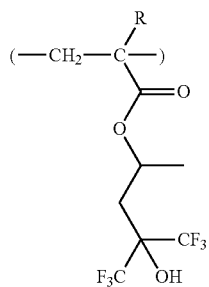
Y-9M

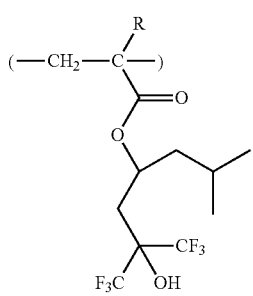
Y-10M

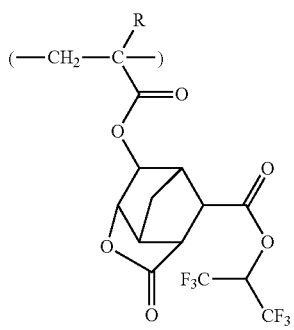
Y-11M

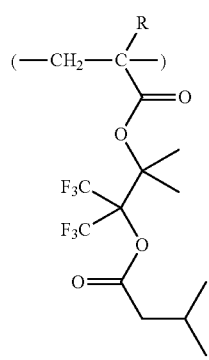
Y-12M

TABLE 2-continued

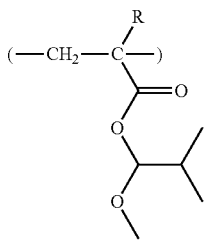
Y-13M

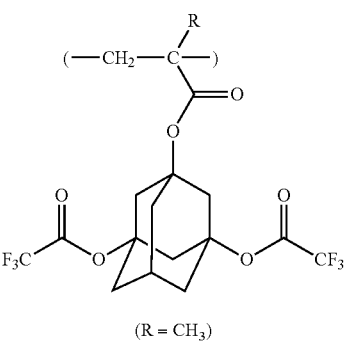
Y-14M

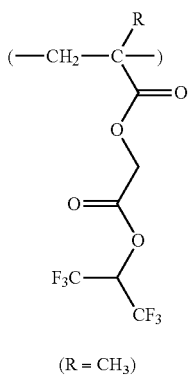
Y-15M

Examples 1-1 to 1-19 and Comparative Examples 1-1 to 1-4

Evaluation of Resist

A resist solution was prepared by dissolving 5 g of Resist Polymer (shown below), 0.25 g of an additive polymer selected from Polymers 1 to 22, 0.25 g of PAG1 (shown below), and 0.05 g of Quencher 1 (shown below) in 75 g of PGMEA and filtering through a polypropylene filter having a pore size of 0.2 μm. In Comparative Example 1-4, a resist solution was similarly prepared aside from omitting the additive polymer.

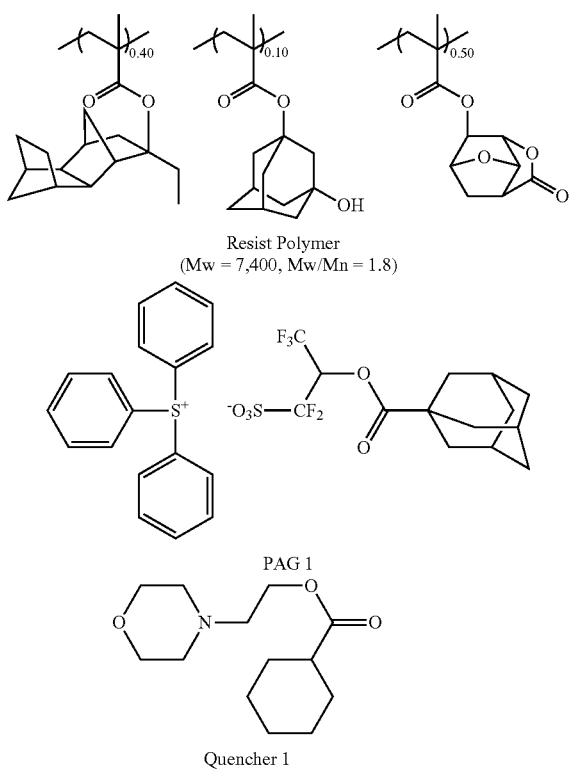

Resist Polymer
(Mw = 7,400, Mw/Mn = 1.8)

PAG 1

Quencher 1

An antireflective coating ARC-29A (Nissan Chemical Co., Ltd.) was deposited on a silicon substrate to a thickness of 87 nm. The resist solution was applied onto the ARC and baked at 90° C. for 60 seconds to form a resist film of 90 nm thick.

A contact angle with water of the resist film was measured, using an inclination contact angle meter Drop Master 500 by Kyowa Interface Science Co., Ltd. Specifically, the wafer covered with the resist film was kept horizontal, and 50 μL of pure water was dropped on the resist film to form a droplet. While the wafer was gradually inclined, the angle (sliding angle) at which the droplet started sliding down was determined as well as receding contact angle. The results are shown in Table 3.

A smaller sliding angle indicates an easier flow of water on the resist film. A larger receding contact angle indicates that fewer liquid droplets are left during high-speed scan exposure. It is demonstrated in Table 3 that the inclusion of the additive polymer of the invention in a resist solution achieves a drastic improvement in the receding contact angle of photoresist film without adversely affecting the sliding angle, as compared with those photoresist films free of the additive polymer.

Also, the resist film-bearing wafer (prepared above) was irradiated through an open frame at an energy dose of 50 mJ/cm$^2$ using an ArF scanner S305B (Nikon Corp.). Then a true circle ring of Teflon® having an inner diameter of 10 cm was placed on the resist film, 10 mL of pure water was carefully injected inside the ring, and the resist film was kept in contact with water at room temperature for 60 seconds. Thereafter, the water was recovered, and a concentration of photoacid generator (PAG1) anion in the water was measured by an LC-MS analyzer (Agilent). The results are also shown in Table 3.

It is evident from Table 3 that a photoresist film formed from a resist solution containing the additive polymer according to the invention is effective in inhibiting the PAG from being leached out of the film in water.

Further, the resist film-bearing wafer (prepared above) was exposed by means of an ArF scanner model S307E (Nikon Corp., NA 0.85, σ 0.93, 4/5 annular illumination, 6% halftone phase shift mask), rinsed for 5 minutes while splashing pure water, post-exposure baked (PEB) at 110° C. for 60 seconds, and developed with a 2.38 wt % TMAH aqueous solution for 60 seconds, forming a 75-nm line-and-space pattern. The wafer was sectioned, and the profile and sensitivity of the 75-nm line-and-space pattern were evaluated. The results are also shown in Table 3.

As seen from Table 3, when exposure is followed by water rinsing, the resist film having the additive polymer according to the invention formulated therein formed a pattern of rectangular profile, in stark contrast with the resist film free of the additive polymer forming a pattern of T-top profile.

TABLE 3

| | Additive Polymer | Sliding angle (°) | Receding contact angle (°) | Anion leach-out (ppb) | Sensitivity (mJ/cm$^2$) | 75-nm pattern profile | Contact angle with water after development (°) |
|---|---|---|---|---|---|---|---|
| Example 1-1 | Polymer 1 | 13 | 86 | 6 | 31 | rectangular | 48 |
| Example 1-2 | Polymer 2 | 15 | 78 | 7 | 31 | rectangular | 74 |
| Example 1-3 | Polymer 3 | 13 | 79 | 6 | 31 | rectangular | 76 |
| Example 1-4 | Polymer 4 | 11 | 86 | 6 | 31 | rectangular | 49 |
| Example 1-5 | Polymer 5 | 12 | 87 | 6 | 31 | rectangular | 48 |
| Example 1-6 | Polymer 6 | 12 | 88 | 6 | 31 | rectangular | 48 |
| Example 1-7 | Polymer 7 | 13 | 86 | 6 | 31 | rectangular | 48 |
| Example 1-8 | Polymer 8 | 14 | 82 | 6 | 31 | rectangular | 49 |
| Example 1-9 | Polymer 9 | 13 | 84 | 6 | 31 | rectangular | 48 |
| Example 1-10 | Polymer 10 | 14 | 82 | 7 | 32 | rectangular | 42 |
| Example 1-11 | Polymer 11 | 11 | 87 | 6 | 31 | rectangular | 60 |
| Example 1-12 | Polymer 12 | 12 | 86 | 6 | 30 | rectangular | 50 |
| Example 1-13 | Polymer 13 | 11 | 90 | 6 | 31 | rectangular | 45 |
| Example 1-14 | Polymer 14 | 14 | 81 | 6 | 31 | rectangular | 49 |
| Example 1-15 | Polymer 15 | 13 | 84 | 6 | 31 | rectangular | 48 |
| Example 1-16 | Polymer 16 | 14 | 81 | 7 | 32 | rectangular | 42 |
| Example 1-17 | Polymer 17 | 11 | 87 | 6 | 31 | rectangular | 60 |
| Example 1-18 | Polymer 18 | 12 | 87 | 6 | 30 | rectangular | 50 |
| Example 1-19 | Polymer 19 | 11 | 89 | 6 | 31 | rectangular | 45 |
| Comparative Example 1-1 | Polymer 20 | 20 | 56 | 5 | 33 | rectangular | 37 |

TABLE 3-continued

|  | Additive Polymer | Sliding angle (°) | Receding contact angle (°) | Anion leach-out (ppb) | Sensitivity (mJ/cm$^2$) | 75-nm pattern profile | Contact angle with water after development (°) |
|---|---|---|---|---|---|---|---|
| Comparative Example 1-2 | Polymer 21 | 18 | 63 | 9 | 33 | rectangular | 25 |
| Comparative Example 1-3 | Polymer 22 | 18 | 72 | 8 | 33 | rectangular | 28 |
| Comparative Example 1-4 | — | 28 | 39 | 60 | 31 | T-top | 75 |

Examples 2-1 to 2-3 and Comparative Examples 2-1 to 2-3

Evaluation of Development Defects

Some resist solutions used in the patterning experiment were precision filtered through a high-density polyethylene filter with a pore size of 0.02 μm. An antireflective coating ARC-29A (Nissan Chemical Co., Ltd.) of 87 nm thick was deposited on a 8-inch silicon substrate. The resist solution was applied onto the ARC and baked at 90° C. for 60 seconds to form a resist film of 90 nm thick. Using an ArF scanner model S307E (Nikon Corp., NA 0.85, a 0.93, Cr mask), the entire surface of the wafer was subjected to checkered-flag exposure including alternate exposure of open-frame exposed and unexposed portions having an area of 20 mm square. This was followed by post-exposure baking (PEB) and development with a 2.38 wt % TMAH aqueous solution for 60 seconds. Using a flaw detector Win-Win 50-1200 (Tokyo Seimitsu Co., Ltd.), the number of blob defects in the unexposed portion of the checkered-flag was counted at the pixel size of 0.125 The results are shown in Table 4.

TABLE 4

|  | Additive polymer | Number of defects |
|---|---|---|
| Example 2-1 | Polymer 1 | 800 |
| Example 2-2 | Polymer 4 | 800 |
| Example 2-3 | Polymer 10 | 400 |
| Comparative Example 2-1 | Polymer 20 | >10,000 |
| Comparative Example 2-2 | Polymer 22 | 3,500 |
| Comparative Example 2-3 | not added | >10,000 |

It is evident from Table 4 that in the resist film from the resist solution free of the additive polymer, numerous development defects were observed after the immersion lithography. The defects could not be obviated by adding Polymer 20 or 22. The resist solution containing the additive polymer (Polymer 1, 4 or 10) according to the invention was effective in minimizing such defects.

Japanese Patent Application No. 2010-088537 is incorporated herein by reference.

Although some preferred embodiments have been described, many modifications and variations may be made thereto in light of the above teachings. It is therefore to be understood that the invention may be practiced otherwise than as specifically described without departing from the scope of the invention claimed.

What is claimed is:

1. A fluorinated monomer having the general formula (1):

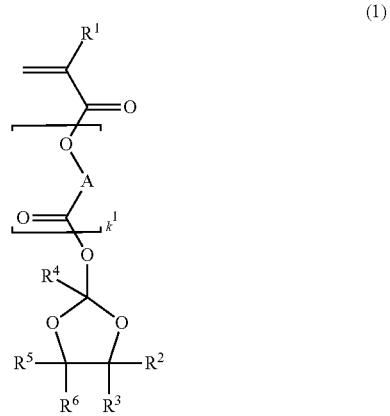

wherein $R^1$ is hydrogen, fluorine, methyl or trifluoromethyl, $R^2$ and $R^3$ are each independently hydrogen or a straight, branched or cyclic $C_1$-$C_{15}$ monovalent hydrocarbon group, $R^2$ and $R^3$ may bond together to form a non-aromatic ring with the carbon atom to which they are attached, $R^4$ to $R^6$ each are a $C_1$-$C_6$ monovalent fluorinated hydrocarbon group, A is a straight, branched or cyclic $C_1$-$C_{10}$ divalent hydrocarbon group, and $k^1$ is an integer of 0 to 2.

* * * * *